US012458210B2

(12) United States Patent
Witte et al.

(10) Patent No.: US 12,458,210 B2
(45) Date of Patent: Nov. 4, 2025

(54) PRESSURE RIGIDIZATION APPARATUSES AND METHODS

(71) Applicant: Neptune Medical Inc., Burlingame, CA (US)

(72) Inventors: Spencer J. Witte, San Francisco, CA (US); Kai Y. Pohlhammer, San Ramon, CA (US); Neal Tanner, Austin, TX (US); Mark C. Scheeff, Oakland, CA (US); Alexander Q. Tilson, Burlingame, CA (US); James M. Hayes, La Honda, CA (US); Afshan S. Chandani, Redwood City, CA (US)

(73) Assignee: Neptune Medical Inc., Burlingame, CA (US)

( * ) Notice: Subject to any disclaimer, the term of this patent is extended or adjusted under 35 U.S.C. 154(b) by 0 days.

(21) Appl. No.: 18/829,229

(22) Filed: Sep. 9, 2024

(65) Prior Publication Data

US 2025/0082178 A1 Mar. 13, 2025

Related U.S. Application Data

(60) Provisional application No. 63/581,266, filed on Sep. 7, 2023.

(51) Int. Cl.
*A61B 1/00* (2006.01)
*A61M 25/00* (2006.01)

(52) U.S. Cl.
CPC ..... *A61B 1/00078* (2013.01); *A61M 25/0043* (2013.01); *A61M 2025/0063* (2013.01)

(58) Field of Classification Search
CPC ............ A61B 1/00078; A61B 1/00071; A61B 1/00082; A61B 1/00135; A61M 25/0043;
(Continued)

(56) References Cited

U.S. PATENT DOCUMENTS

| | | | |
|---|---|---|---|
| 2,268,321 | A | 12/1941 | Flynn |
| 2,767,705 | A | 10/1956 | Moore |

(Continued)

FOREIGN PATENT DOCUMENTS

| | | | |
|---|---|---|---|
| AU | 2013207571 | B2 | 8/2013 |
| CN | 2613655 | Y | 4/2004 |

(Continued)

OTHER PUBLICATIONS

Tilson et al.; U.S. Appl. No. 18/902,916 entitled "Methods of attaching a rigidizing sheath to an endoscope," filed Sep. 30, 2024.
(Continued)

*Primary Examiner* — Kevin C Sirmons
*Assistant Examiner* — Alexandra Lalonde
(74) *Attorney, Agent, or Firm* — Shay Glenn LLP

(57) ABSTRACT

Pressure control systems/sub-systems that improve an operation and safety of dynamically rigidizing devices may control an application of pressure to rigidize/de-rigidize a pressure-rigidizing medical device. Described herein are apparatuses and methods for rigidizing and maintaining rigidization using over-pressurized, transient pulses for the pressure-rigidizing medical device. The apparatuses and methods may rigidize and/or de-rigidize more rapidly and effectively.

15 Claims, 19 Drawing Sheets

(58) Field of Classification Search
CPC ............ A61M 25/0097; A61M 25/005; A61M 2025/0063; A61M 2025/0915; A61M 2025/0065; A61M 2025/0024; A61M 2025/09158; A61M 2025/0064; A61M 2205/15
See application file for complete search history.

(56) References Cited

U.S. PATENT DOCUMENTS

| | | | |
|---|---|---|---|
| 3,859,986 | A | 1/1975 | Okada et al. |
| 3,998,216 | A | 12/1976 | Hosono |
| 4,066,071 | A | 1/1978 | Nagel |
| 4,141,364 | A | 2/1979 | Schultze |
| 4,151,800 | A | 5/1979 | Dotts et al. |
| 4,160,451 | A | 7/1979 | Chittenden |
| 4,176,662 | A | 12/1979 | Frazer |
| 4,425,919 | A | 1/1984 | Alston, Jr. |
| 4,551,140 | A | 11/1985 | Shinohara |
| 4,690,131 | A | 9/1987 | Lyddy, Jr. et al. |
| 4,696,544 | A | 9/1987 | Costella |
| 4,717,379 | A | 1/1988 | Ekholmer |
| 4,794,412 | A | 12/1988 | Casey et al. |
| 4,794,912 | A | 1/1989 | Lia |
| 4,815,450 | A | 3/1989 | Patel |
| 4,817,613 | A | 4/1989 | Jaraczewski et al. |
| 4,890,602 | A | 1/1990 | Hake |
| 4,893,613 | A | 1/1990 | Hake |
| 4,913,369 | A | 4/1990 | Lia et al. |
| 4,959,058 | A | 9/1990 | Michelson |
| 4,961,738 | A | 10/1990 | Mackin |
| 4,967,732 | A | 11/1990 | Inoue |
| 5,018,436 | A | 5/1991 | Evangelista et al. |
| 5,019,121 | A | 5/1991 | Krauter |
| 5,037,386 | A | 8/1991 | Marcus et al. |
| 5,037,404 | A | 8/1991 | Gold et al. |
| 5,050,585 | A | 9/1991 | Takahashi |
| 5,105,819 | A | 4/1992 | Wollschlager et al. |
| 5,123,421 | A | 6/1992 | Sinofsky |
| 5,125,143 | A | 6/1992 | Takahashi |
| 5,174,276 | A | 12/1992 | Crockard |
| 5,188,595 | A | 2/1993 | Jacobi |
| 5,193,525 | A | 3/1993 | Silverstein et al. |
| 5,201,908 | A | 4/1993 | Jones |
| 5,251,611 | A | 10/1993 | Zehel et al. |
| 5,337,733 | A | 8/1994 | Bauerfeind et al. |
| 5,360,440 | A | 11/1994 | Andersen |
| 5,447,148 | A | 9/1995 | Oneda et al. |
| 5,496,292 | A | 3/1996 | Burnham |
| 5,531,685 | A | 7/1996 | Hemmer et al. |
| 5,531,719 | A | 7/1996 | Takahashi |
| 5,577,992 | A | 11/1996 | Chiba et al. |
| 5,601,588 | A | 2/1997 | Tonomura et al. |
| 5,603,991 | A | 2/1997 | Kupiecki et al. |
| 5,607,435 | A | 3/1997 | Sachdeva et al. |
| 5,624,381 | A | 4/1997 | Kieturakis |
| 5,632,734 | A | 5/1997 | Galel et al. |
| 5,637,075 | A | 6/1997 | Kikawada |
| 5,662,587 | A | 9/1997 | Grundfest et al. |
| 5,662,621 | A | 9/1997 | Lafontaine |
| 5,746,692 | A | 5/1998 | Bacich et al. |
| 5,749,828 | A | 5/1998 | Solomon et al. |
| 5,759,151 | A | 6/1998 | Sturges |
| 5,779,624 | A | 7/1998 | Chang |
| 5,782,811 | A | 7/1998 | Samson et al. |
| 5,823,961 | A | 10/1998 | Fields et al. |
| 5,882,347 | A | 3/1999 | Mouris Laan et al. |
| 5,891,112 | A | 4/1999 | Samson |
| 5,891,114 | A | 4/1999 | Chin et al. |
| 5,906,591 | A | 5/1999 | Dario et al. |
| 5,916,145 | A | 6/1999 | Chu et al. |
| 5,916,147 | A | 6/1999 | Boury |
| 5,951,539 | A | 9/1999 | Nita et al. |
| 5,976,074 | A | 11/1999 | Moriyama |
| 6,090,099 | A | 7/2000 | Samson et al. |
| 6,159,187 | A | 12/2000 | Park et al. |
| 6,162,171 | A | 12/2000 | Ng et al. |
| 6,165,123 | A | 12/2000 | Thompson |
| 6,179,776 | B1 | 1/2001 | Adams et al. |
| 6,190,357 | B1 | 2/2001 | Ferrari et al. |
| 6,217,565 | B1 | 4/2001 | Cohen |
| 6,296,644 | B1 | 10/2001 | Surat et al. |
| 6,309,346 | B1 | 10/2001 | Farhadi |
| 6,352,503 | B1 | 3/2002 | Matsu et al. |
| 6,364,878 | B1 | 4/2002 | Hall |
| 6,368,315 | B1 | 4/2002 | Gillis et al. |
| 6,468,203 | B2 | 10/2002 | Belson |
| 6,485,409 | B1 | 11/2002 | Voloshin et al. |
| 6,503,225 | B1 | 1/2003 | Kirsch et al. |
| 6,517,477 | B1 | 2/2003 | Wendlandt |
| 6,547,724 | B1 | 4/2003 | Soble et al. |
| 6,572,538 | B2 | 6/2003 | Takase |
| 6,572,590 | B1 | 6/2003 | Stevens et al. |
| 6,579,277 | B1 | 6/2003 | Rabiner et al. |
| 6,610,007 | B2 | 8/2003 | Belson et al. |
| 6,612,982 | B1 | 9/2003 | Ouchi |
| 6,616,628 | B2 | 9/2003 | Hayzelden |
| 6,620,126 | B2 | 9/2003 | Unsworth et al. |
| 6,623,424 | B2 | 9/2003 | Hayakawa et al. |
| 6,712,832 | B2 | 3/2004 | Shah |
| 6,726,677 | B1 | 4/2004 | Flaherty et al. |
| 6,730,020 | B2 | 5/2004 | Peng et al. |
| 6,780,151 | B2 | 8/2004 | Grabover et al. |
| 6,783,491 | B2 | 8/2004 | Saadat et al. |
| 6,790,173 | B2 | 9/2004 | Saadat et al. |
| 6,793,621 | B2 | 9/2004 | Butler et al. |
| 6,793,661 | B2 | 9/2004 | Hamilton et al. |
| 6,800,056 | B2 | 10/2004 | Tartaglia et al. |
| 6,869,393 | B2 | 3/2005 | Butler |
| 6,899,673 | B2 | 5/2005 | Ogura et al. |
| 6,911,004 | B2 | 6/2005 | Kim et al. |
| 6,923,754 | B2 | 8/2005 | Lubock |
| 6,960,162 | B2 | 11/2005 | Saadat et al. |
| 6,974,411 | B2 | 12/2005 | Belson |
| 6,984,203 | B2 | 1/2006 | Tartaglia et al. |
| 7,060,199 | B2 | 6/2006 | Woydt et al. |
| 7,172,552 | B2 | 2/2007 | Wendlandt |
| 7,214,230 | B2 | 5/2007 | Brock et al. |
| 7,273,469 | B1 | 9/2007 | Chan et al. |
| 7,288,101 | B2 | 10/2007 | Deem et al. |
| 7,291,127 | B2 | 11/2007 | Eldenschink |
| 7,354,427 | B2 | 4/2008 | Fangrow |
| 7,365,509 | B2 | 4/2008 | Park et al. |
| 7,438,712 | B2 | 10/2008 | Chouinard |
| 7,511,733 | B2 | 3/2009 | Takizawa et al. |
| 7,537,562 | B2 | 5/2009 | Takano |
| 7,559,916 | B2 | 7/2009 | Smith et al. |
| 7,591,782 | B2 | 9/2009 | Fujikura |
| 7,598,652 | B2 | 10/2009 | Kornbluh et al. |
| 7,658,738 | B2 | 2/2010 | Nobis et al. |
| 7,695,428 | B2 | 4/2010 | Machida |
| 7,736,323 | B2 | 6/2010 | Von Weymarn-Scharli |
| 7,749,196 | B2 | 7/2010 | Osborne et al. |
| 7,837,615 | B2 | 11/2010 | Le et al. |
| 7,850,725 | B2 | 12/2010 | Vardi et al. |
| 7,901,347 | B2 | 3/2011 | Sekiguchi et al. |
| 7,909,755 | B2 | 3/2011 | Itoi |
| 7,918,819 | B2 | 4/2011 | Karmarkar et al. |
| 7,918,845 | B2 | 4/2011 | Saadat et al. |
| 7,931,661 | B2 | 4/2011 | Saadat et al. |
| 7,935,047 | B2 | 5/2011 | Yoshida et al. |
| 7,947,000 | B2 | 5/2011 | Vargas et al. |
| 7,957,790 | B2 | 6/2011 | Kleen |
| 7,970,455 | B2 | 6/2011 | Zilberstein et al. |
| 7,988,621 | B2 | 8/2011 | Smith et al. |
| 8,047,236 | B2 | 11/2011 | Perry |
| 8,075,476 | B2 | 12/2011 | Vargas |
| 8,092,374 | B2 | 1/2012 | Smith et al. |
| 8,109,953 | B1 | 2/2012 | King, III et al. |
| 8,123,739 | B2 | 2/2012 | McQueen et al. |
| 8,125,755 | B2 | 2/2012 | Garcia et al. |
| 8,192,422 | B2 | 6/2012 | Zubiate et al. |
| 8,206,287 | B2 | 6/2012 | Matsuo |
| 8,226,548 | B2 | 7/2012 | Kucklick |
| 8,241,299 | B2 | 8/2012 | Hibner |

(56) References Cited

U.S. PATENT DOCUMENTS 8,246,575 B2 8/2012 Viola
8,257,257 B2 9/2012 Takizawa et al.
8,262,677 B2 9/2012 Goto
8,298,161 B2 10/2012 Vargas
8,313,014 B2 11/2012 Bettuchi
8,361,090 B2 1/2013 Belson
8,366,606 B2 2/2013 Watanabe et al.
8,388,519 B2 3/2013 Garcia et al.
8,439,825 B2 5/2013 Sekiguchi
8,460,179 B2 6/2013 Ikeda et al.
8,485,968 B2 7/2013 Weimer et al.
8,496,648 B2 7/2013 Rogers
8,506,479 B2 8/2013 Piskun et al.
8,517,923 B2 8/2013 Belson et al.
8,545,491 B2 10/2013 Abboud et al.
8,550,989 B2 10/2013 Dohi et al.
8,556,804 B2 10/2013 Smith et al.
8,663,096 B2 3/2014 Viola
8,663,196 B2 3/2014 Kassab et al.
8,708,894 B2 4/2014 Smith et al.
8,721,530 B2 5/2014 Ohline et al.
8,753,312 B2 6/2014 Bowe et al.
8,777,844 B1 7/2014 Sadanand
8,920,369 B2 12/2014 Salahieh et al.
8,969,639 B2 3/2015 Xu et al.
8,992,420 B2 3/2015 Maahs et al.
9,011,318 B2 4/2015 Choset et al.
9,066,655 B2 6/2015 Stefanchik et al.
9,114,228 B2 8/2015 Zook et al.
9,125,653 B2 9/2015 Kovach
9,155,451 B2 10/2015 Smith et al.
9,192,284 B2 11/2015 Hirsch et al.
9,192,288 B2 11/2015 Okaniwa
9,211,140 B2 12/2015 Lauryssen et al.
9,220,398 B2 12/2015 Woodley et al.
9,226,825 B2 1/2016 Starksen et al.
9,241,611 B2 1/2016 Konno
9,254,123 B2 2/2016 Alvarez et al.
9,282,993 B1 3/2016 Cohen et al.
9,295,511 B2 3/2016 Smith et al.
9,333,287 B2 5/2016 Nitsan et al.
9,358,073 B2 6/2016 Piligian et al.
9,364,955 B2 6/2016 Oyola et al.
9,386,910 B2 7/2016 West
9,498,108 B1 11/2016 Lombardi
9,498,198 B2 11/2016 Hu et al.
9,505,125 B2 11/2016 Zubiate et al.
9,585,546 B2 3/2017 Surti et al.
9,610,068 B2 4/2017 Kappel et al.
9,649,473 B2 5/2017 Gregorich et al.
9,763,562 B2 9/2017 Avitsian et al.
9,814,372 B2 11/2017 Smith et al.
9,913,570 B2 3/2018 Kucharski et al.
9,937,324 B2 4/2018 Kim et al.
9,993,142 B2 6/2018 Salman et al.
10,092,291 B2 10/2018 Voegele et al.
10,307,042 B2 6/2019 Lombardi
10,463,495 B2 11/2019 Rogers et al.
10,625,413 B1 4/2020 McPherson
11,006,975 B1 5/2021 Cohen et al.
11,020,214 B2 6/2021 Gupta et al.
11,122,971 B2 9/2021 Tilson et al.
11,135,398 B2 10/2021 Tilson et al.
11,219,351 B2 1/2022 Tilson et al.
11,478,608 B2 10/2022 Tilson et al.
11,554,248 B1 1/2023 Tilson et al.
11,724,065 B2 8/2023 Tilson et al.
11,744,443 B2 9/2023 Lopez et al.
11,793,392 B2 10/2023 Tilson et al.
11,937,778 B2 3/2024 Tilson et al.
11,944,277 B2 4/2024 Tilson et al.
12,059,128 B2 8/2024 Tilson et al.
12,082,776 B2 9/2024 Tilson et al.
12,102,289 B2 10/2024 Tilson et al.
12,121,677 B2 10/2024 Gomes et al.
2001/0041881 A1 11/2001 Sarge et al.
2002/0049423 A1 4/2002 Howell et al.
2002/0107478 A1 8/2002 Wendlandt
2002/0161355 A1 10/2002 Wollschlager
2003/0023259 A1 1/2003 Dubrul et al.
2003/0035048 A1 2/2003 Shipp
2003/0036748 A1 2/2003 Cooper et al.
2003/0083546 A1 5/2003 Butler et al.
2003/0122374 A1 7/2003 Ouchi et al.
2003/0153866 A1 8/2003 Long et al.
2003/0208220 A1 11/2003 Worley et al.
2003/0216681 A1 11/2003 Zhang et al.
2003/0216691 A1 11/2003 Jacobson
2003/0225379 A1 12/2003 Schaffer et al.
2004/0019252 A1 1/2004 Hirata
2004/0044350 A1 3/2004 Martin et al.
2004/0092960 A1 5/2004 Abrams et al.
2004/0186349 A1 9/2004 Ewers et al.
2004/0186350 A1 9/2004 Brenneman et al.
2004/0242958 A1 12/2004 Fujikawa et al.
2004/0243227 A1 12/2004 Starksen et al.
2004/0260236 A1 12/2004 Manning et al.
2005/0005363 A1 1/2005 Giori et al.
2005/0010237 A1 1/2005 Niazi
2005/0085829 A1 4/2005 Kraemer et al.
2005/0154258 A1 7/2005 Tartaglia et al.
2005/0165275 A1 7/2005 Von Felten et al.
2005/0165366 A1 7/2005 Brustad et al.
2005/0203340 A1 9/2005 Butler et al.
2005/0261581 A1 11/2005 Hughes et al.
2005/0272974 A1 12/2005 Iddan
2005/0277966 A1 12/2005 Ewers et al.
2006/0041188 A1 2/2006 Dirusso et al.
2006/0047183 A1 3/2006 Park
2006/0058582 A1 3/2006 Maahs et al.
2006/0063973 A1 3/2006 Makower et al.
2006/0129130 A1 6/2006 Tal et al.
2006/0178560 A1 8/2006 Saadat et al.
2006/0192465 A1 8/2006 Kornbluh et al.
2006/0199999 A1 9/2006 Ikeda et al.
2006/0235457 A1 10/2006 Belson
2006/0235458 A1 10/2006 Belson
2006/0258906 A1 11/2006 Binmoeller
2006/0264707 A1 11/2006 Kinney
2006/0264821 A1 11/2006 Vo et al.
2006/0287666 A1 12/2006 Saadat et al.
2007/0015965 A1 1/2007 Cox et al.
2007/0038025 A1 2/2007 Yoshida
2007/0045504 A1 3/2007 Wollschlager
2007/0088367 A1 4/2007 Von Weymarn-Scharli
2007/0100414 A1 5/2007 Licata et al.
2007/0106302 A1 5/2007 Ortiz
2007/0118015 A1 5/2007 Wendlandt
2007/0135803 A1 6/2007 Belson
2007/0156018 A1 7/2007 Krauter et al.
2007/0219411 A1 9/2007 Dejima et al.
2007/0239252 A1 10/2007 Hopkins et al.
2007/0250113 A1 10/2007 Hegeman et al.
2007/0250149 A1 10/2007 Oepen et al.
2007/0255101 A1 11/2007 Bar Or
2007/0260121 A1 11/2007 Bakos et al.
2007/0282358 A1 12/2007 Remiszewski et al.
2008/0051635 A1 2/2008 Tanaka et al.
2008/0058722 A1 3/2008 Oepen et al.
2008/0091073 A1 4/2008 Park
2008/0103440 A1 5/2008 Ferren et al.
2008/0139887 A1 6/2008 Fitzpatrick
2008/0172037 A1 7/2008 Huang et al.
2008/0188928 A1 8/2008 Salahieh et al.
2008/0200762 A1 8/2008 Stokes et al.
2008/0214893 A1 9/2008 Tartaglia et al.
2008/0234546 A1 9/2008 Kawano et al.
2008/0242928 A1 10/2008 Kawano et al.
2008/0249362 A1 10/2008 Jiang et al.
2008/0262300 A1 10/2008 Ewers et al.
2008/0275299 A1 11/2008 Park
2009/0023983 A1 1/2009 Stefanchik
2009/0048483 A1 2/2009 Yamamoto
2009/0062611 A1 3/2009 Toyama

(56) References Cited

U.S. PATENT DOCUMENTS

| | | | |
|---|---|---|---|
| 2009/0062837 A1 | 3/2009 | Gasche et al. | |
| 2009/0062872 A1 | 3/2009 | Chin et al. | |
| 2009/0112063 A1 | 4/2009 | Bakos et al. | |
| 2009/0131752 A1 | 5/2009 | Park | |
| 2009/0157068 A1 | 6/2009 | Kallel et al. | |
| 2009/0187163 A1 | 7/2009 | Uihlein | |
| 2009/0240202 A1 | 9/2009 | Drasler et al. | |
| 2009/0248041 A1 | 10/2009 | Williams et al. | |
| 2009/0259200 A1 | 10/2009 | Lampropoulos et al. | |
| 2009/0264704 A1 | 10/2009 | Shtul | |
| 2010/0010308 A1 | 1/2010 | Braun et al. | |
| 2010/0010437 A1 | 1/2010 | Miles et al. | |
| 2010/0010504 A1 | 1/2010 | Simaan et al. | |
| 2010/0016663 A1 | 1/2010 | Maisch et al. | |
| 2010/0036363 A1 | 2/2010 | Watanabe et al. | |
| 2010/0069712 A1 | 3/2010 | Yamaya | |
| 2010/0069716 A1 | 3/2010 | Chin et al. | |
| 2010/0076451 A1 | 3/2010 | Zwolinski et al. | |
| 2010/0087711 A1 | 4/2010 | Edwards | |
| 2010/0137686 A1 | 6/2010 | Meron et al. | |
| 2010/0145151 A1 | 6/2010 | Fukunaga et al. | |
| 2010/0160735 A1 | 6/2010 | Bakos | |
| 2010/0185172 A1 | 7/2010 | Fabro | |
| 2010/0204546 A1 | 8/2010 | Hassidov et al. | |
| 2010/0268025 A1 | 10/2010 | Belson | |
| 2010/0331625 A1 | 12/2010 | Rosemurgy et al. | |
| 2010/0331820 A1 | 12/2010 | Prisco et al. | |
| 2011/0015729 A1 | 1/2011 | Jimenez et al. | |
| 2011/0023888 A1 | 2/2011 | Vazales et al. | |
| 2011/0040282 A1 | 2/2011 | Uihlein | |
| 2011/0046442 A1 | 2/2011 | Matsushita | |
| 2011/0049282 A1 | 3/2011 | Danielsson | |
| 2011/0054253 A1 | 3/2011 | Jordá Albiñana et al. | |
| 2011/0087070 A1 | 4/2011 | Tilson et al. | |
| 2011/0237888 A1 | 9/2011 | Matsushita | |
| 2011/0245611 A1 | 10/2011 | Yeh et al. | |
| 2011/0282149 A1 | 11/2011 | Vargas et al. | |
| 2011/0288553 A1 | 11/2011 | Jansen et al. | |
| 2011/0301414 A1 | 12/2011 | Hotto et al. | |
| 2011/0306950 A1 | 12/2011 | Cucin | |
| 2011/0319714 A1 | 12/2011 | Roelle et al. | |
| 2012/0004676 A1 | 1/2012 | Vargas | |
| 2012/0022329 A1 | 1/2012 | Wagh et al. | |
| 2012/0041291 A1 | 2/2012 | Ferren et al. | |
| 2012/0095548 A1 | 4/2012 | Gregorich et al. | |
| 2012/0108902 A1 | 5/2012 | Frassica et al. | |
| 2012/0130173 A1 | 5/2012 | Lutze et al. | |
| 2012/0143005 A1 | 6/2012 | Yeh et al. | |
| 2012/0165607 A1 | 6/2012 | Ashida et al. | |
| 2012/0165792 A1 | 6/2012 | Ortiz et al. | |
| 2012/0172651 A1 | 7/2012 | Cutrer | |
| 2012/0209062 A1 | 8/2012 | Qiao | |
| 2012/0277528 A1 | 11/2012 | Qiao | |
| 2012/0277729 A1 | 11/2012 | Melsheimer | |
| 2013/0131641 A1 | 5/2013 | Jimenez et al. | |
| 2013/0190565 A1 | 7/2013 | Gora et al. | |
| 2013/0274553 A1 | 10/2013 | Piskun | |
| 2013/0304179 A1 | 11/2013 | Bialas et al. | |
| 2013/0333472 A1 | 12/2013 | Georgeson | |
| 2013/0338440 A1 | 12/2013 | Sinai et al. | |
| 2014/0005683 A1 | 1/2014 | Stand et al. | |
| 2014/0073853 A1 | 3/2014 | Swisher et al. | |
| 2014/0081169 A1 | 3/2014 | Gerding et al. | |
| 2014/0088459 A1 | 3/2014 | Roush et al. | |
| 2014/0142393 A1 | 5/2014 | Piskun et al. | |
| 2014/0155702 A1 | 6/2014 | Tilson et al. | |
| 2014/0155783 A1 | 6/2014 | Starksen et al. | |
| 2014/0188054 A1 | 7/2014 | Iijima et al. | |
| 2014/0234600 A1 | 8/2014 | Wang et al. | |
| 2014/0243873 A1 | 8/2014 | Franklin | |
| 2014/0275860 A1 | 9/2014 | Rottenberg et al. | |
| 2014/0276601 A1 | 9/2014 | Edward | |
| 2014/0276642 A1 | 9/2014 | Cully et al. | |
| 2014/0309587 A1 | 10/2014 | Kim et al. | |
| 2014/0343358 A1 | 11/2014 | Hameed et al. | |
| 2014/0371718 A1 | 12/2014 | Alvarez et al. | |
| 2014/0371764 A1 | 12/2014 | Oyola et al. | |
| 2015/0018616 A1 | 1/2015 | Kumoyama | |
| 2015/0038919 A1 | 2/2015 | Bramwell et al. | |
| 2015/0073216 A1 | 3/2015 | Papay | |
| 2015/0073342 A1 | 3/2015 | Pacheco et al. | |
| 2015/0073409 A1 | 3/2015 | Watson et al. | |
| 2015/0094656 A1 | 4/2015 | Salahieh et al. | |
| 2015/0119640 A1 | 4/2015 | Reydel | |
| 2015/0126814 A1 | 5/2015 | Mesallum et al. | |
| 2015/0133729 A1 | 5/2015 | Reydel | |
| 2015/0142013 A1 | 5/2015 | Tanner et al. | |
| 2015/0148602 A1 | 5/2015 | Hill et al. | |
| 2015/0148606 A1 | 5/2015 | Rottenberg et al. | |
| 2015/0164314 A1 | 6/2015 | Peterson | |
| 2015/0216589 A1 | 8/2015 | Wittenberger et al. | |
| 2015/0342608 A1 | 12/2015 | Hernandez | |
| 2015/0369325 A1 | 12/2015 | Bureau et al. | |
| 2016/0007832 A1 | 1/2016 | Shimada | |
| 2016/0015259 A1 | 1/2016 | Mody et al. | |
| 2016/0058268 A1 | 3/2016 | Salman et al. | |
| 2016/0066773 A1 | 3/2016 | Cooper et al. | |
| 2016/0096004 A1 | 4/2016 | Gerrans et al. | |
| 2016/0129547 A1 | 5/2016 | Duescher et al. | |
| 2016/0136393 A1 | 5/2016 | Tsai et al. | |
| 2016/0174829 A1 | 6/2016 | Reydel | |
| 2016/0198935 A1 | 7/2016 | Choi et al. | |
| 2016/0206425 A1 | 7/2016 | Madrid et al. | |
| 2016/0270870 A1 | 9/2016 | Kowshik | |
| 2016/0279388 A1 | 9/2016 | Barrish et al. | |
| 2016/0287059 A1 | 10/2016 | Ha et al. | |
| 2016/0324412 A1 | 11/2016 | Hassidov et al. | |
| 2017/0156567 A1 | 6/2017 | Kaneko | |
| 2017/0157363 A1 | 6/2017 | Barrish et al. | |
| 2017/0312920 A1 | 11/2017 | Yip et al. | |
| 2017/0340862 A1 | 11/2017 | Calabrese et al. | |
| 2017/0360281 A1 | 12/2017 | Ponsky | |
| 2018/0015257 A1 | 1/2018 | Krolik et al. | |
| 2018/0043134 A1 | 2/2018 | Alvarez et al. | |
| 2018/0064366 A1 | 3/2018 | Sweeney et al. | |
| 2018/0085559 A1* | 3/2018 | Laby | A61M 25/0155 |
| 2018/0132705 A1 | 5/2018 | Higuchi | |
| 2018/0184885 A1 | 7/2018 | St. George | |
| 2018/0249893 A1 | 9/2018 | Yeung et al. | |
| 2018/0256876 A1 | 9/2018 | Furnish et al. | |
| 2018/0263469 A1 | 9/2018 | Okaniwa et al. | |
| 2018/0264239 A1 | 9/2018 | Piskun | |
| 2018/0289925 A1 | 10/2018 | Palmer et al. | |
| 2018/0326197 A1 | 11/2018 | McArthur et al. | |
| 2018/0361116 A1 | 12/2018 | Quick et al. | |
| 2018/0374603 A1 | 12/2018 | Greenwood | |
| 2019/0046012 A1 | 2/2019 | Ikeda | |
| 2019/0226447 A1 | 7/2019 | Stecher et al. | |
| 2020/0022712 A1 | 1/2020 | Deville et al. | |
| 2020/0030575 A1 | 1/2020 | Bogusky et al. | |
| 2020/0100653 A1 | 4/2020 | Nakamura | |
| 2020/0171276 A1 | 6/2020 | Onozuka | |
| 2020/0178763 A1 | 6/2020 | Tilson et al. | |
| 2020/0230808 A1 | 7/2020 | Simaan et al. | |
| 2020/0315429 A1 | 10/2020 | Russo et al. | |
| 2020/0315433 A1 | 10/2020 | Axon et al. | |
| 2020/0383677 A1 | 12/2020 | Piligian et al. | |
| 2021/0000505 A1 | 1/2021 | Lenker et al. | |
| 2021/0030260 A1 | 2/2021 | Julian et al. | |
| 2021/0045626 A1 | 2/2021 | Hsu et al. | |
| 2021/0114507 A1 | 4/2021 | Alexander et al. | |
| 2021/0197684 A1 | 7/2021 | Graham et al. | |
| 2021/0323767 A1 | 10/2021 | Liu et al. | |
| 2022/0323166 A1 | 10/2022 | Tilson et al. | |
| 2022/0347430 A1* | 11/2022 | Pedersen | A61M 25/0097 |
| 2023/0017488 A1 | 1/2023 | Somasundaram et al. | |
| 2023/0070264 A1 | 3/2023 | Leuthardt et al. | |
| 2023/0121021 A1 | 4/2023 | Sinay et al. | |
| 2023/0210351 A1 | 7/2023 | Scheeff et al. | |
| 2023/0338702 A1 | 10/2023 | Tilson et al. | |
| 2023/0346204 A1 | 11/2023 | Tilson et al. | |
| 2023/0346205 A1 | 11/2023 | Tilson et al. | |
| 2023/0346399 A1 | 11/2023 | Schaller et al. | |
| 2023/0380662 A1 | 11/2023 | Slawinski et al. | |

(56) References Cited

U.S. PATENT DOCUMENTS

| | | | | |
|---|---|---|---|---|
| 2024/0016638 | A1 | 1/2024 | McGowan et al. | |
| 2024/0016639 | A1 | 1/2024 | McGowan et al. | |
| 2024/0024640 | A1 | 1/2024 | Gomes et al. | |
| 2024/0081619 | A1 | 3/2024 | Tilson et al. | |
| 2024/0082557 | A1 | 3/2024 | Tilson et al. | |
| 2024/0090744 | A1 | 3/2024 | Lopez et al. | |
| 2024/0165833 | A1 | 5/2024 | Tanner et al. | |
| 2024/0293003 | A1 | 9/2024 | Tilson et al. | |
| 2024/0358232 | A1* | 10/2024 | Joseph | A61B 34/70 |
| 2025/0134352 | A1 | 5/2025 | Tilson et al. | |
| 2025/0169678 | A1 | 5/2025 | Tilson et al. | |

FOREIGN PATENT DOCUMENTS

| | | | |
|---|---|---|---|
| CN | 1706349 | A | 12/2005 |
| CN | 1732855 | A | 2/2006 |
| CN | 1806770 | A | 7/2006 |
| CN | 1861011 | A | 11/2006 |
| CN | 101119765 | A | 2/2008 |
| CN | 101129255 | A | 2/2008 |
| CN | 101888872 | A | 11/2010 |
| CN | 102137628 | A | 7/2011 |
| CN | 201899767 | U | 7/2011 |
| CN | 102711585 | A | 10/2012 |
| CN | 102872519 | A | 1/2013 |
| CN | 103384500 | A | 11/2013 |
| CN | 104168860 | A | 11/2014 |
| CN | 104287684 | B | 3/2016 |
| CN | 105759418 | A | 7/2016 |
| CN | 105813536 | A | 7/2016 |
| CN | 105832279 | A | 8/2016 |
| CN | 106137397 | A | 11/2016 |
| CN | 106455929 | A | 2/2017 |
| CN | 106488744 | A | 3/2017 |
| CN | 106659367 | A | 5/2017 |
| CN | 106823102 | A | 6/2017 |
| CN | 107296584 | A | 10/2017 |
| CN | 107697631 | A | 2/2018 |
| CN | 110077771 | A | 8/2019 |
| CN | 212558299 | U | 2/2021 |
| DE | 102005039601 | A1 | 2/2007 |
| EP | 401129 | A1 | 12/1990 |
| EP | 0941743 | A2 | 9/1999 |
| EP | 1662972 | A2 | 6/2006 |
| EP | 1695657 | A1 | 8/2006 |
| EP | 1487318 | B1 | 3/2008 |
| EP | 2016914 | A2 | 1/2009 |
| EP | 1499227 | B1 | 10/2010 |
| EP | 2258322 | A2 | 12/2010 |
| EP | 2364637 | A1 | 9/2011 |
| EP | 2368481 | A1 | 9/2011 |
| EP | 2368483 | A1 | 9/2011 |
| EP | 3256052 | A1 | 12/2017 |
| EP | 2604175 | B1 | 11/2019 |
| GB | 2482355 | A | 10/2010 |
| GB | 2497544 | A | 6/2013 |
| JP | S6289014 | A | 4/1987 |
| JP | H05220102 | A | 8/1993 |
| JP | H05293077 | A | 11/1993 |
| JP | H0644503 | U | 6/1994 |
| JP | 2002125921 | A | 5/2002 |
| JP | 2003501197 | A | 1/2003 |
| JP | 2003508133 | A | 3/2003 |
| JP | 2005152300 | A | 6/2005 |
| JP | 2005323778 | A | 11/2005 |
| JP | 03965108 | B2 | 8/2007 |
| JP | 2009506839 | A | 2/2009 |
| JP | 2009507617 | A | 2/2009 |
| JP | 2009061173 | A | 3/2009 |
| JP | 2010000360 | A | 1/2010 |
| JP | 2011194126 | A | 10/2011 |
| JP | 2012183232 | A | 9/2012 |
| JP | 2013514150 | A | 4/2013 |
| JP | 2013176465 | A | 9/2013 |
| JP | 2014124475 | A | 7/2014 |
| JP | 2015525609 | A | 9/2015 |
| JP | 2018500054 | A | 1/2018 |
| JP | 2018514350 | A | 6/2018 |
| JP | 2018525197 | A | 9/2018 |
| JP | 2018537229 | A | 12/2018 |
| JP | 2021175686 | A | 11/2021 |
| KR | 10-2015-0131502 | A | 11/2015 |
| KR | 20180053852 | A | 5/2018 |
| WO | WO97/43941 | A1 | 11/1997 |
| WO | WO99/053827 | A1 | 10/1999 |
| WO | WO03/013348 | A1 | 2/2003 |
| WO | WO2005/110199 | A1 | 11/2005 |
| WO | WO2005/110200 | A1 | 11/2005 |
| WO | WO2007/035931 | A2 | 3/2007 |
| WO | WO2008/041809 | A1 | 4/2008 |
| WO | WO2008/122969 | A1 | 10/2008 |
| WO | WO2008/122997 | A1 | 10/2008 |
| WO | WO2009/154192 | A1 | 12/2009 |
| WO | WO2011/018147 | A1 | 2/2011 |
| WO | WO2011/018157 | A1 | 2/2011 |
| WO | WO2011/148172 | A2 | 12/2011 |
| WO | WO2012/054480 | A2 | 4/2012 |
| WO | WO2012/080947 | A1 | 6/2012 |
| WO | WO2012/122288 | A2 | 9/2012 |
| WO | WO2013/132992 | A1 | 9/2013 |
| WO | WO2016/034598 | A1 | 3/2016 |
| WO | WO2016/190324 | A1 | 12/2016 |
| WO | WO2017/041052 | A1 | 3/2017 |
| WO | WO2018/035452 | A1 | 8/2017 |
| WO | WO2019/054867 | A1 | 3/2019 |
| WO | WO2019/160865 | A1 | 8/2019 |
| WO | WO2020/018934 | A1 | 1/2020 |
| WO | WO2020/214221 | A1 | 10/2020 |
| WO | WO2020/237426 | A1 | 12/2020 |
| WO | WO2021/202336 | A1 | 10/2021 |
| WO | WO2021/242884 | A1 | 12/2021 |
| WO | WO2022/051682 | A1 | 3/2022 |
| WO | WO2022/087093 | A1 | 4/2022 |
| WO | WO2022/146939 | A1 | 7/2022 |
| WO | WO2022/159861 | A1 | 7/2022 |
| WO | WO2023/122667 | A1 | 6/2023 |
| WO | WO2023/122767 | A2 | 6/2023 |
| WO | WO2023/133403 | A1 | 7/2023 |
| WO | WO2023/154743 | A2 | 8/2023 |
| WO | WO2023/183952 | A2 | 9/2023 |
| WO | WO2023/205655 | A2 | 10/2023 |
| WO | WO2023/212641 | A2 | 11/2023 |
| WO | WO2023/225520 | A2 | 11/2023 |
| WO | WO2013/184192 | A2 | 12/2023 |
| WO | WO2024/030975 | A2 | 2/2024 |
| WO | WO2024/233497 | A1 | 11/2024 |

OTHER PUBLICATIONS

Devengenzo et al.; U.S. Appl. No. 18/902,906 entitled "Telescoping robot," filed Sep. 30, 2024.

Ferrante et al.; U.S. Appl. No. 18/851,053 entitled "Methods and apparatuses for navigating using a pair of rigidizing devices," filed Sep. 25, 2024.

Tilson et al.; U.S. Appl. No. 18/908,776 entitled "Methods of attaching a rigidizing sheath to an endoscope," filed Oct. 7, 2024.

Dow, Dow white paper: Can you estimate modulus from durometer hardness for silicones: Yes, but you only roughly and you must choose your modulus carefully!; 5 pages; retrieved from the internet (https://www.dow.com/content/dam/doc/documents/en-us/tech-art/11/11-37/11-3716-01-durometer-hardness-for-silicones.pdf) on Jan. 18, 2023.

Bearing Works; PTFE Datasheet; 2 pages; Jan. 21, 2021 retrieved from the internet (https://www.bearingworks.com/uploaded-assets/pdfs/retainers/ptfe-datasheet.pdf) on Nov. 10, 2023.

Entrada® colonic overtube product brochure downloaded from internet http://www.usendoscopy.com/~/media/Files/Documents/Spec-Sheet-International/760358c_entrada_intl_ss_web.pdf Accessed Date: Jun. 5, 2017 (the year of publication is sufficiently earlier than the effective U.S. filing date and any foreign priority date so that the particular month of publication is not in issue) 2009.

(56) References Cited

OTHER PUBLICATIONS

Filip et al.; Design, Implementation, and Testing of a miniature self-stabilizing capsule endoscope with wireless image transmission capabilities; Intl. Journal "Information Technologies & Knowledge"; 5(1); downloaded from http://www.foibg.com/ijitk/ijitk-vol05/ijitk05-1-p01.pdf on Jul. 28, 2016; (the year of publication is sufficiently earlier than the effective U.S. filing date and any foreign priority date so that the particular month of publication is not in issue) 2011.
Loeve et al.; Endoscope Shaft-Rigidity Control Mechanism: "Forguide"; IEEE Trans. On Biomed. Eng.; 59(2); pp. 542-551; Feb. 2012.
Loeve et al.; Vacuum packed particles as flexible endoscope guides with controllable rigidity; Granular Matter; 12(6); pp. 543-554; Jun. 24, 2010.
Mayinger et al.; Disposable-sheath, flexible gastroscope system versus standard gastroscopes: a prospective, randomized trial; Gastrointestinal Endoscopy; 50(4); pp. 461-467; Oct. 1999.
Mayinger et al.; Disposable protection for flexible gastroenterologic endoscopy: prospective comparative evaluation of a new gastroscopy system (Endosheath) compared to the standard fiberglass gastroscope; (English Abstract Only); Zeitschrift Fur Gastrenterologia; 36(6); pp. 501-507; Jun. 1998 (Eng Abs only).
Ofstead et al.; A systematic review of disposable sheath use during flexible endoscopy; AORN Journal; 109(6); pp. 757-771; Jun. 2019.
Rothstein et al.; Disposable, sheathed, flexible sigmoidoscopy: a prospective, multicenter, randomized trial; Gastrointestinal Endoscopy; 41(6); pp. 566-572; Jun. 1995.
Sardinha et al.; Efficiency and productivity of a sheathed fiberoptic sigmoidoscope compared with a conventional sigmoidoscope; Diseases of the Colon and Rectum; 40(10); pp. 1248-1253; Oct. 1997.
Shah et al.; Magnetic Imaging of Colonoscopy: An Audit of Looping, Accuracy and Ancillary maneuvers; Gastrointest. Endosc.; 52(1); pp. 1-8; Jul. 1, 2000.
Simi et al.; Design, Fabrication, and Testing of a Capsule With Hybrid Locomotion for Gastrointestinal Tract Exploration; IEEE/ASME Trans on Mechatronics; 15(2); pp. 170-x; Apr. 2010.
Valdastri et al.; Advanced Technologies for Gastrointestinal Endoscopy; Annu. Rev. Biomed. Eng.; 14; pp. 397-429; May 2012.
Zhao et al.; Development of a variable stiffness over tube based on low-melting-point-alloy for endoscopic surgery; J. Med. Devices; 10(2); 8 pages; May 12, 2016.
Tilson et al.; U.S. Appl. No. 18/592,516 entitled "Device and method for enhanced visualization of the small intestine," filed Feb. 29, 2024.
Tilson et al.; U.S. Appl. No. 18/751,188 entitled "Rigidzing overtube," filed Jun. 21, 2024.
Lopez et al.; U.S. Appl. No. 18/723,414 entitled "Methods and apparatuses for reducing curvature of a colon," filed Jun. 21, 2024.
Gomes et al.; U.S. Appl. No. 18/723,413 entitled "Obturator with stiff distal cannula engagement region," filed Jun. 21, 2024.
Morris et al.; U.S. Appl. No. 18/727,032 entitled "Reconfigurable rigidizing structures," filed Jul. 5, 2024.
Tilson et al.; U.S. Appl. No. 18/780,429 entitled "Device for endoscopic advancement through the small intestine," filed Jul. 22, 2024.
Eisler et al.; U.S. Appl. No. 18/852,419 entitled "Rigidizing aspiration systems and methods," filed Sep. 27, 2024.
Tilson et al.; U.S. Appl. No. 18/809,322 entitled "Rigidizing overtube," filed Aug. 19, 2024.
Tilson et al.; U.S. Appl. No. 18/810,458 entitled "Rigidizing overtube," filed Aug. 20, 2024.
Gomes et al.; U.S. Appl. No. 18/837,186 entitled "Dynamically rigidizing composite medical structure," filed Aug. 8, 2024.
Tilson et al.; U.S. Appl. No. 18/858,743 entitled "Managing and manipulating a long length robotic endoscope," filed Oct. 21, 2024.
Gomes et al.; U.S. Appl. No. 18/806,692 entitled "Devices and methods to prevent inadvertent motion of dynamically rigidizing apparatuses," filed Aug. 15, 2024.
Tilson et al.; U.S. Appl. No. 18/867,004 entitled "External working channels for endoscopic devices," filed Nov. 18, 2024.
Tilson et al.; U.S. Appl. No. 19/100,929 entitled "Dynamic rigidization methods and apparatuses," filed Feb. 3, 2025.

* cited by examiner (flexible)

(rigid)

(flexible)

(rigid)

(flexible)

(rigid)

(flexible)

(rigid)

(flexible)

PRESSURE RIGIDIZATION APPARATUSES AND METHODS

CLAIM OF PRIORITY

This patent application claims priority to U.S. Provisional Patent Application No. 63/581,266, titled "PRESSURE RIGIDIZATION APPARATUSES AND METHODS," filed on Sep. 7, 2023, and herein incorporated by reference in its entirety.

BACKGROUND

Rigidizing devices that may rapidly transition between a compliant and flexible configuration and a more rigid configuration may allow access and treatment options that were previously not possible. For example, dynamically rigidizing overtubes and endoscopes have been described and utilized to reduce risks associated with looping and to facilitate medical procedures, including colonoscopy. In the flexible state, such devices may be soft and pliable, but in the rigid state, may become many times stiffer. In some cases, the transition between flexible and rigid states ("Dynamic Rigidization") may be actuated by the application of positive and/or negative pressure.

Dynamically rigidizing medical devices may include elongate, sometimes tubular structures that include catheters, sheaths, scopes (e.g., endoscopes), wires, overtubes, cannulas, trocars or laparoscopic instruments. The devices can function as a separate add-on device or can be integrated into the body of devices. The devices are inserted into the body so as to access regions within the body, including in some cases forming passages for additional diagnostic and therapeutic medical devices.

When operating dynamically rigidizing apparatuses, and in particular, pressure-actuated (e.g., positive pressure and/or negative pressure, typically either liquid or in gas phase) apparatuses, it may be particularly beneficial to transition quickly between the flexible and rigid states. Although such tools may provide safe, efficient, and precise access to otherwise difficult to reach anatomical locations, it would be beneficial to provide various improvements to rigidizable devices, including improvements that allow the devices to be safer, faster, offer a wider range of flexibility and stiffness, thinner walls, enhance manufacturability, reduced set-up and tear-down time and complexity, reduced environmental impact and landfill, and the ability to function as higher performance combined systems.

Described herein are apparatuses and methods that may address these needs.

SUMMARY OF THE DISCLOSURE

Described herein are methods and apparatuses for improving the operation and safety of dynamically rigidizing devices, and in particular, for improving the operation and safety of pressure-actuated dynamically rigidizing devices. For example, described herein are apparatuses (e.g., systems and devices, including sub-systems) and methods for controlling the applied pressure, apparatuses and methods for reducing or eliminating risks of cross-contamination, apparatuses and methods for pressure relief when using a rigidizing apparatus, and apparatuses and methods for routing pressure tubing that may be integrated with a rigidizing apparatus.

For example, described herein are apparatuses, including sub-systems, for regulating and/or controlling the application of fluid pressure, and in particular air pressure, to rigidize or de-rigidize a device. These apparatuses may be referred to for convenience as rigidizing pressure control systems or sub-systems, and may be configured to be used with a rigidizing device and/or may be configured to be integrated with the rigidizing device. Any of the rigidizing pressure control systems/sub-systems described herein may include a pressure source or may be configured to be coupled to a pressure source. For example, the pressure source may include a pump (pressure pump), cannister or reservoir of pressurized fluid (e.g., pressurized air or other gas), or the like. The pressure source may be a stand-alone pressure source or a facility integrated wall pressure source (e.g., centralize air pressure line). The rigidizing pressure control systems/sub-systems described herein may be configured to apply positive pressure. Alternatively, in some cases these rigidizing pressure control systems/sub-systems may be configured to operate with negative pressure (suction). Alternatively, in some cases these pressure control systems may be configured to operate with both positive and negative pressure.

In general the rigidizing pressure control systems/sub-systems described herein may be configured to be normally closed or normally opened. Normally closed rigidizing pressure control systems/sub-systems may provide a pulse of pressure (e.g., a bolus of pressure), typically positive pressure (but also possibly negative pressure) to the rigidizing device. The pulse of pressure may be a pulse of pressurized fluid (in particular, pressurized air). The pulse of pressure may be relatively high pressure (e.g., between 2-40 atmospheres, e.g., between 2 and 40 atmospheres, between 2-15 atmospheres, between 2-10 atmospheres, etc.). It may be full vacuum or partial vacuum. In order to transition the rigidizing device between the flexible and rigid states, the rigidizing device and rigidizing pressure control system/sub-system may be configured to hold the pressure within the rigidizing device in passive operation, e.g., within a bladder/compression layer(s) or region(s). For example, the pressure pathway from the rigidizing pressure control systems/sub-systems to the rigidizing device may be sealed when engaged, to minimize or prevent leakage. The rigidizing pressure control systems/sub-systems may be configured to controllably release, e.g., open or vent, to de-pressurize the rigidizing device and transition between rigid and flexible configurations. In some examples, the rigidizing pressure control systems/sub-systems may also or alternatively be configured to apply negative pressure. In some examples the rigidizing pressure control system/sub-system may be configured to monitor the pressure within the rigidizing pressure control system/sub-system and/or the rigidizing device in order to apply one or more additional pulses of pressure to maintain the rigidity of the rigidizing device with a predetermined range. Any of these apparatuses may include one or more pressure sensors to determine the pressure within the rigidizing pressure control system/sub-system and/or the rigidizing device (e.g., the bladder or compression layer(s)).

A normally open rigidizing pressure control system/sub-system may be configured to apply pressure at a level (which may be adjustable, and may be based on feedback from one or more pressure sensors) to control the state, e.g., to rigidizing and/or de-rigidize the rigidizing device.

Any of the normally closed rigidizing pressure control system/subsystem may include a pressure reservoir (e.g., a tank) for holding the pressurized fluid to be applied. The rigidizing pressure control systems/sub-systems may be referred to as system for rigidizing an elongate rigidizing device and may include: a pressure line configured to couple at a distal end to a pressure inlet of the elongate rigidizing device; a pressure sensor configured to detect pressure within the pressure line; a vent valve proximal to the pressure sensor and in fluid communication with the pressure line; a supply valve proximal to the vent valve and pressure sensor and in fluid communication with the pressure line; a pressure controller proximal to the supply valve and configured to couple to a source of pressurized fluid and to open the supply valve to apply a pulse of pressurized fluid through the pressure line to rigidize the elongate rigidizing device. The pressure line may include tubing or other channels that may pass the pressurized fluid (e.g., air) from the rigidizing pressure control system/sub-system to the rigidizing device, and may include one or more connectors for coupling to the pressure inlet of the rigidizing device. The connectors may be any appropriate connector (e.g., a pressure fitting) in order to securely couple between the pressure inlet and the pressure line of the rigidizing pressure control system/sub-system.

The pressure sensor may be any appropriate pressure sensor, including mechanical (spring-based, deflection/expansion based, etc.) pressure sensors, piezoelectric pressure sensors, capacitive pressure sensors, bourdon tube pressure sensors, etc. The rigidizing pressure control systems/sub-systems may include multiple pressure sensors, including redundant pressure sensors. The pressure sensor may be fluidly connected at any appropriate region of the pathway in fluid communication with the rigidizing device, including in fluid communication with the pressure line, pressure inlet, etc. The pressure sensor(s) may communicate with (input to) the pressure controller.

The rigidizing pressure control systems/sub-systems described herein may generally include one or more valves, including a vent valve (or valves) for releasing/venting pressure to atmosphere from the rigidizing device and/or pressure line. Any appropriate valve may be used, particularly valves that may be controlled by the pressure controller. Examples of pressure valves may include, but are not limited to solenoid valves, motorized valves, etc. Fast (e.g., high-speed) valves may be preferred.

Any of these apparatuses (e.g., rigidizing pressure control systems/sub-systems) may be configured so that the pressure controller is configured to apply the pulse of pressure for 1 second or less (e.g., for 0.9 seconds or less, 0.8 seconds or less, 0.7 seconds or less, 0.6 seconds or less, 0.5 seconds or less, 0.4 seconds or less, etc.). The pulse may be defined by the on time (the time in which the pulse is applied, e.g., 1 second or less) and the pressure applied by the rigidizing pressure control system/sub-system, which may be controlled by the controller and/or a pressure regulator. In general, the pressure applied during the pulse may be between 1.5 atmospheres and 40 atmospheres (e.g., between 2 atmospheres and 15 atmospheres, between 2 atmospheres and 10 atmospheres, between 2.5 atmospheres and 15 atmospheres, between 3 atmospheres and 40 atmospheres, etc.). For example, the pressure controller may be configured to apply the pulse of pressurized fluid at between 2 atmospheres and 10 atmospheres. In any of these examples, the apparatus may be configured to apply a single pulse of pressure (rigidizing pulse) to rigidize the rigidizing device. The use of a single, relatively high-pressure pulse may rapidly (nearly instantaneously) transition the rigidizing device between flexible and rigid configuration. Alternatively, in some examples multiple pulses of pressure (rigidizing pulses) may be applied to transition the rigidizing device between flexible and rigid configurations. Multiple rigidizing pulses may prevent over-rigidizing of the rigidizing device.

In general, the pressure controller may include a control circuitry. The control circuitry may include one or more processors, one or more memories, one or more clocks/timers, etc. The control circuitry may be redundant, including configurations in which both control circuit elements must 'agree' for an operation to take place. Similar redundancies and 'agreements' may be applied to other parts of the system, including pressure sensors and valve actuations. The control circuitry may be configured to detect a drop in pressure from the one or more pressure sensors below a threshold and may be configured to apply one or more additional pulses of pressure through the pressure line, e.g., to maintain the pressure within a predetermined range. In some examples these maintenance pressure pulses may be shorter and/or different pressures than the initial pulse(s). For example, the one or more additional pulses of pressure may be less than, e.g., 200 ms (e.g., less than 150 ms, less than 100 ms, less than 75 ms, less than 50 ms, less than 30 ms, etc.) long.

In any of these examples the control circuitry may be configured to open the vent valve(s) to de-rigidize the elongate rigidizing device. In some examples the vent valve may be connected to atmosphere (e.g., the surrounding environment). As described in some examples herein, the vent valve location may be controlled to prevent cross-contamination. In some examples the vent valve may open to a source of negative pressure so that the de-pressurization process is more actively driven.

In general, the control circuitry may be configured to determine a leak rate and to trigger an alert if the leak rate exceeds a leak threshold while in the rigid state. For example, if one or more of the pressure sensors detects the pressure falling below a threshold, the apparatus may be configured to trigger an alert (visible, audible, tactile, etc.). This alert may result in the application of one or more additional pulses of pressure to maintain the pressure. Alternatively, in some cases the alert may lead to other states, including the halting of the procedure. Multiple types of alerts may be emitted depending on the speed with which the pressure is falling, e.g., indicating a "slow" leak or a "fast" leak; a slow leak (e.g., less than 0.3 atm/min, 0.2 atm/min, 0.1 atm/min, 0.05 atm/min, 0.01 atm/min, etc.) may result in additional pressure pulses, whereas more rapid leaks (greater than about 0.01 atm/min, greater than 0.05 atm/min, greater than 0.1 atm/min, greater than 0.2 atm/min, greater than 0.3 atm/min, greater than 0.5 atm/min, etc.) may result in stopping the procedure, and depressurizing the apparatus.

As mentioned, any of the rigidizing pressure control systems/sub-systems described herein may include a source of pressurized fluid and/or a pressurized reservoir. The pressurized reservoir may include a tank, chamber, etc. of pressurized fluid that may be used to apply the pulse(s). The pressure controller may be configured to maintain the pressurized reservoir within a pressure level appropriate for the application of the one or more pressure pulses.

Any appropriate pressurized fluid may be used, including gases and liquids. In particular, the pressurized fluid may be a gas, such as air, nitrogen, carbon dioxide, etc.

The supply valve may be maintained closed and may be configured to be opened by the pressure controller. The supply valve may be in fluid communication with the pressure line and proximal to the vent and pressure sensor. In some examples the supply valve may open/close the fluid communication between the source of pressurized fluid (e.g., the pressure source and/or reservoir) and the fluid line.

Any of the rigidizing pressure control systems/sub-systems described herein may be used with one rigidizing device or may be used with multiple rigidizing devices. In some examples multiple rigidizing pressure control systems/sub-systems may be used together, and may be collectively controlled by a system controller that is separate from, and communicates with/commands the pressure controller of each rigidizing pressure control systems/sub-systems. In some examples a single rigidizing pressure control system/sub-system may be configured to control the pressure to multiple rigidizing devices, including nested rigidizing devices. For example, a rigidizing pressure control system/sub-system may independently control the rigidization/de-rigidization of two or more rigidizing devices. For example, any of these systems may include a second pressure line configured to couple to a second elongate rigidizing device, a second pressure sensor in fluid communication with a distal end region of the second pressure line, a second vent valve proximal to the second pressure sensor, and a second supply valve proximal to the second vent valve and in fluid communication with the second pressure line, wherein the pressure controller comprises a pressure manifold and is configured to selectively apply one or more pulses of pressurized fluid through the pressure line or the second pressurized line.

The rigidizing pressure control systems/sub-systems described herein are particularly effective at rapidly applying a pulse of pressure to rigidizing one (or more) rigidizing devices. Although the pulse of pressure may be applied as a relatively high pressure (e.g., up to 10 atmospheres, up to 12 atmospheres, up to 12.5 atmospheres, up to 14 atmospheres, up to 15 atmospheres, up to 17.5 atmospheres, up to 20 atmospheres, up to 22.5 atmospheres, up to 25 atmospheres, up to 27.5 atmospheres, up to 30 atmospheres, etc.) the final pressure achieved in the rigidizing device will be lower, as this pressure is distributed along the length of the bladder/compression layer(s) within the rigidizing device. However, the application of high pressure (potentially higher than the desired baseline resultant pressure) may result in more rapid rigidization.

For example, a system for rigidizing an elongate rigidizing device may include: a pressure line configured to couple at a distal end to a pressure inlet of an elongate rigidizing device, wherein the elongate rigidizing device is configured to be rigidized from a flexible configuration to a rigid configuration; a pressure sensor configured to detect pressure within the pressure line; a vent valve in fluid communication with the pressure line and proximal to the pressure sensor; a supply valve in fluid communication with the pressure line and proximal to the vent and pressure sensor; a pressure controller in communication with the pressure sensor, proximal to the supply valve, and configured to couple to a source of pressurized fluid and to open the supply valve to apply a pulse of pressurized fluid through the pressure line to rigidize the elongate rigidizing device, wherein the pulse of pressure is applied for less than 1 second, and wherein the pulse of pressurized fluid is pressured to between about 2 and 10 atmospheres.

Also described herein are methods of applying one or more pulses of pressure to control rigidization of a rigidizing device, including using any of these apparatuses to control the rigidization and/or de-rigidization of the rigidizing device. For example, described herein are methods of controlling rigidization of an elongate rigidizing device that may include: applying a pulse of pressurized fluid through a pressure line to rigidize the elongate rigidizing device after receiving a command to rigidize the elongate rigidization device, wherein the pulse of pressure is applied for less than 1 second; maintaining the pressure within the rigidizing device by closing one or more valves; and releasing the pressure within the rigidizing device by opening the one or more valves after receiving a command to de-rigidize the elongate rigidizing device. Thus, any of these methods may include coupling a pressure line to an inlet of the elongate rigidizing device.

The pulse of pressurized fluid may be applied by opening a valve (e.g., supply valve) to allow fluid communication between the source of pressurized fluid, which may be a reservoir, and the pressure inlet of the rigidizing device. The quick-opening (e.g., less than 100 ms, less than 75 ms, less than 50 ms, less than 10 ms) valve may remain open for the pulse duration and then close. The resulting bolus of high-pressure fluid may then pressurize the rigidizing device, driving the bladder/compression layer(s) against the rigidizing layer(s) to rigidize the device. In general, as mentioned above, the pressurized fluid may be pressured to 3 atmospheres or more (e.g., 5 atmospheres or more, 6 atmospheres or more, 7 atmospheres or more, 8 atmospheres or more, 10 atmospheres or more, 12 atmospheres or more, 14 atmospheres or more, 15 atmospheres or more, 16 atmospheres or more, 17 atmospheres or more, 18 atmospheres or more, 20 atmospheres or more, 25 atmospheres or more, 30 atmospheres or more, 40 atmospheres or more, etc.), such as between about 2 and 10 atmospheres, etc. In contrast, in the un-rigidized configuration the bladder/compression layer(s) of the rigidizing device may be relatively unpressurised, and may have been vented to atmosphere to de-rigidize. Thus the rapid, relatively large pressure differential may result in a very rapid rigidization.

Once rigidized, following the application of the pulse of pressure, the normally-closed apparatuses described herein may maintain the pressure within the rigidizing device. In some cases the pressure may be maintained through the pressure line and to the inlet valve. Alternatively or additionally, the pressure may be maintained (e.g., by closing one or more valves) from the inlet valve of the rigidizing device. The sealed pathway may maintain the pressure. Any of these methods and apparatuses may also include detecting a drop in pressure within the elongate rigidizing device and applying one or more additional pulses of pressure through the pressure line. For example, the pressure controller may monitor the pressure within the rigidizing device using one or more sensors within the rigidizing device and/or within the pressure line or in fluid communication with the bladder/compression layers(s). Supplemental pulses of pressure may be of the same pressure and duration as the rigidizing pulse(s) or they may be smaller in pressure and/or duration. For example, the one or more additional pulses of pressure may be less than 30 ms long. The supplemental pressure pulses may be the same pressure as the rigidizing pulse(s).

The methods and apparatuses described herein may be configured to adjust the pressure of the pulse of pressure to adjust the time required to rigidize the elongate rigidizing device. For example, higher pressure pulses may result in faster rigidization. In some cases, slower rigidization may be acceptable, and a lower pressure pulse (e.g., between 2-5 atmospheres) may be acceptable; however, in some cases a faster rigidization may be desired, and/or may be selected and therefore a higher pressure pulse (e.g., greater than 4 atmospheres, greater than 5 atmospheres, greater than 6 atmospheres, greater than 7 atmospheres, etc.) may be used.

The duration of the pulse may be relatively fast (e.g., one second or shorter, 900 ms or shorter, 800 ms or shorter, 700 ms or shorter, 600 ms or shorter, 500 ms or shorter, 400 ms or shorter, 300 ms or shorter, 200 ms or shorter, 100 ms or shorter, 20 ms or shorter, etc. In some cases the duration of the pressure pulse may be adjustable. The duration of the pressure pulse may be adjusted based on the total volume of the pressure pathway, e.g., to achieve a final pressure that is sufficiently high to rigidize the rigidizing device.

As mentioned above, the fluid used to apply the pulse of pressure may be any appropriate fluid, including a liquid and in particular may be gas (e.g., air, nitrogen, $CO_2$, etc.). For example, the pulse of pressurized fluid may comprise a pulse of pressurized air.

Also described herein are methods and apparatuses for reducing, minimizing, or eliminating cross-contamination between the rigidizing device and the rigidizing pressure control systems or sub-systems. The rigidizing apparatuses (devices and systems) described herein may be used as part of a sterile procedure (e.g., within a sterile field), so that the rigidizing device may be kept sterile for use within a sterile field, while the rigidizing pressure control system or sub-system is kept clean and is maintained outside of the sterile field. Alternatively, in some examples both the rigidizing device and the rigidizing pressure control systems or sub-systems may be used in a clean, but non-sterile environment. In either case, the apparatus may be configured to prevent cross-contamination from the rigidizing device to the rigidizing pressure control systems or sub-systems. In particular, material (including fluid used to pressurize the apparatus) may be vented or removed distal from the rigidizing pressure control systems or sub-systems to prevent cross-contamination.

For example, described herein are systems for rigidizing an elongate rigidizing device that prevents cross-contamination. The system may include a reusable pressure controller and an interface sub-system. The reusable pressure controller may include: a pressure line; one or more supply valves in fluid communication with the pressure line; and a pressure controller proximal to the supply valve and configured to couple to a source of pressurized fluid and to open the supply valve to apply pressurized fluid through the pressure line to rigidize the elongate rigidizing device. The interface sub-system may include: a handle body integrated with, or configured to couple to, a proximal end of the elongate rigidizing device; a pressure inlet configured to couple to the pressure line; a check valve in fluid communication with a rigidizing pressure inlet of the elongate rigidizing device, wherein the check valve is configured to prevent back flow from the elongate rigidizing device to the pressure outlet; a vent on the handle body; a vent valve connecting the pressure inlet to the check valve and connecting the vent to the rigidizing pressure inlet, wherein the vent valve has at least two states, a first state in which the pressure inlet is fluidly connected to the check valve and the vent is not fluidly connected to the rigidizing pressure inlet, and a second state in which the vent is fluidly connected to the rigidizing pressure inlet and the pressure inlet is not fluidly connected to the check valve, further wherein the vent valve is configured to transition from the second state to the first state when pressure from the pressure inlet exceeds a threshold.

The reusable pressure controller may be referred to herein as a rigidizing pressure control system or sub-system, and may be any of the rigidizing pressure control systems or sub-systems described herein. The interface sub-system may be a rigidizing device or may be configured to couple to a rigidizing device.

In some examples the interface sub-system may include a housing. The housing may be configured to couple to the rigidizing device, including a handle of the rigidizing device. The housing may be configured as a handle body. For example, the interface sub-system may be configured to be integrated into the proximal end of the elongate rigidizing device.

In any of the interface sub-systems described herein the vent valve may be biased in the second configuration. The vent valve may be biased by a spring.

Any of these apparatuses may also include a de-rigidizing valve on the interface sub-system. The de-rigidizing valve may be configured to open to allow venting of pressure from the rigidizing pressure inlet out of the valve.

The pressure controller may receive input from one or more pressure sensors on the interface sub-system. In some examples the pressure controller is configured to apply a pulse of pressurized fluid through the pressure line. As described above, the pressure controller may be configured to apply the pulse of pressure, e.g., for less than 1 second and/or may be configured to apply the pulse of pressurized fluid at between 2 atmospheres and 10 atmospheres.

Also described herein are methods of controlling rigidization of an elongate rigidizing device. For example, a method may include: coupling an interface sub-system to a reusable pressure controller, wherein the reusable pressure controller is separated from the interface sub-system by a pressure line and wherein the interface sub-system is integral with or coupled to a handle portion of the elongate rigidizing device; applying a pulse of positive pressure from the reusable pressure controller to the elongate rigidizing device to rigidize the elongate rigidization device from a flexible state to a rigid state; venting the pressure from the elongate rigidization device to de-rigidize the elongate rigidization device though a vent on the handle, wherein the pressure is vented within the sterile filed. The reusable pressure controller may be outside of a sterile field and the interface sub-system is within the sterile filed.

Also described herein are apparatuses including an external pressure relief or release. An external pressure relief may include a channel or passage for release of pressure from a region around all or a portion of the rigidizing device when the rigidizing device is inserted into the body, e.g., into a colon or other region of the body. The pressure relief may be a separate element, e.g., tube, catheter, etc. or it may be coupled to or integrated into the rigidizing device. For example, the pressure relief may be a part of a sleeve or overtube that engages with the rigidizing member. In some cases the rigidizing member may include an external channel to engage with the pressure relief member (e.g., tube). In some cases the rigidizing device may include an internal channel having lateral exits or access regions that allow fluid communication between the region of the device outside of the rigidizing device and the pressure relief lumen transporting gas away from the region of the lumen around all or a portion of the rigidizing device when the rigidizing device is inserted into the body.

For example, described herein are rigidizing apparatuses configured to provide a relief path for pressure outside of a rigidizing apparatus, the apparatus comprising: a rigidizing device configured to transition between a flexible configuration and a rigid configuration based on an applied pressure; and a pressure relief channel coupled to the rigidizing device, wherein the pressure relief channel is configured to vent pressure from outside of the rigidizing device and out of a pressure relief valve at a proximal end of the pressure relief channel.

In some examples, the pressure relief channel may include an elongate flexible tube. The rigidizing apparatus may include one or more couplers coupling the pressure relief channel to the rigidizing device.

The pressure relief channel may be configured to slide relative to the rigidizing device. Alternatively in some examples the pressure relief channel may be fixed relative to the rigidizing device. The pressure relief channel may include a stop on an outer surface of the pressure relief channel configured to limit axial movement of the pressure relief channel relative to the elongate rigidizing device. In some examples the pressure relief channel comprises a one-way valve preventing passage from the proximal to the distal end of the pressure relief channel.

A distal end region of the pressure relief channel may include one or more (e.g., a plurality of) openings into a central lumen of the pressure relief channel.

The pressure relief channel may be configured to pass through a portion of the elongate rigidizing device.

Also described herein are apparatuses and method for controlling routing a pressure line to a rigidizing device while allowing roll of the rigidizing device. In some examples the pressuring apparatuses may be configured to controllably roll (rotate, e.g., clockwise and counterclockwise) relative to the proximal end of the rigidizing device. In addition to roll, the rigidizing device may also be configured to be steered by bending in one or more degrees of freedom. Roll in particular may be challenging when routing a pressure line to apply positive and/or negative pressure into one or more bladder/compression layer(s) used for rigidizing these apparatuses. Rolling of the rigidizing device relative to the pressure line and rigidizing pressure control system/sub-system may result in added friction, as the pressure line may pull and may also require additional space in the proximal end region to allow for movement. Thus, described herein are tube router devices that may be included as part of a rigidizing device or for use with an apparatus including a rigidizing device. A tubing router device may be configured to control the routing of a pressure line (e.g., tubing) while allowing rotation of the inlet to which the pressure line is fluidly coupled to rotate relative to the tubing router device.

A tubing router (e.g., a tubing router device) may include: a first spool; an input drivetrain member driving rotation of the first spool; an idler drivetrain member rigidly coupled to the first spool and engaging with the input drivetrain member; a second spool configure to rotate with the first spool; an output drivetrain member rigidly coupled to the second spool and driven by the idler drivetrain member; a tubing line configured to wind around and between the first spool and the second spool as the input drivetrain member is driven in a clockwise or a counterclockwise rotation; a fluid input coupled to the first spool and in fluid communication with a lumen of the tubing line; and a fluid output coupled to the second spool and in fluid communication with the lumen of the tubing line.

In any of these devices, the drivetrain member may be a mechanism (e.g., gears, cable, belt, etc.) that could be used to constrain the spools relative to each other. Thus, the input drivetrain member, the idler drivetrain member and the output drivetrain member may be configured to engage with each other to move the first and second spools and to transfer the tube between the two. For example, the idler drivetrain member, the output drivetrain member and the input drivetrain member may be configured as one or more of: a gear train, a friction wheel mechanism, etc. Although the examples described herein may show the use of gears as part of the tubing router device, it should be understood that these devices may use any appropriate mechanism.

For example a tubing router device may include: a first spool; an input gear driving rotation of the first spool; an idler gear rigidly coupled to the first spool and engaging with the input gear; a second spool configure to rotate with the first spool; an output gear coupled (sometimes rigidly) to the second spool and driven by the idler gear; a tubing line configured to wind around and between the first spool and the second spool as the input gear is driven in a clockwise or a counterclockwise rotation; a fluid input coupled to the first spool and in fluid communication with a lumen of the tubing line; and a fluid output coupled to the second spool and in fluid communication with the lumen of the tubing line.

In general, the spools are configured to rotate relative to each other in opposite directions so that a linear tubing line may alternately wind and unwind as the pressure port (e.g., on a rigidizing device that is rigidly coupled to one of the spools) rolls in either the clockwise or anti-clockwise direction. The spools may be adjacent to each other, and/or arranged in parallel. tubing line may be a length of flexible tubing that is fluidly coupled to the first spool (e.g., to the fluid input port on the first spool) and is also fluidly coupled to the second spool (e.g., to the fluid output port) on the second spool. The spools may each be coupled to gears that engage with each other. For example, the first spool may be coupled to an input gear, while the second spool may be coupled to the idler gear. In this configuration the spools may rotate in opposite directions. In some examples a secondary idler gear may be used between the input gear and the idler gear and the first and second spools may rotate in the same direction. In either case, the tubing may be transferred smoothly between the two spools without interrupting the fluid pathway through the tubing connecting the fluid inlet, which may be coupled in fluid communication with the fluid line of a rigidizing pressure control systems or subsystems, and the fluid outlet, which may be coupled in fluid communication with the pressure inlet of a rigidizing device.

In any of these examples a first end of the tubing line may be coupled to the first spool so that the fluid input is in fluid communication with the lumen of the tubing line. The second end of the tubing line may be coupled to the fluid output through the second spool. The proximal end of the rigidizing device (e.g., overtube, catheter, etc.) may be rigidly coupled to the second spool so that second spool and the rigidizing device may rotate together and may be automatically (e.g. robotically) and/or manually rotated.

Any of these apparatuses may include a limiter limiting rotation of the first spool and the second spool in the clockwise and the counterclockwise directions. The limiter may limit the roll (either or both clockwise and counterclockwise) of the spools and therefore the rigidizing device.

The rotation of the first and second spools may be coordinated by the gearing and radius of the spools so that the rate that the tubing line unspools from one spool matches the rate at which the tubing line spools onto the other spool. In some cases the gearing ratio of the first spool and the second spool is 1:1. For example, the idler gear and the output gear have a gear ratio of 1:1. In some cases the ratio may be different (e.g., between 5:1 and 1:5) but the pitch of the spooling and/or the diameter of the spools may be adjusted so that the rate of spooling and unspooling between the two spools is equivalent, preventing tension on the tubing line and preventing the tubing line from becoming overly loose. For example, the idler gear and the output gear may have a gear ratio of between 3:1 and 1:3. Any appropriate tubing may be used. In some examples the tubing comprises an elastomeric tubing. Any of these apparatuses may be configured to use multiple lines of tubing, e.g., in parallel, concentrically, or in series. For example, two (e.g., parallel) tubing lines (e.g., lengths of tubing) could have increased utility as compared to a single tubing line. In some examples an additional tubing can be utilized by having a secondary line adjacent, such that it spools on or off in tandem. In some examples an additional length of tubing can be concentrically inside of the main tubing line ('tube in tube'), such that they move in unison, but are attached separately to their respective fluid paths at their ends, such that two fluid paths can be created instead of one, all within one outer tubing profile.

In any of these examples, the fluid input may comprise a connector configured to couple to a source of pressurized fluid. The fluid output may comprise a connector configured to engage with a pressure inlet of an elongate steerable rigidizing device.

As mentioned, in some examples the second spool may be configured to couple with the elongate steerable rigidizing device so that rotation of the second spool results in roll of the elongate steerable rigidizing device while keeping the connector engaged with the pressure inlet.

The tubing router devices (tubing router assemblies) described herein may be used in other apparatuses as well, not limited to rigidizing devices. Any system in which fluid (pressurized or otherwise) must be delivered to a structure that can roll may incorporate as tubing router assembly as described herein. As described herein, a tubing router device may be particularly well suited for use with the rigidizing devices.

For example, a steerable rigidizing system may include: an elongate body; a rigidizing layer within the elongate body; a compression layer configured to be pushed against the rigidizing layer by a pressure differential to rigidize the rigidizing layer; a pressure inlet in fluid communication with the compression layer; and a tubing router comprising: a first spool; an input gear driving rotation of the first spool; an idler gear coupled to the first spool and engaging with the input gear; a second spool configure to rotate with the first spool; an output gear coupled to the second spool and driven by the idler gear; a tubing line configured to wind around and between the first spool and the second spool as the input gear is driven in a clockwise or a counterclockwise rotation; a fluid input coupled to the first spool and in fluid communication with a lumen of the tubing line; and a fluid output coupled to the second spool and in fluid communication with the lumen of the tubing line, wherein the fluid output if also in fluid communication with the pressure inlet, wherein the second spool is coupled with the elongate body so that rotation of the second spool results in roll of the elongate body while keeping the connector engaged with the pressure inlet.

Any of these apparatuses (e.g., systems) may include a proximal handle at a proximal end of the elongate body, wherein the tubing router is within the proximal handle. For example, these apparatuses may include one or more steering tendons configured to steer a distal end region of the elongate flexible body, which may be part of the rigidizing device. These apparatuses may include one or more tendon drivers configured to drive movement of the one or more steering tendons, wherein the one or more tendon drivers are within the proximal handle.

In general, any of the apparatuses and methods described herein may be configured to rigidize and/or de-rigidize one or more dynamically rigidizing devices using a pulse (or in some examples, pulses) of pressurized fluid, which may be referred to equivalently herein as a rigidization medium. The pressurized fluid may water, saline, etc., although the preferred rigidization medium may be a compressible fluid, including a gas, such as, but not limited to, air, carbon dioxide ($CO_2$), nitrogen, etc. In any of these apparatuses and methods, the pulse of pressure may be configured as a high pressure pulse, having a very rapid on and off time, e.g., achieved by operating a fast valve or valves. The pulse of pressure may have a rise time of 100 milliseconds or faster (e.g., 50 milliseconds or faster, 25 milliseconds or faster, 10 milliseconds or faster, 5 milliseconds or faster, 1 millisecond or faster, etc.). In any of these apparatuses and methods, the pulse of pressure (high pressure pulse) applied to rigidize the device may be configured to have a pressure that is greater than the target rigidizing pressure. Thus, the applied pulse of pressure may be overpressurizing as compared to the target rigidizing pressure. For example, a rigidizing device may have a target rigidization pressure of 4 atmospheres (e.g. 4 atm, 5 atm, 6 atm, 7 atm, 8 atm, etc.), and the rigidizing pulse of pressure may be set to be greater than the target rigidization pressure, e.g., 110% or more, 115% or more, 120% or more, 125% or more, 130% or more, 135% or more, 140% or more, 145% or more, 150% or more, 200% or more, 400% or more, etc. of the target rigidization pressure. The use of a rapid on and/or off (e.g., transient), overpressurizing pulse may result in an extremely fast rigidization of the dynamically rigidizing device that is both safe and effective. The speed with which the rigidizing device is rigidized by the transient (e.g. rapid) pulse may depend on how overpressurized the applied pulse is as compared to the target rigidization pressure; in general, the more overpressurized the applied pulse, the faster the rigidization that may be achieved. In general, the target pressure for rigidizing the device may be the optimal (or highest) safe pressure for rigidizing the device, and/or the target pressure for achieving a desired rigidity. In general, once a pulse (e.g., a "transient pulse") of pressure is applied from the proximal end of the device using an over-pressurized pulse (e.g., greater than the target pressure) the pressure within the device may normalize to a final working (final) pressure that is approximately equal to the target pressure (e.g., within +/−1%, 2%, 3%, 4%, 5%, 6%, 7%, 8%, 9%, 10%, etc. of the target pressure).

The apparatuses and methods described herein may de-rigidizing by rapidly opening one or more venting valves to release the pressure rigidizing the device. Alternatively or additionally, any of the apparatuses described herein may also or alternatively use one or more de-pressurizing pulses, e.g., applying a pulse of negative evacuation pressure, to convert a rigidizing device from the rigid state to a flexible state. For example, a rapid pulse of negative pressure (suction) may be applied to de-rigidize any of these apparatuses. The pulse of negative pressure may have a rapid on time (e.g., 100 milliseconds or faster, 50 milliseconds or faster, 25 milliseconds or faster, 10 milliseconds or faster, 5 milliseconds or faster), and may be, e.g., −0.25 atm or higher vacuum (e.g., −0.5 atm, −0.75 atm, −1 atm, etc.). Thus, in any of these apparatuses and methods the apparatus (e.g., controller) may be configured to apply one or more pulses of negative pressure. The apparatus may be coupled to or may include a source of negative pressure (e.g., pump, tank, etc.).

Any of the apparatuses and methods described herein may be configured to prevent and/or limit leak of the rigidization medium from the rigidizing device or devices. Any of these apparatuses and methods may include one or more (and preferably redundant) sensors that may be used to detect leak(s). These one or more sensors may be configured to sense pressure within the rigidizing device (e.g., in communication with a compression layer or region (e.g., bladder layer or region), within one or more escape or leak pathways (e.g., in communication with a pressure escape pathway), in communication with one or more region outside of the rigidizing device(s) (e.g., to measure intracolonic pressure in variations configured as an endoscope, etc.), and/or in communication with the handle region and/or in communication with the pressure controller (e.g., rigidizing pressure control system/sub-system). The sensors may include pressure sensors and/or flow sensors and may signals from these sensors may be received, processed, stored and/or transmitted by the apparatus, including by the rigidizing pressure control system/sub-system. The apparatus may adjust the application of pressure using this feedback, and/or it may emit one or more alerts to a user to indicate leak (or non-leak).

For example, the apparatus may be configured to detect leak within the rigidizing apparatus when the apparatus is configured to be rigidized by detecting a change in pressure within the compression layer/region over time. One or more (e.g., redundant) pressure sensors may sense pressure in a continuous, and/or periodic manner. Depending on the rate of the change in pressure detected over time, the apparatus may trigger an alert and/or action; for example if the rate of change of the pressure (when not applying a pulse of pressure to the compression layer/region) is greater than a first threshold valve (e.g., the slow leak threshold value) but less than a second threshold value (e.g., a rapid leak threshold value), the system may optionally indicate a fault, and the controller may automatically provide one or more additional (refill) pulses to increase the pressure to the target rigidized pressure. If the detected rate of change in the pressure of the rigidized device is equal to or greater than the second threshold value, the system may include a leak fault and may vent (e.g., de-rigidize) the one or more rigidizing devices. These apparatuses and methods may also track the amount (volume) of fluid leaked over time, based on the rate of leakage (e.g., the rate of pressure change) over time, and the time (e.g., the duration of the leak).

The apparatuses and methods described herein may also determine the location of the leak, for example if the leak is occurring into a region of the body (e.g., colon, esophagus, etc.) around the rigidizing device(s), by including or using one or more sensors that sense pressure and/or flow outside of the rigidizing device(s). For example, any of these apparatuses may include one or more pressure sensors on or in communication with an external region at a distal end region of the rigidizing device(s), e.g., overtube, endoscope, etc., including at the distal tip region, at or in communication with an external region at a medial portion of the rigidizing device(s), and/or at or in communication with an external region at a proximal end of the rigidizing device(s). Measuring changes in the external pressure may allow the system, e.g., the controller, to determine if the leak is occurring into the external region. The sensed pressure may also be used to determine if there is a risk of damage to the surrounding environment. In some examples the external pressure may be monitoring and may provide an indication if the change in pressure is due to a leak in the apparatus (which may be configured by a corresponding pressure detection from within the apparatus). Alternatively, in some examples the apparatus or method may indicate that a change in external pressure is due to insufflation or other additional instrument.

Any of the methods and apparatuses described herein may include one or more pressure escape pathways to prevent a leak from within the device, e.g., a leak from out of the compression layer (also referred to herein as the bladder layer). The pressure escape pathway may generally be outside of the compression layer, and in some cases may pass though or between the rigidizing layer, or between the compression layer and the rigidizing layer. The pressure escape pathway may provide a continuous fluid pathway from the distal end region of the rigidizing device to the proximal end region and may fluidly connect to a pressure outlet or pressure escape port that may be open at or near the proximal end (e.g., in some examples a handle region. Thus, the pressure escape pathway or port may be open and may vent to the proximal region.

For example, described herein are rigidizing devices comprising: an elongate flexible tube; a rigidizing layer comprising an array of filament lengths crossing over and under each other and configured to move relative to each other; an inlet configured to attach to a source of positive pressure; a compression layer configured to be pushed against the rigidizing layer by a pressure differential from the inlet to rigidize the rigidizing layer, wherein the rigidizing device is configured to change between rigid and flexible states by the application of or release of pressure; a pressure escape port at a proximal end region of the elongate flexible tube; and a pressure escape pathway through the rigidizing layer, wherein the pressure escape layer permits a pressurized fluid leaking from the compression layer pass out of the pressure escape port without leaking through the elongate flexible tube. In some examples the pressure escape pathway is between the compression layer and an inner wall of the elongate flexible tube. In some examples the array of filament lengths comprises a plurality of discrete filaments. For example, at least some of the filament lengths of the array of filament lengths may be part of the same filament. The array of filament lengths may comprise a weave, a braid, a knit, chopped filaments, or randomly oriented filaments. The array of filament lengths may comprise one or more wires. Any of these devices may include a reinforced outer layer.

In general, the pressure escape pathway may be adjacent, or in fluid communication with the region immediately adjacent to, the compression layer (e.g., bladder layer). In any of these examples the pressure escape pathway may include a gap layer between the rigidizing layer and the outer or inner layers. The pressure escape pathway may be between the reinforced outer layer and the compression layer.

In any of these rigidizing devices the elongate flexible tube may include a coil-reinforced tube. The inlet may be coupled to a proximal end of the flexible elongate tube. In some examples the inlet is configured to attach to a source of positive pressure, further wherein the compression layer is configured to be pushed against the rigidizing layer when the positive pressure is applied through the inlet. Alternatively, in some examples the inlet may be configured to attach to a source of negative pressure, further wherein the compression layer is configured to be pushed against the rigidizing layer when the negative pressure is applied through the inlet. In this configuration, the escape pathway may prevent suction of fluid (e.g., gas, liquid, etc.) from within the body adjacent to the rigidizing device, and may instead draw air from the proximal end.

In any of these examples the compression layer may comprise a plastic, a plastomer, a composite, or an elastomeric layer. As mentioned, the compression layer may comprise a bladder. The rigidizing device may be configured to have a rigid configuration when positive pressure or negative pressure is applied through the inlet and a flexible configuration when the pressure is not applied through the inlet.

In general the apparatuses and method described herein may be configured to control the rigidity of the rigidizing device based on one or more sensed pressures, including pressure within the elongate rigidizing device (e.g., within the compression/bladder layer), and/or pressure within a region adjacent to the compression region/bladder layer) and/or pressure outside of the elongate rigidizing device (e.g., within a body region in which the elongate rigidizing device has been inserted, such as, but not limited to, the colon, e.g., intracolonic pressure).

For example, described herein are methods of controlling rigidization of an elongate rigidizing device. In some examples the apparatus (e.g., a controller including one or more processors) may be configured to perform any of these methods. For example, the method may include: sensing a decrease in pressure within a compression region of the elongate rigidizing device while the elongate rigidizing device is in a rigid configuration; sensing a pressure external to the elongate rigidizing device; applying one or more pulses of pressurized fluid through a pressure line to increase the pressure within the compression region of the elongate rigidizing device to maintain the rigidity of the elongate rigidizing device if the pressure external to the rigidizing device does not exceed a threshold; and de-rigidizing the compression region of the elongate rigidizing device and triggering an alert if the pressure external to the rigidizing device exceeds the threshold.

In any of these methods an apparatuses sensing the pressure external to the rigidizing device may comprise sensing the pressure through a lumen of the elongate rigidizing device.

In general these method may include clearing an obstruction from the external sensor, e.g., by applying fluid (e.g., air, nitrogen, water, saline, etc.) through the channel used to detect external pressure. In some examples the external pressure is sensed through a lumen within the elongate rigidizing device and any of these methods may include applying a fluid through the lumen to clear any obstruction immediately prior to (or while) sensing the pressure external to the elongate rigidizing device.

Sensing the pressure external to the elongate rigidizing device may include sensing pressure within a body cavity into which the elongate rigidizing device has been inserted. In any of these methods an apparatuses, sensing the pressure external to the elongate rigidizing device comprise sensing intracolonic pressure.

Also described herein are methods and apparatuses for sensing a rate of change of the pressure within the apparatus (e.g., within the compression region, within the fluid supply lines, within a leak path, including but not limited to an escape path, etc.) and controlling the rigidization state, either to add additional pressurized fluid or to de-rigidize the apparatus (e.g., and halt the procedure) and/or trigger an alert and/or alarm. For example, described herein are methods of controlling rigidization of an elongate rigidizing device, the method comprising: identifying a decrease in pressure within a compression region of the elongate rigidizing device while the elongate rigidizing device is in a rigid configuration; applying one or more pulses of pressurized fluid through a pressure line to increase the pressure within the compression region of the elongate rigidizing device to maintain the rigidity of the elongate rigidizing device if the decrease in pressure does not exceed a first threshold; and de-rigidizing the compression region of the elongate rigidizing device and triggering an alert if the decrease in pressure exceeds a second threshold that is greater than the first threshold.

For example, any of these methods may include de-rigidizing the compression region of the elongate rigidizing device and triggering the alert further comprises sensing a pressure external to the elongate rigidizing device and de-rigidizing the compression region when the decrease in pressure exceeds a second threshold that is greater than the first threshold and when the pressure external to the elongate trivial exceeds a leak threshold.

All of the methods and apparatuses described herein, in any combination, are herein contemplated and can be used to achieve the benefits as described herein.

BRIEF DESCRIPTION OF THE DRAWINGS

A better understanding of the features and advantages of the methods and apparatuses described herein will be obtained by reference to the following detailed description that sets forth illustrative embodiments, and the accompanying drawings of which.

DETAILED DESCRIPTION

The methods and apparatuses (e.g., systems, sub-systems, device, etc.) described herein may improve the operation and safety of dynamically rigidizing devices. For example, described herein are rigidizing pressure control systems or sub-systems. These rigidizing pressure control systems or sub-systems may control the application of pressure to rigidize/de-rigidize a pressure-rigidized device. Also described herein are apparatuses and methods for reducing or eliminating risks of cross-contamination between a rigidizing pressure control systems or sub-systems and a rigidizing device. Also described herein are apparatuses and methods for releasing pressure (e.g., pressure relief) from a region of the body surrounding a rigidizing device when inserted into a body lumen. In addition, described herein are apparatuses and methods for controlling the routing tubing that may be particularly useful with rigidizing devices that roll relative to the source of fluid (including pressurized fluid). Each of these apparatuses and methods are described in greater detail below; these apparatuses and methods may be combined and may be used with one or more rigidizing devices, and in particular pressure-rigidizing devices. In particular, these methods and apparatuses may be used in combination with, and/or may modify and improve the rigidizable devices and methods of using them described in U.S. Pat. No. 11,135,398 (titled "DYNAMICALLY RIGIDIZING COMPOSITE MEDICAL STRUCTURES"), U.S. patent application Ser. No. 17/604,203 (also titled "DYNAMICALLY RIGIDIZING COMPOSITE MEDICAL STRUCTURES"), PCT/US2021/024582 (titled "LAYERED WALLS FOR RIGIDIZING DEVICES"), PCT/US2021/034292 (titled "RIGIDIZING DEVICES"), PCT/US2022/014497, (titled "DEVICES AND METHODS TO PREVENT INADVERTENT MOTION OF DYNAMICALLY RIGIDIZING DEVICES") PCT/US2022/019711, (titled "CONTROL OF ROBOTIC DYNAMICALLY RIGIDIZING COMPOSITE MEDICAL STRUCTURES"), U.S. provisional patent application 63/265,934, (titled "METHODS AND APPARATUSES FOR REDUCING CURVATURE OF A COLON"), U.S. provisional patent application 63/296,478, (titled "RECONFIGURABLE STRUCTURES"), U.S. provisional patent application 63/308,044, (titled "DYNAMICALLY RIGIDIZING COMPOSITE MEDICAL STRUCTURES"), U.S. provisional patent application 63/324,011, ("METHODS AND APPARATUSES FOR NAVIGATING USING A PAIR OF RIGIDIZING DEVICES"), U.S. provisional patent application 63/342,618, (titled "EXTERNAL WORKING CHANNELS FOR ENDOSCOPIC DEVICES"), U.S. provisional patent application 63/335,720, (titled "HYGIENIC DRAPING FOR ROBOTIC ENDOSCOPY") and U.S. provisional patent application 63/332,686, (titled "MANAGING AND MANIPULATING A LONG LENGTH ROBOTIC ENDOSCOPE"), each of which is herein incorporated by reference in its entirety.

Figure 1A:
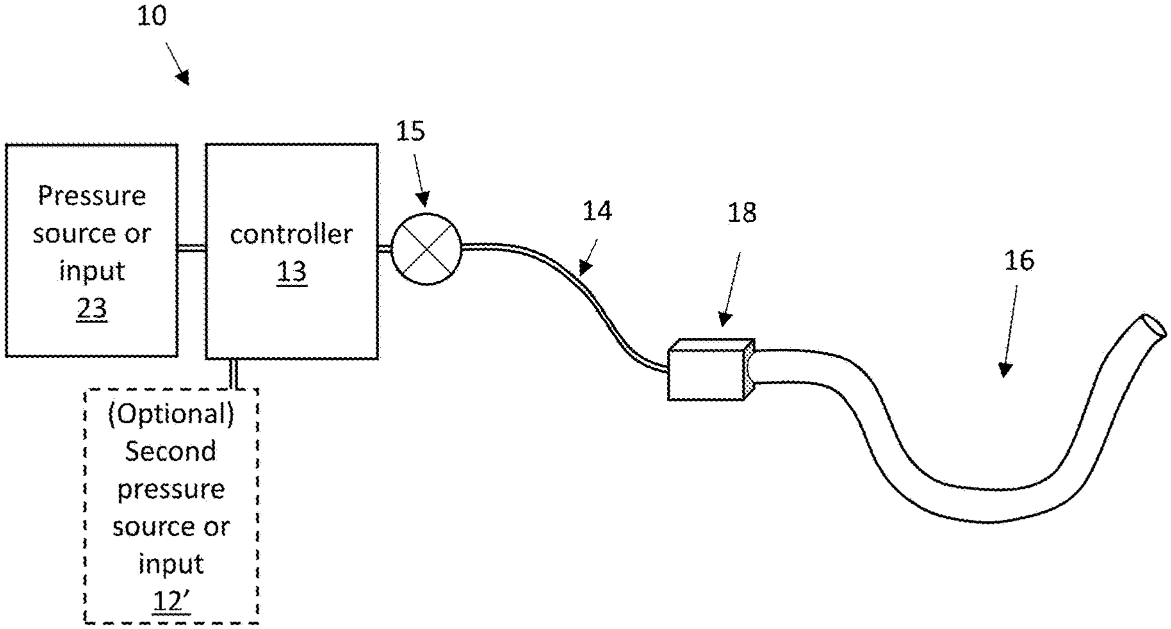
FIG. 1A schematically illustrates one example of an apparatus including a rigidizing device and a rigidizing pressure control system or sub-system.

For example, described herein are apparatuses, including sub-systems, for regulating and/or controlling the application of fluid pressure, and in particular air pressure, to rigidize or de-rigidize a device. FIG. 1A shows a first example of a rigidizing pressure control system (or sub-system) connected to a rigidizing device. In this example the rigidizing pressure control system/sub-system 10 is integrated with the rigidizing device 16. The rigidizing pressure control systems/sub-systems described herein may include a pressure source 23 or may be configured to be coupled to a pressure source. The pressure source may include a pump (pressure pump), and/or a local or remote tank/cannister/accumulator of pressurized fluid (e.g., pressurized air or other gas), etc. The pressure source may be a source of positive pressure or of negative pressure. There can be dual pressure sources or multiple pressure sources, some of them positive and some of them negative. Although the majority of the examples described herein refer to positive pressure, it should be understood that many of the apparatuses and methods described herein may be used with, or may be readily adapted for use with negative pressure (suction).

In FIG. 1A, the rigidizing device 16, which may be, e.g., an overtube or an endoscope or the like, includes a handle region 18 at the proximal end. The proximal end region (such as the handle in some examples) may include one or more pressure inlet ports that can be coupled to the rigidizing pressure control system/sub-system 10 to apply pressure to one or more bladders/compression layer(s) within the rigidizing device 16. Controlling the application of pressure to the bladder/compression layer(s) may control the transition between non-rigid (e.g., flexible, floppy) and rigid states. One or more valves 15 may be connected between one or more sources of pressurized fluid 23, 12' of the rigidizing pressure control system/sub-system 10 and the pressure inlet port of the rigidizing device. The rigidizing pressure control system/sub-system 10 may include a controller 13 (e.g., control circuitry). The control circuitry may include one or more processors, one or more memories, one or more clocks, and may include control logic. The control circuitry may receive input from one or more pressure and/or flow sensors (not shown) which may receive date from within the pressure pathway and/or the rigidizing device. The control circuitry may receive input from one or more inputs, including user control inputs that may turn operation on/off, trigger immediate de-rigidization, set the level of pressure applied, etc. The control circuitry may be configured to control the operation of the one or more valves (e.g., open one or more valves to apply pressurized fluid to rigidize, open one or more valves to vent pressurized fluid and de-rigidize the elongate rigidizing device). As shown in FIG. 1A, the rigidizing pressure control system/sub-system 10 may include a pressure source input 23 (such as a source of positive pressure, e.g., a pump, tank, etc.); in some examples the apparatus may include a second pressure source or input 12'. The second pressure source or input 12' may be configured to provide negative pressure if the first pressure source or input provides positive pressure. For example, the second source of pressure may provide a suction source that may be controlled (e.g., via the controller) to apply a negative, evacuation, pressure that may assist in actively and controllably de-rigidizing the device.

Figure 1B:
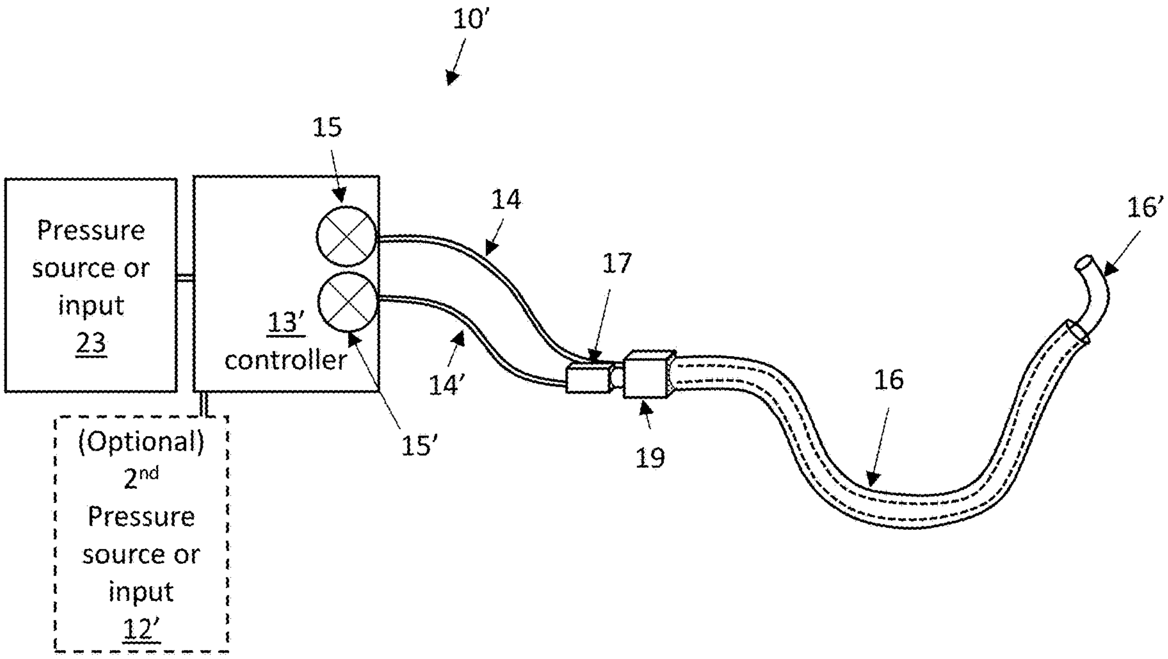
FIG. 1B schematically illustrates an example of an apparatus having one rigidizing pressure control system or sub-system configured to control pressure to separately rigidize a pair of nested rigidizing devices.

FIG. 1B schematically illustrates one example of a rigidizing pressure control system (or sub-system) connected to a pair of nested rigidizing devices 16, 16'. The outer rigidizing device may be configured as an overtube 16 and the inner rigidizing device may be configured as an endoscope 16'. Both the inner and outer rigidizing devices may include handles. For example, the inner rigidizing device may include an inner rigidizing device (endoscope) handle 17 and the outer rigidizing device may include an outer rigidizing device (overtube) handle 19. The inner and outer rigidizing devices may be moved (e.g., axially) and/or steered (distally) independently of each other, and may be separately rigidized. As shown in FIG. 1B, the rigidizing pressure control system/sub-system 10' in this example may be configured to control the application of pressurized fluid (from a single or multiple pressure sources/inputs 23, 12') to each of the rigidizing devices 16, 16'. A single controller 13' may control operation of multiple valves 15, 15' and control the application of pressure to each pressure line 14, 14' connecting to the inner 16' and outer 16 rigidizing devices.

In general, the apparatuses and methods described herein may be used with a rigidizing device that is controlled by the application of pressurized fluid. The pressurized fluid may cause one or more bladder layers (also referred to herein a compression layers in some examples) against one or more rigidizing layer or layers. This may compress the rigidizing layer, causing it to stiffen. For example, FIG. 2A illustrates an example of a transverse section through an elongate rigidizing device, showing the arrangements of the many layers that may be included. Note that some of these layers are optional. In this example the rigidizable device 100 is configured to be actuated by the application of a negative pressure (e.g., vacuum); in some examples a positive pressure (e.g., pressurized fluid) may be used. The device 100 shown includes an inner layer 115 that may be reinforced (e.g., by including one or more reinforming members, such as a helically arranged strip, ribbon or wire), an optional slip layer 113, a gap 111, a rigidizing layer 109, configured in this example as a braid layer, a second gap 107 and an outer layer 101, all around a central lumen 120. In some examples a vacuum may be applied between the outer layer and the inner layer to rigidize. For example, a port (pressure inlet port, not shown) configured to couple to the source of negative pressure may be located at the proximal end of the device and may be in fluid communication with the gap region 107 between the flexible outer layer 101 and the rigidizing layer 109, e.g., braided layer. Thus, in this example the outer layer may act as a compression layer. Alternatively, in some examples (as shown in FIGS. 3A-3B) the apparatus may be configured so that a layer radially outward from the rigidizing layer is also reinforced so that positive pressure may drive a layer (e.g., compression layer 101) against the rigidizing layer and the inner layer to rigidize.

Figure 2B:
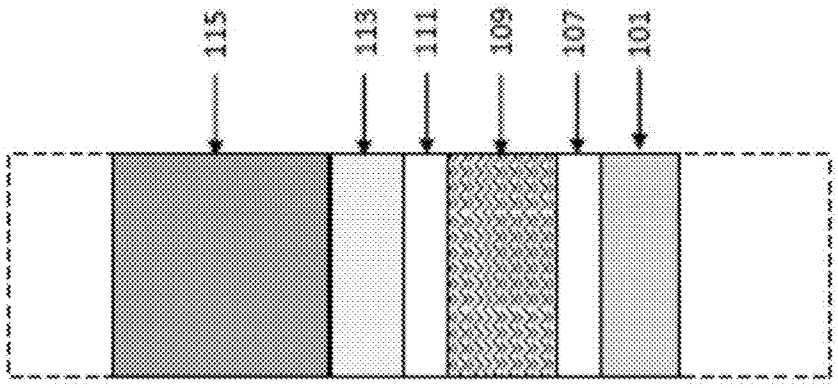
FIG. 2B is an enlarged view showing one example of the arrangement of layers within the elongate rigidizable device of FIG. 2A.
Figure 2A:
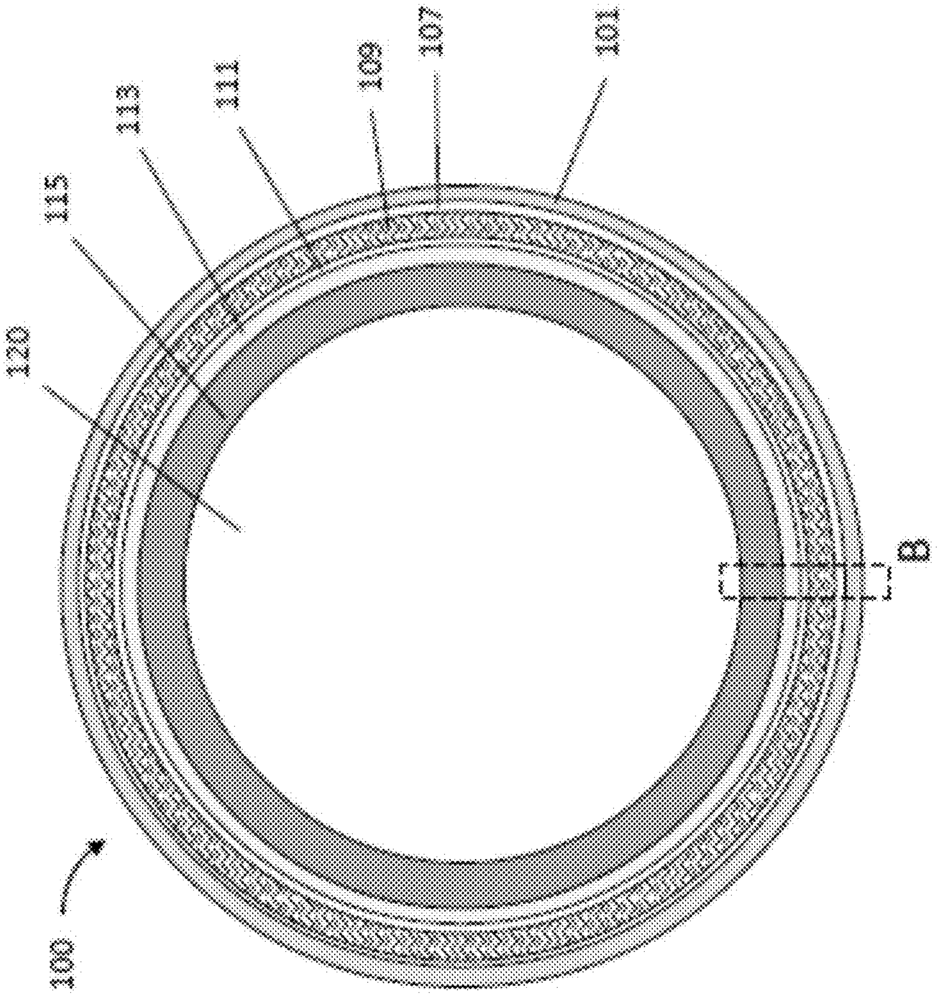
FIG. 2A is a section through an elongate rigidizable device that may be rigidized by the application of negative pressure.

FIG. 2B shows a section through one wall region B of the cylindrical-shaped body of the device. Applying suction may allow the outer layer 101 to be drawn onto the rigidizing layer, causing it to rigidize, limiting or preventing bending of the device. In the example rigidizing device illustrated in FIGS. 2A-2B the apparatus may be configured to include a pressure escape pathway in the regions (e.g., gap region 107, 111) around and/or adjacent to a compression layer and/or through the rigidizing layer 109. In general this pressure escape pathway may be fluidly continuous with an escape port at a proximal end region of the device (in some examples in a handle), e.g., a region configured to be outside of the body.

Figure 3B:
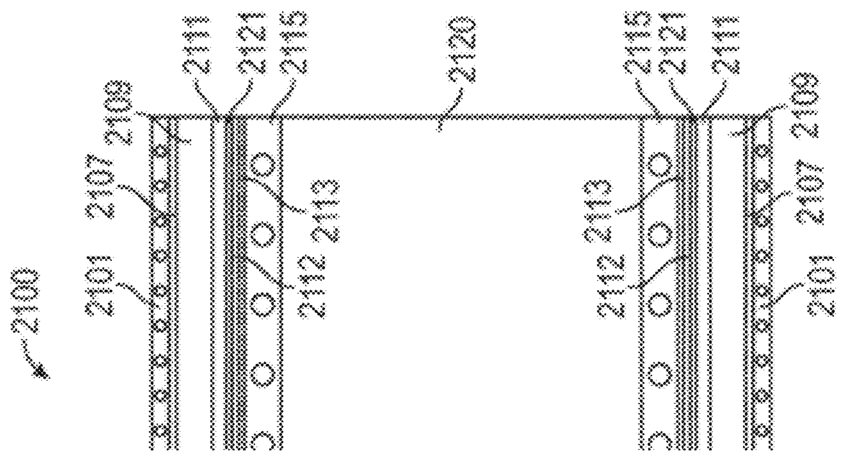
FIG. 3B is an alternative sectional view showing one example of the arrangement of layers within the elongate rigidizing device of FIG. 3A.
Figure 3A:
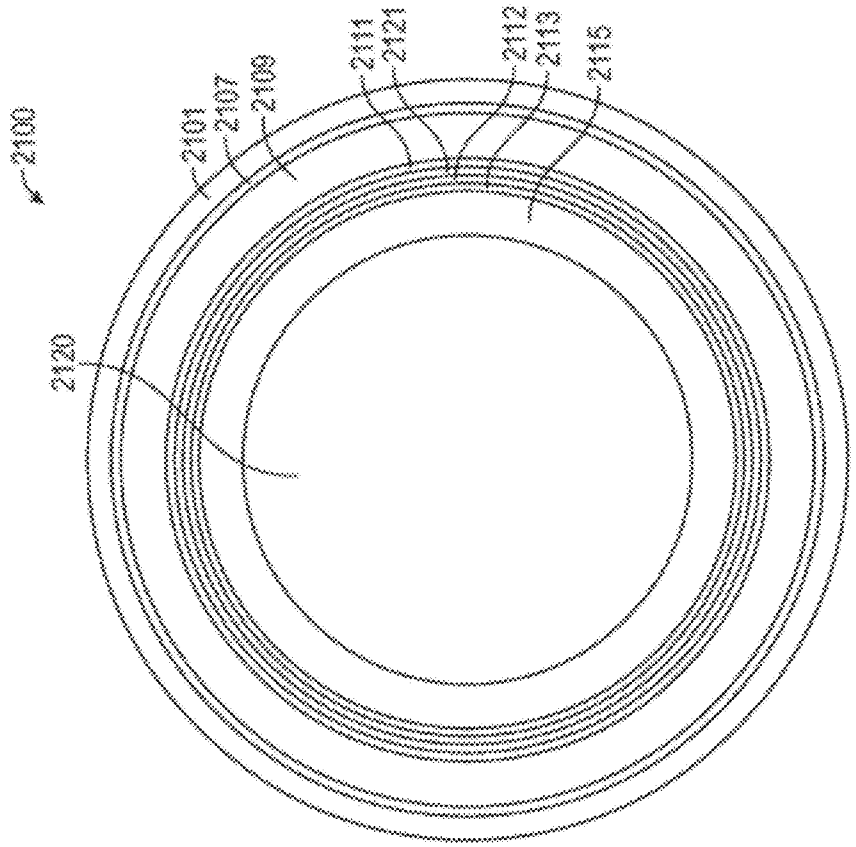
FIG. 3A is a section through an elongate rigidizable device that may be rigidized by the application of positive pressure.

Another example of a rigidizable device 2100 is shown in FIGS. 3A-3B. In this example the device may also be an elongate, e.g., catheter or tubular-shaped device similar to that in FIGS. 2A-2B but may be rigidized by the application of positive pressure. For example, FIG. 3A shows a section transverse to the long axis of an elongate rigidizable device. In this example, the layers forming the device are arranged so that an inner reinforced layer 2115 is the most radially-inward layer and may be reinforced, e.g., by a helically wound ribbon, strip, cable, etc. The device may also include an optional slip layer 2113 which may reduce the friction between the inner layer and the more radially-outward layers. The slip layer may be a powder, or it may be a lubricious layer or a layer of lubricious material. A first gap 2112 layer is shown separating the inner layer 2115 and/or the slip layer 2113 from a compression layer, configured in this example as a bladder layer 2121. A second (or intermediate) gap layer 2111 spaces the bladder layer from the rigidizing layer 2109, shown in this example as a braid layer. A third gap layer 2107 is positioned between the rigidizing layer and an outer layer 2101. The outer layer in this example (similar to the inner layer 2115) is reinforced, for example, by a helically wound filament, wire, fiber, band, etc. Although not shown, when actuated by the application of positive pressure between the compression (e.g., bladder) layer and the inner layer, the bladder layer may push the braid layer into the outer layer to rigidize the rigidizing layer. The layers surround a central lumen 2120.

Both examples of a devices shown in FIGS. 2A-2B and 3A-3B may include additional optional layers or components. Further, the compositions of the rigidizing layers may be modified in order to improve performance. In particular the rigidizing layer may be modified to include structures (e.g., knits, woven, braids, scales, plates, arrays of filaments, granules, etc.) that may enhance or improve performance. Rigidizing elements may be used as one type alone, or in conjunction with other rigidizing elements. In some examples the inner and/or outer layers may be modified to enhance or improve performance, including the addition of torsional control components, and/or modulating the durometer of the inner and outer regions of these layers. In the example rigidizing device illustrated in FIGS. 3A-3B the apparatus may be configured to include a pressure escape pathway in the regions (e.g., gap region 2107, 2111) around and/or adjacent to a compression layer 2121 and/or through the rigidizing layer 2109. In general this pressure escape pathway may be fluidly continuous with an escape port at a proximal end region of the device (in some examples in a handle), e.g., a region configured to be outside of the body.

Figure 4:
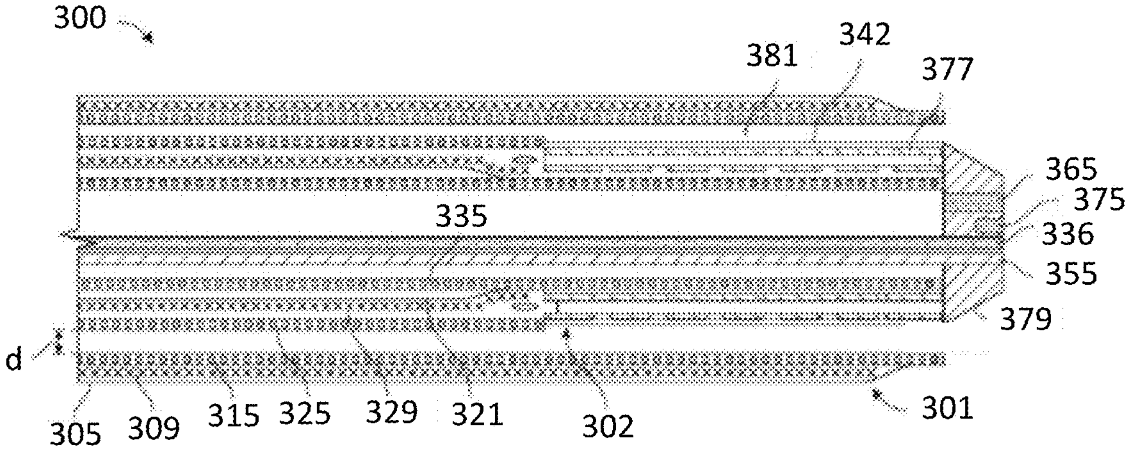
FIG. 4 illustrates an example of a section through one example of a nested pair of rigidizable elongate devices, arranged as a mother (outer) and child (inner) pair.

Further, any of the rigidizable devices described herein may be configured as nested apparatuses that may be nested to provide enhanced performance. For example, a nested apparatus (system) is shown in FIG. 4 and illustrated in operation in FIGS. 5A-5B. In FIG. 4, the nested system 300 includes an outer rigidizing device 301 and an inner rigidizing device 302, configured as a rigidizing scope) that are axially and rotationally movable with respect to one another. In this example they move concentrically, but in some configurations they may be arranged non-concentrically. The outer rigidizing device 301 and the inner rigidizing device 302 can include any of the rigidizing features as described herein. For example, the outer rigidizing device 301 can include an outermost layer (e.g., tube) 305, a rigidizing (e.g., braided) layer 309, and an inner layer (e.g., tube) 315. Either or both the inner and outer tubes (layers) 305, 315 may be reinforced, e.g., including a coil wound therethrough. The outer rigidizing device 301 can be, for example, configured to receive vacuum between the outermost layer 305 and the inner layer 315 to provide rigidization. Similarly, the inner rigidizable device (scope 302) can include an outer layer 325 (e.g., with a coil wound therethrough in this example), a rigidizing (e.g., braid) layer 329, a compression layer 321 (e.g., configured as a bladder layer in this example), and an inner layer 335 (e.g., with a coil wound therethrough).

The inner rigidizing device (e.g., scope 302) can be, for example, configured to receive pressure between the compression layer 321 and the inner layer 335 to provide rigidization. Any of these rigidizing devices, including the inner rigidizing device shown in FIG. 4, may include an air/water channel 336 and a working channel 355 can extend through the inner rigidizing device 302. Additionally, any of these rigidizing devices (including the inner rigidizing device 302 shown in FIG. 4) can include a distal section 342 with a camera 365, lights 375, and steerable linkages 377. A cover 379 can extend over the end of the distal section 342. In another example, the camera and/or lighting can be delivered in a separate assembly (e.g., the camera and lighting can be bundled together in a catheter and delivered down the working channel and/or an additional working channel to the distal-most end). The feature of any of these apparatuses may include or be incorporated into apparatuses including flexible external working channels can be incorporated (as described in U.S. provisional patent application No. 63/342,618, (titled "EXTERNAL WORKING CHANNELS FOR ENDOSCOPIC DEVICES"), herein incorporated by reference in its entirety.

The inner lumen 381 of the first, outer rigidizable device 301 can form a gap or interface 381 into which the second, inner, rigidizable device may be positioned. This gap or interface region 381 can have any appropriate dimensions, so that an annular space (d) remains around the second, inner, rigidizable device when inserted into the first, outer, rigidizable device. In some examples, when the inner rigidizable device is centered in the lumen of the outer rigidizable device, space on either side of the inner rigidizable device, d, may be between about 0.001"-0.050", such as 0.0020", 0.005", or 0.020" wide. The inner surface of the outer rigidizing device and/or the outer surface of the inner rigidizable device may be a low friction surface and may include, for example, powder, coatings (for example, hydrophilic or hydrophobic), or laminations to reduce the friction. In some examples, a seal may be present between the inner device 302 and the outer rigidizable device 301, and the intervening space can be pressurized, for example, with fluid or water, to create a hydrostatic bearing. In other examples, there can be seals between the inner rigidizable device 302 and outer rigidizable device 301, and the intervening space can be filled with small spheres to reduce friction.

The inner rigidizable device 302 and outer rigidizable device 301 can move relative to one another and alternately rigidize so as to transfer a bend or shape down the length of the nested system 300. For example, the inner device 302 can be inserted into a lumen and bent or steered into the desired shape. Pressure can be applied to the inner rigidizing device 302 to cause the rigidizing layer to rigidize the inner rigidizable device 302 in whatever configuration/curve/bend it had when the pressure was applied. The rigidizable device (for instance, in a flexible state) 301 can then be advanced over the rigid inner rigidizable device 302. When the outer rigidizable device 301 is sufficiently advanced relative to the inner rigidizable device 302, pressure (e.g., negative pressure in this example) can be applied to the outer rigidizable device 301 to cause the rigidizing layers to rigidize to fix the shape of the outer rigidizable device. The inner rigidizable device 302 can be transitioned to a flexible state, advanced, and the process repeated. Although the system 300 is described as including an inner rigidizable device configured as a scope, it should be understood that other configurations are possible. For example, the system might include two overtubes, two catheters, or a combination of overtube, catheter, and scope.

Figure 5A:
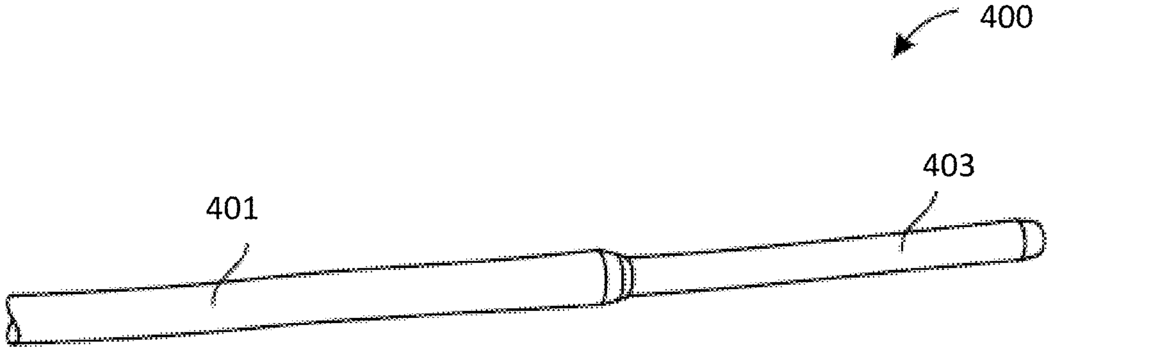
FIGS. 5A-5B illustrate an example of a method of operating a nested pair of rigidizing elongate devices that may selectively rigidize and un-rigidize to propagate a shape through a tortious pathway.
Figure 5B:
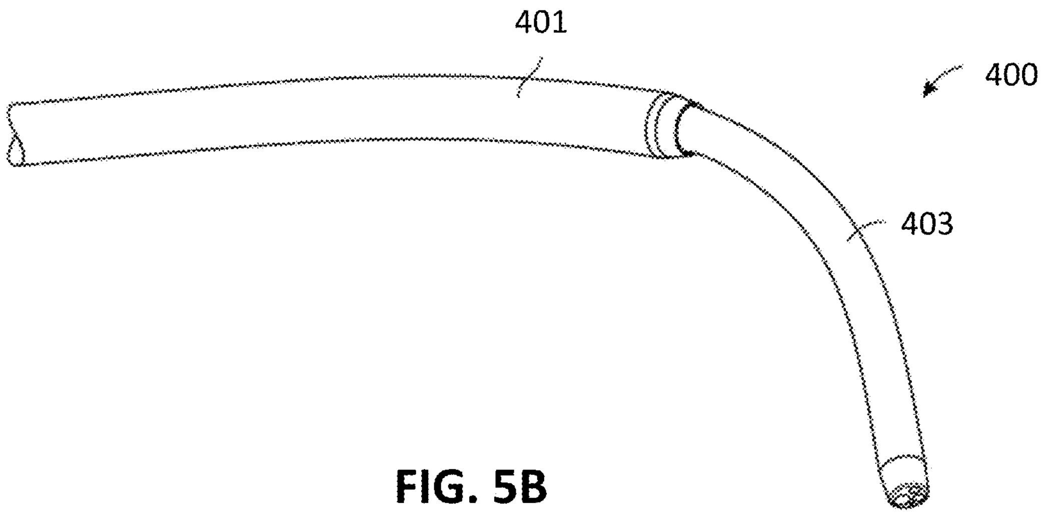

FIGS. 5A-5B illustrate the ability of these nested systems 400 to advance though very tortious anatomy by control from the proximal end of the device while controlling the pressure (and therefore the rigidity/flexibility) in both the inner rigidizable device 403 and the outer rigidizable device 401. For example, FIG. 5A shows the nested system 400 inserted initially in a linear (straight) configuration. The distal end of the inner rigidizable device 403 may be steerable and may be extended from the outer rigidizable device 401 while being steered into a bend, as shown in FIG. 5B. The inner rigidizable device 403 may then be rigidized by the application of a pressure differential, and the outer rigidizable device 401 advanced distally over the locked curved shape of the rigid inner rigidizable device 403.

FIGS. 3 and 5A-5B are shown and described to illustrate generally the nested systems and methods of operating them that may be performed with any of the rigidizable devices described herein. With respect to FIGS. 5A-5B, the example nested apparatus shown may be rigidized by any appropriate method, including, but not limited to, the application of positive and/or negative pressure to one or both rigidizing members. The modifications to the rigidizing member, torsional stiffness, and/or durometer of the inner and/or outer layers (tubes) of these rigidizable devices may provide enhanced movement and functionality of the nested devices described herein when performing a method similar to that shown in FIGS. 5A-5B.

Any of the rigidizing devices described herein may therefor include a rigidizing pressure control system or subsystem. In some cases the pressure control system (or sub-system) is configured as a normally closed architecture in order to rigidize the rigidizing device safely and quickly using pressurized fluid. A normally closed configuration may use a discrete amount of pressurized fluid that is held within the rigidizing device in the rigid configuration. Although some leakage may occur, the apparatus is closed, so that leakage may be minimized. This may minimize the inadvertent release of pressurized fluid (e.g., air) into the patient, should a rupture or break occur. This may minimize the amount and the pressure of the fluid released into the patient's body (e.g., into the colon when used for colonoscopy), which may prevent the build-up of pressure within the body that may otherwise harm a patient. Surprisingly, the use of a normally closed system may also enhance the rigidization speed and stiffness.

Figure 6:
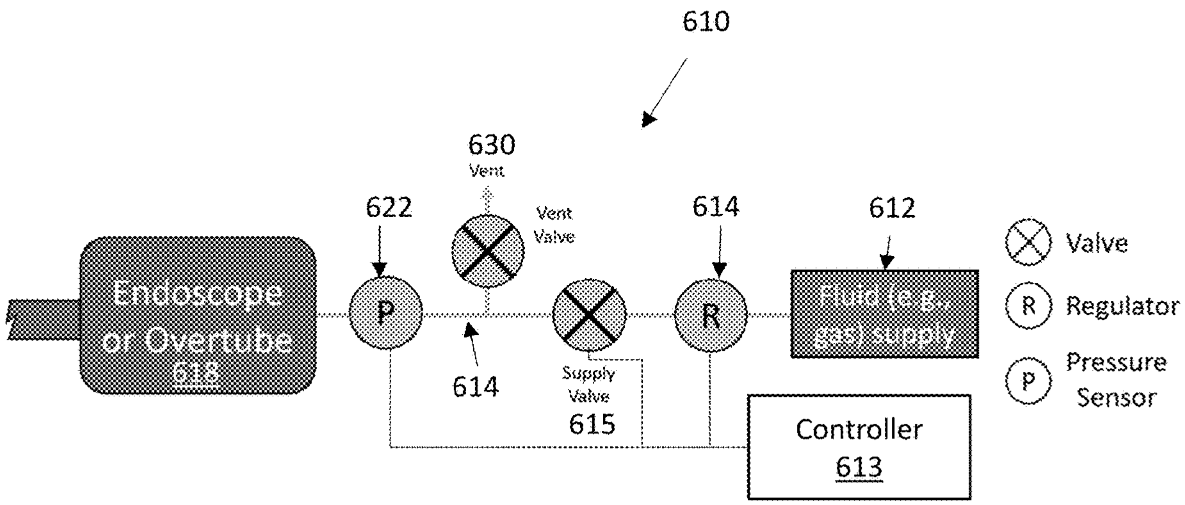
FIG. 6 schematically illustrates one example of a normally closed rigidizing pressure control system/sub-system that may be used to control rigidization of a rigidizing device.

For example, FIG. 6 schematically illustrates one example of a normally closed rigidizing pressure control system or sub-system 610. In this example, the system/sub-system includes a source of pressurized fluid 612 (e.g., a gas supply, such as a tank, cartridge, reservoir, etc. or other fluid, including liquids or gasses) that is connected to a regulator 614 (R) that may regulate the pressure of fluid leaving the source of pressurized fluid. A supply valve 615 is connected in-line with the regulator and source of pressurized fluid. Downstream (e.g. distal) to the supply valve, a vent valve 630 may be fluidly connected to the pressure line 614 and proximal to a pressure sensor 622 that may read a fluid pressure within the pressure line. A controller 613 may control operation of the pressure regulator 614 and valves 615, 630 and may receive input from the one or more sensors 622. The rigidizing pressure control system/sub-system 610 is shown coupled to a rigidizing device 618 (e.g., an endoscope or overtube in some examples).

In this example, the controller 613 may be configured to (when receiving an automatically or manually determined command to rigidize the rigidizing device 618), may cause a pulse of pressurized fluid to be delivered through the pressure line 614 to the rigidizing device 618. For example, the controller may open the supply valve 615, and then closed it after a short period of time (e.g., approximately 500 ms). For example, in some cases the controller may apply a pulse of pressurized fluid at approximately 4 atmospheres for 500 ms or less (e.g., approximately 300 ms, between 100 ms and 500 ms) to rigidize, and may de-rigidize over between about 800-500 ms. After the pressure has been delivered, the pressure in the rigidizing device may be maintained (typically at a lower pressure than the applied pressure, as the pressurized fluid pulse duration may be faster than the time to equilibrate the pressure within the rigidizing device, and the pressurized fluid is distributed along the length of the device. If the controller, upon receipt of data from the pressure sensor 622, detects a pressure drop in the device below a threshold, the controller may apply another (supplemental) pulse of pressure by opening the supply valve 615 for a short time (e.g., approximately 10 ms) to "top off" the device pressure. To de-rigidize, the controller may cause the vent valve 630 to open in order to vent the pressure in the rigidizing device.

As mentioned above, the normally closed configuration described herein may advantageous because even if a rupture or bursting of the device occurs, there is a limited volume of fluid (e.g., gas) that may enter the patient. In addition, the pressure sensor(s) may monitor the operation of the device and may prevent excessive pressurization and in some cases may detect premature depressurization (e.g., rupture). For example, if the device is losing pressure (e.g., leaking) too quickly, or the device ruptures, the system may indicate that a fault has occurred and may emit an alert. This configuration may also track the volume of gas that is leaked over time, particularly where the volume of the rigidizing device (e.g., the volume within the bladder/compression layer(s)).

Figure 7:
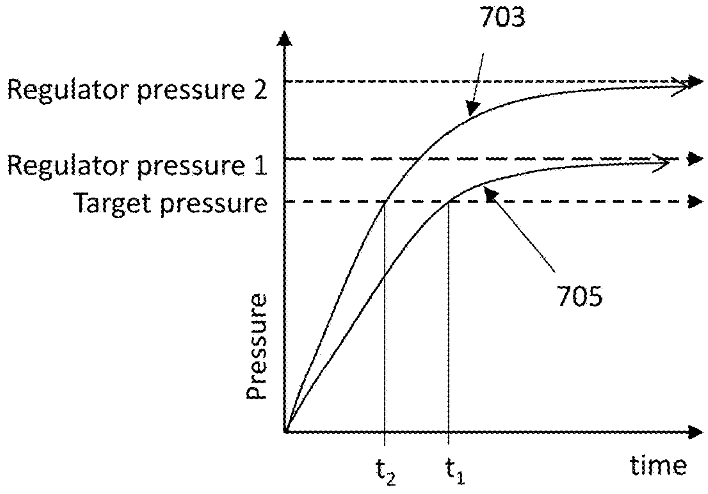
FIG. 7 is a graph showing the relationship between rigidization pressure and time in a rigidizing device.

In general, these methods may also adjust and/or increase the rate that the rigidizing device rigidizes. As shown in FIG. 7, the time required to rigidize the rigidizing device (shown as the time to reach the "target pressure") may decrease as the applied pressure increases. For example, for higher applied pressures 703 the time ($t_2$) to reach the target pressure, and therefore rigidization, is faster than the time ($t_1$) required for lower applied pressures 705. Thus, the pressure applied (which may be controlled by the pressure regulator 614) may be increased in order to reduce rigidization time. Even relatively small adjustments in the applied pressure (e.g., the regulator pressure) can greatly decrease the rigidization time due to the asymptotic nature of pressure increase. In general, an overpressure pulse may apply a pulse greater than the target pressure but the pressure within the rigidizing device (which typically includes an elongate volume) may stabilize at approximately the target pressure.

Figure 8A:
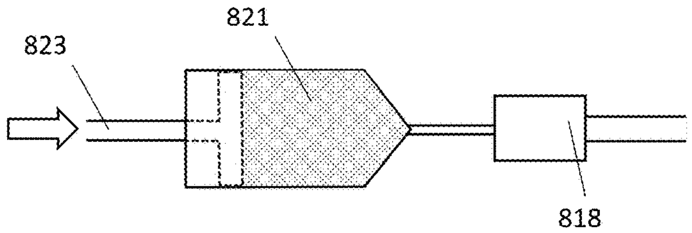
FIG. 8A schematically illustrates one example of a rigidizing pressure control system/sub-system having a fixed or set volume for rigidizing a rigidizing device.
Figure 8B:
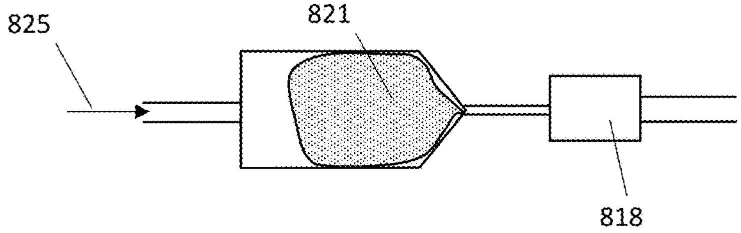
FIG. 8B schematically illustrates another example of a rigidizing pressure control system/sub-system having a fixed or set volume.

FIGS. 8A and 8B illustrate examples of apparatuses (e.g., rigidizing pressure control systems or sub-systems) having a fixed or set volume when rigidizing and maintaining rigidization. In FIG. 8A the fixed volume of rigidization medium 821 (e.g., pressurized fluid) may be delivered by depressing the plunger 823 to deliver the pressurized fluid into the rigidizing device 818. Similarly, in FIG. 8B, instead of a mechanical plunger, air pressure 825 may be used to drive the pressurized fluid 821 into the rigidizing device; the pressure may be maintained in the rigidizing device 818 by maintaining the air pressure. Thus in addition to the use of a source of pressurized fluid as described above, pressure may be applied by a mechanical displacement using a motor, etc. In FIGS. 8A and 8B the rigidization medium may be an incompressible fluid (e.g., water, saline, etc.) rather than a compressible fluid (e.g., air).

Figure 9:
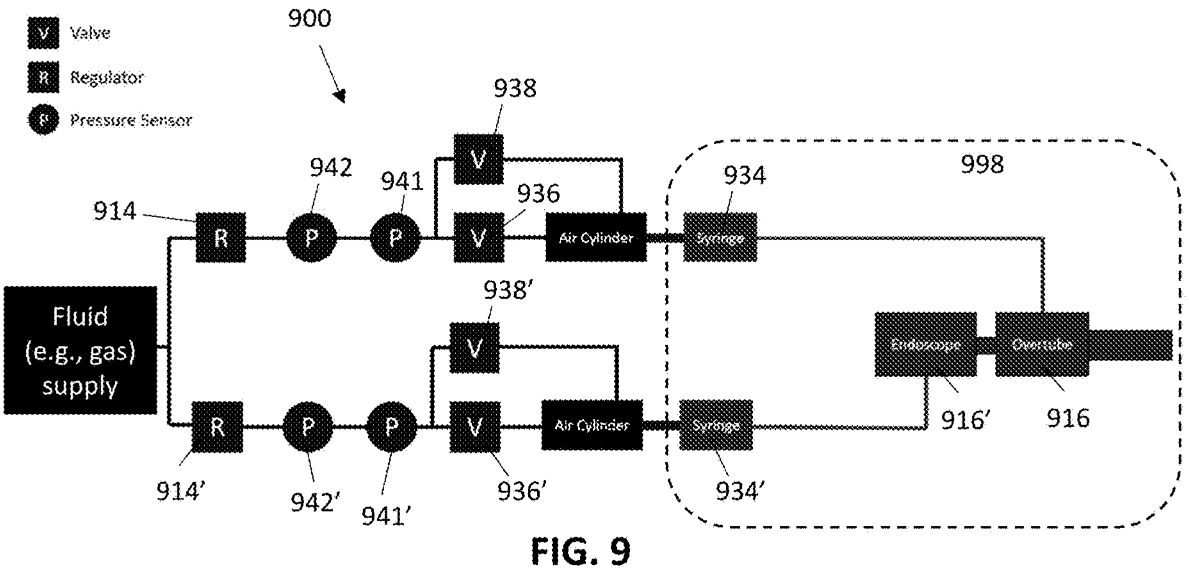
FIG. 9 schematically illustrates a normally closed rigidizing pressure control system/sub-system configured to control rigidization of a pair of rigidizing devices, one configured as an endoscope and one configured as an overtube.

FIG. 9 illustrates another example of a rigidizing pressure control system/sub-system 900 that is configured to have a normally closed architecture. In this example the apparatus is similar to that shown in FIG. 1B, and is configured to control the rigidization/de-rigidization of a pair of nested rigidizing devices, configured as an overtube 916 and an endoscope 916'. In this example, the rigidization medium is applied by a syringe 934, 934'. A controller (not shown) may control the pressure applied drive the syringe in each path separately either to open a first valve 936, 936' to advance the syringe plunger, or to open a second valve 938, 938' to withdraw the syringe plunger. The syringe(s) and rigidizing devices (e.g., overtube and endoscope) may be a single-use 998 component. The controller may also receive input from one or more of the pressure sensors (P) 942, 942', 941, 941' and may control each regulator 914, 914'. In this example, a non-compressible fluid (e.g., saline, water, etc.) may be used and a separate venting valve is not needed, as the fluid may be removed by withdrawing the syringe piston, applying negative pressure to remove the pressurizing fluid. Although the response time (de-rigidization/rigidization) times of apparatuses using an incompressible fluid may be generally somewhat slower than that for compressible fluids (e.g., air), the response time may be improved by reducing the size of the rigidization chambers (e.g., the fluid line, bladder, etc.) and in some cases adding ballast (e.g., filler material) in order to reduce the size of the bladder/compression layer(s). In any of the apparatuses described herein the regulator may be part of or controlled by the controller.

Figure 10:
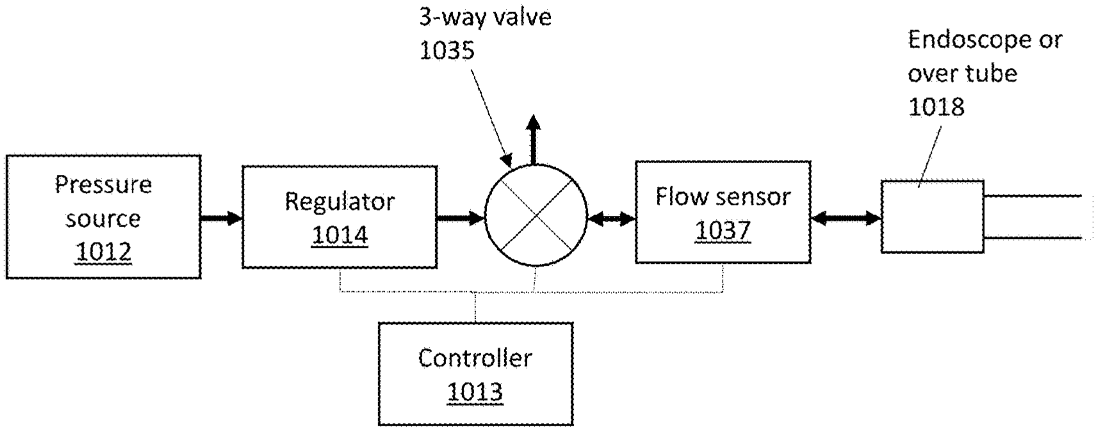
FIG. 10 schematically illustrates an example of a normally closed rigidizing pressure control system/sub-system.
Figure 11A:
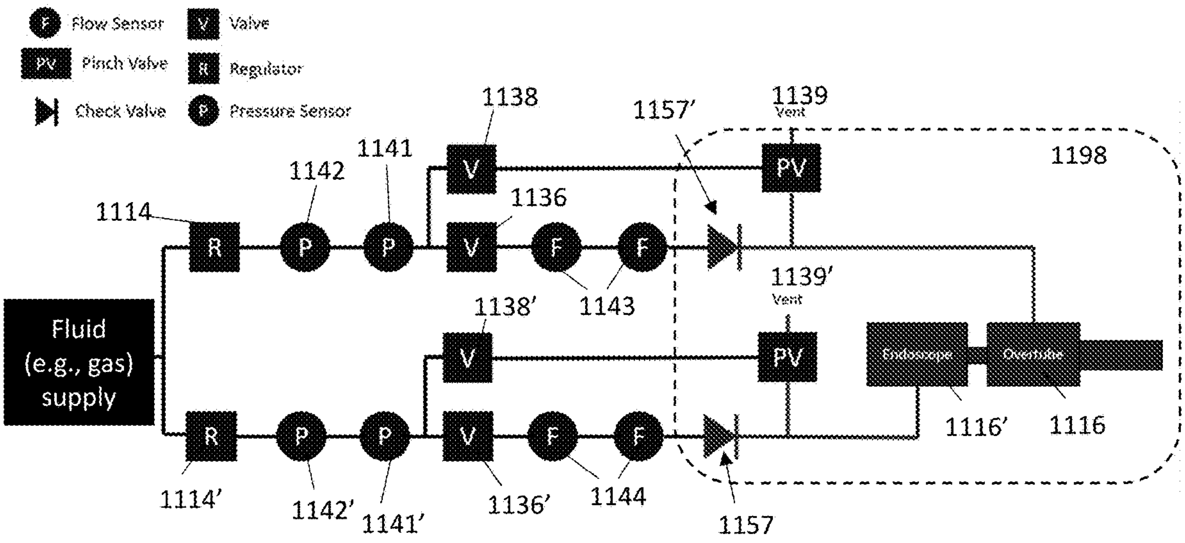
FIG. 11A schematically illustrates an example of a normally open rigidizing pressure control system/sub-system.
Figure 11B:
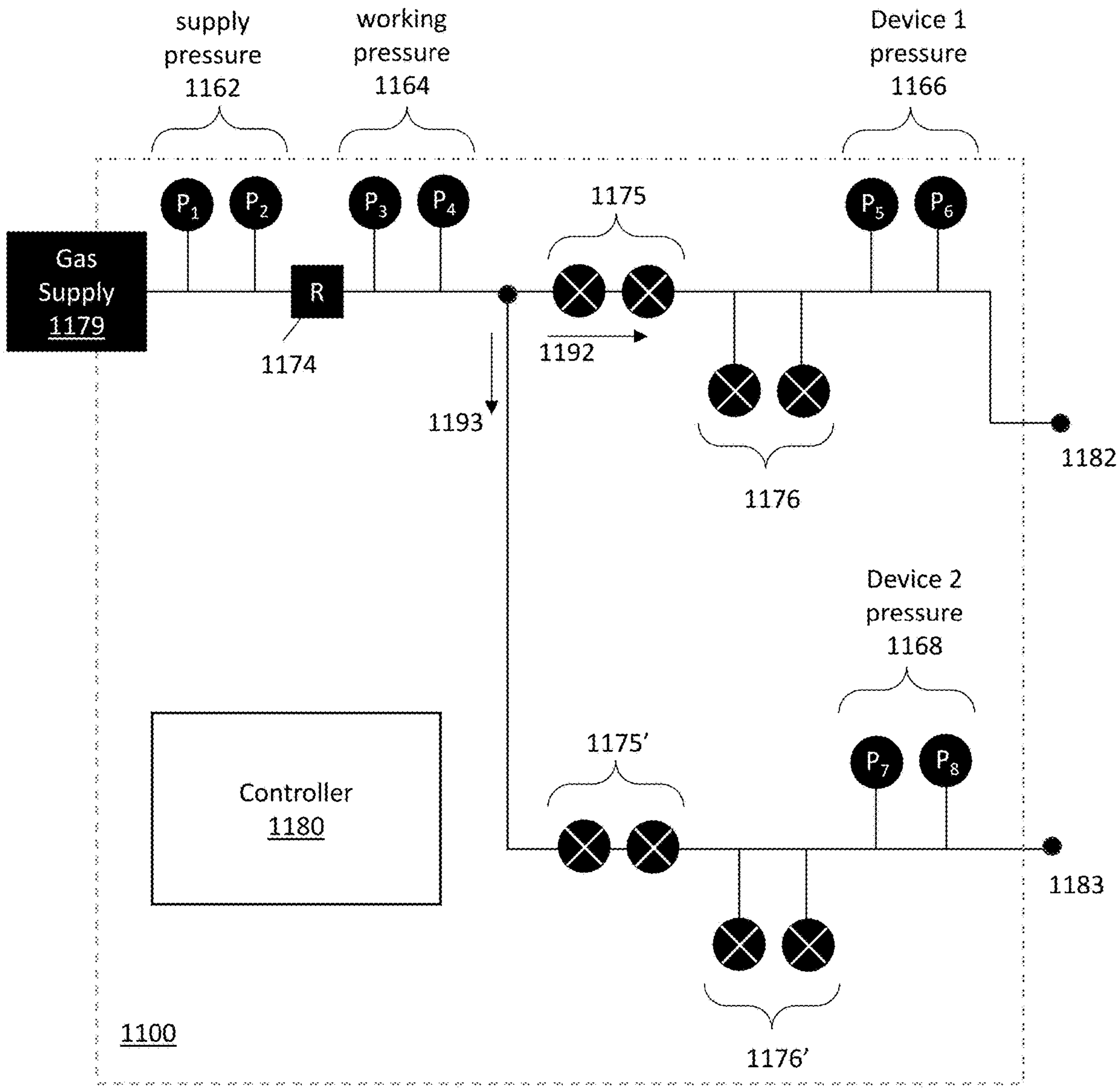
FIG. 11B schematically illustrates an example of rigidizing pressure control system/sub-system as described herein.

FIGS. 10 and 11A-11B schematically illustrate different examples of rigidizing pressure control systems/sub-systems configured as normally open configurations in which, to rigidize the device, the controller opens one or more valves to place the regulator-regulated pressures in fluid communication with the bladder/compression layer(s) endoscope. In practice, the same core elements may be used as described for the normally closed configuration, except that the in the normally open configuration the controller may keep the one or more valves open to allow pressure from the pressure source 1012 to remain in continuously fluid communication with the fluid line. If one or more flow sensors and/or pressure sensors in communication with the fluid line detects a burst, the controller may close off the applied regulator pressure and may open the endoscope pressure system to the vent. To de-rigidize the system, the bladder/compression layer(s) may be opened to a vent (or in some variations, to apply a negative pressure/suction to accelerate venting). In the context of FIG. 10, a controller 1013, which may include one or more processors (and other hardware, software and/or firmware) that may receive sensed input information from one or more sensors 1037 (e.g., a flow sensor is shown, but other sensors, including pressure sensors, may be used in addition or instead). The controller may also control the regulator 1014 and a valve, shown in this example as a multi-way (e.g., 3 way) valve 1035 to switch between applying the pressure to rigidize and opening the vent to the local environment. The example shown in FIG. 11A is similar to that shown and described above in FIG. 9, but in the context of a normally open configuration. In FIG. 11A the apparatus, or a line connecting the apparatus to the rigidizing pressure control system/sub-system, may include a venting line with a vent 1139, 1139', shown in this example as a valve (e.g., pinch valve, PV) in both the overtube and endoscope paths. The controller, not shown, may receive input on pressure with the pressure line from one or more pressure sensors 1142, 1142', 1141, 1141' and one or more flow sensors 1143, 1144 (which may instead be a pressure sensor), and may control one or more valves 1136, 1136', 1138, 1138'. The controller may control (and/or include) the regulator(s) 1114, 1114'. The fluid line may also include a one-way valve 1157, 1157' to prevent flow of material from the rigidizing device back into the rigidizing pressure control systems or sub-systems. In operation, the apparatus shown in FIG. 11A may provide a normally open architecture that allows for the independent (or separate) operation and rigidization of two rigidization devices 1116, 1116'. In the example shown in FIG. 11A the rigidizing devices (endoscope 1116', overtube 1116), the venting valves 1139, 1139' and the one-way valves 1157, 1157' may be part of a disposable, e.g., single-use, component 1198, while the rest of the apparatus may be reusable.

FIG. 11B shows another example of a rigidizing pressure control system/sub-system configured for use with a pair of rigidizing members, including nested rigidizing members that are actuated by pressure. In FIG. 11B, the rigidizing pressure control system/sub-system 1100 is configured to control the pressure in a first rigidizing device and a second rigidizing device (not shown) that may couple to a first pressure interface 1182 and a second pressure interface 1183, respectively.

In FIG. 11B, the rigidizing pressure control system/sub-system includes a single gas supply (e.g., a reservoir of gas under positive pressure). The gas supply may be tank and/or may include a pump. Any of these apparatuses may also include a source or supply of negative pressure (e.g., when configured as a push-pull system, as described herein). In the example shown in FIG. 11B pressure sensors are shown distributed through the apparatus in order to monitor and provide control feedback for operation of the rigidizing pressure control system/sub-system. For example the fluid line connecting the gas supply 1179 to the regulator 1174 may include one or more pressure sensors. In FIG. 11B a pair of pressure sensors, P1 and P2, are shown for sensing the supply pressure 1162 from the gas supply 1179. As described above, the use of multiple pressure sensors may allow for redundancy and may enhance the safety of the rigidizing pressure control system/sub-system. For example, a fault may be detected if the two (or more) pressure sensors diverge significantly in sensed values. The regulator 1174 may regulate the pressure from the gas supply so that it may maintain a relatively constant pressure and/or flow, or at least a known pressure and/or flow. In FIG. 11B the gas supply may be part of the rigidizing pressure control system/sub-system and may be integrated with or separately connectable to the rigidizing pressure control system/sub-system.

In the example rigidizing pressure control system/sub-system shown in FIG. 11B, a second pressure sensor or pair of sensors may be connected to the regulator, downstream of the regulator. A pair of pressure sensors, P3 and P4, are shown in this example, configured to detect the working pressure 1164 from the regulator.

In the example shown in FIG. 11B a single pressure regulator may be connected to the gas supply and configured to regulate the input pressure into both the first and second rigidizing members. Although the pressure supplied to the first and second rigidizing members may be independently controlled and may be set to different pressures, the pressure achieved may be controlled based on the duration of time that the positive pressure is turned 'on' for each. In FIG. 11B parallel fluid paths are shown, a first, e.g., upper path 1192, for controlling pressure to rigidize the first rigidizing device connected to the first pressure interface 1182, and a second, e.g., lower, path 1193, for controlling pressure to rigidize the second rigidizing device connected to the second pressure interface 1183. The pressure interface may be a port, connecter, coupler, etc.

The first fluid path 1192 may include one or more (e.g., a pair of redundant) valves 1175 controlling flow through the first fluid path. These valves may be normally closed. The first fluid path 1192 may also include one or more valves controlling venting output 1176. These valves may be normally opened. As mentioned above, using a pair of valves in series (for the normally closed valves) or in parallel (for the normally open valves) may provide added safety and redundancy in the event of failure of one of the valves. Downstream of the valves and between the valves and the pressure interface 1182 is a second one or more pressure (or alternatively flow) sensors, shown as P5 and P6, configured to sense device pressure 1166.

The second fluid path 1193 is parallel to the first fluid path and may be configured similarly, e.g., including one or more (e.g., a pair of redundant) valves 1175' controlling flow through the second fluid path. These valves may be normally closed. The second fluid path 1193 may also include one or more valves controlling venting output 1176'. These valves may be normally opened. Downstream of the valves and between the valves and the second pressure interface 1183 is a second one or more pressure (or alternatively flow) sensors, shown as P7 and P8, configured to sense device pressure 1168.

The controller 1180 may receive input from each of the sensors and may control operation of the valves and regulator for the rigidizing pressure control system/sub-system 1100. The controller may include hardware, software and/or firmware, including one or more processors, for controlling rigidization of the first and/or second rigidizing device when coupled to the rigidizing pressure control system/sub-system. As used herein, a processor may include hardware that runs the computer program code. Specifically, the term 'processor' may be configured as a controller and may encompass not only computers having different architectures such as single/multi-processor architectures and sequential (Von Neumann)/parallel architectures but also specialized circuits such as field-programmable gate arrays (FPGA), application specific circuits (ASIC), signal processing devices and other devices. The controller may receive input from one or more additional sensors, including force sensors or the like. The controller may include control logic for performing any of the methods or procedures described herein.

In any of the apparatuses described herein one or more features may include redundancy by including multiples of various components. Redundant components may help avoid singe-fault failures. For example, redundant valves and/or sensors and or control logic apparatuses may be used so that no single component can cause pressure venting into the patient and the failure would be detected.

Any of these apparatuses may include a vent for de-rigidizing the device on either or both the proximal portion of the rigidizing device (e.g., handle) and/or on the rigidizing pressure control systems or sub-system. In some cases it may be beneficial to include venting for release of pressure on the proximal end of the device (e.g., handle) for mitigation of possible cross-contamination and/or for increasing the speed of de-rigidization. Testing of an apparatus such as that shown in FIGS. 1A-1B shows that venting from the handle as compared to the rigidizing pressure control systems or sub-system may be between 55-59% faster. This rate may be further improved using active de-rigidization, as described below.

As described elsewhere herein, any of these apparatuses may also be configured as push-pull regulators, and described in greater detail below, that may provide positive and negative pressure in various configurations to actively and more quickly control rigidizing/de-rigidizing. This may be done by the application of positive and negative pressure, or by just the application of positive pressure, to different sides of the bladder/compression layer within the rigidizing device(s). The controller may control the application of positive pressure and/or negative pressure to either or both the first side of the bladder layer and the second side of the bladder layer.

Figure 24A:
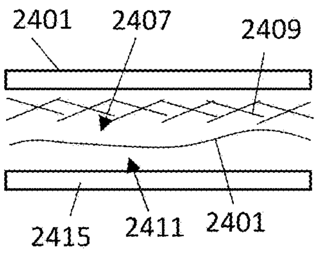
FIGS. 24A-24I illustrate push-pull control of the transition between the more flexible (less rigid) and less flexible (more rigid) states of the rigidizing devices described herein.
Figure 24B:
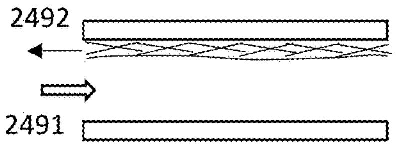
Figure 24C:
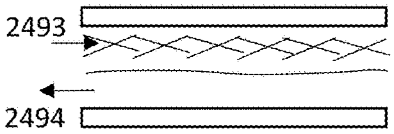
Figure 24D:
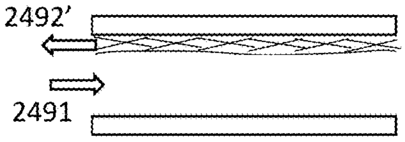
Figure 24E:
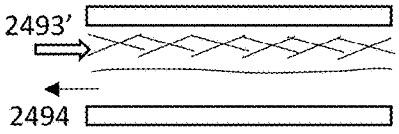

For example, FIGS. 24A-24I illustrate examples of push-pull control of the transition between the more flexible (less rigid) and less flexible (more rigid) states. For example, FIGS. 24A-24I illustrates an example of a partial section through an elongate rigidizable device similar to that shown in FIGS. 2A-2B and 3A-3B. The sections shown in FIG. 24A are repeated in FIGS. 24B-24L and include an inner layer 2415 that may be reinforced (e.g., by including one or more reinforming members, such as a helically arranged strip, ribbon or wire), a first gap 2411, a bladder/compression layer 2401, a rigidizing layer 2409, configured in this example as a braid layer, a second gap 2407 and an outer layer 2401. FIG. 24A shows the section through the elongate rigidizable device in a flexible (or more flexible) configuration, in which rigidizing layer 2409 is not compressed by the bladder layer 2401, but including a plurality of lengths of filament that are fee to move over each other. The elongate rigidizable device may be transitioned to the more rigid configuration, as shown in FIGS. 24B, 24D, 24F and 24H by the application of positive pressure 2491 to one side of the bladder (e.g., the side of the bladder opposite from the rigidizing layer), driving the bladder layer against the rigidizing layer, as shown. In some examples, e.g., FIGS. 24B and 24H, the second gap 2407, within which the rigidizing layer may move in the flexible configuration, may be passively vented 2492 to allow compression of the rigidizing layer against the inner layer 2415. Alternatively, in any of these examples this region may be actively vented 2492' by the application of negative pressure (e.g., vacuum) within this space, as shown schematically in FIGS. 24D and 24F. The rigidizing pressure control system/sub-system(s) described herein may include one or more connections (e.g. ports) connected to either or both the first side of the bladder layer (e.g., in communication with the first gap 2411 on the side of the bladder opposite from the rigidizing layer 2409 to apply positive and/or negative pressure. When converting from the more flexible configuration to the more rigid configuration, active venting of the second gap, e.g., the region within which the rigidizing layer 2409 resides, by applying negative pressure (e.g., suction) within this region in combination with the application of positive pressure to the opposite side of the bladder, e.g., in the first gap region 2411, as shown in FIGS. 24D and 24E. The application of both positive and negative pressure may be referred to here as push-pull actuation.

Figure 24F:
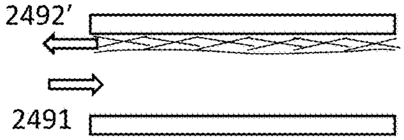
Figure 24G:
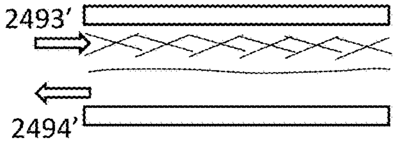
Figure 24H:
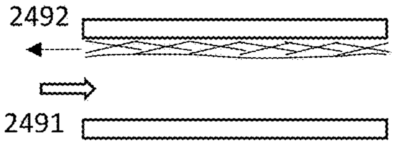
Figure 24I:
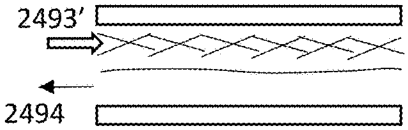

Any of these apparatuses and methods described herein, may use push-pull actuation, to rapidly and efficiently transition from the more rigid/less flexible configuration (e.g., from FIG. 24B or 24D), by either the application of active venting of the second gap while applying positive pressure on the opposite side of the bladder layer, e.g., in the first gap region. This is shown in FIGS. 24D and 24E, schematically illustrating the active venting while simultaneously applying positive pressure against the bladder layer. In FIG. 24C passive venting 2493 is used in the rigidization layer side of the bladder when de-rigidizing. In FIG. 24C passive venting 2494 is also used to release the pressure on the opposites side 2411 of the bladder layer. Passive venting may include opening a valve to allow venting to ambient pressure. Alternatively, in any of these methods and apparatuses active venting may be used, e.g., by applying pressure (positive pressure) 2493', e.g., to the rigidization layer side of the bladder 2407, to increase the speed of de-rigidizing, as shown in FIGS. 24E, 24G and 24I.

Any combination of active/passive venting of the rigidizing layer when rigidizing may be used; similarly any combination of active venting and passive venting may be used while de-rigidizing the device may be used. For example, FIGS. 24B and 24C illustrate a baseline example in which positive pressure is applied with passive venting. FIGS. 24D and 24E illustrate an example in which the apparatus may more rapidly switch from the more flexible to the more rigid configuration by the application of negative pressure before, during and/or after the compression of the rigidizing layer. In FIG. 24E the rigidizing apparatus may apply positive pressure 2493' to the rigidization layer side of the bladder to help separate rigidizing layer 2409 from the bladder layer 2401. In FIGS. 24F-24G the device may be transitioned from the flexible configuration to the rigid (e.g., more rigid) configuration by the application of active venting 2492' (instead of passive venting), in the gap holding the rigidizing layer. In this example, as shown in FIG. 24G, positive pressure 2493' may be applied to the bladder layer (gap 1) while the negative pressure 2494' (active venting) is applied in the first gap region on the opposite side of the bladder layer. When active pressure is applied, the active pressure (positive or negative) may be lower level of pressure than is applied when rigidizing (e.g., 5× lower, 10× lower, etc.) and may be applied as a brief pulse (e.g., <1 second, <0.75 seconds, <0.5 seconds, etc.). Following the active pressure, the valve(s) may be opened to ambient (e.g., room) pressure.

Any of these methods an applications may be used with just the application of just positive pressure to either or both sides of the bladder layer in a coordinated manner to more accurately and reliable transition quickly between the rigid and flexible configurations. In FIG. 24H, as in FIGS. 24B, positive pressure 2491 is applied while passively venting the rigidizing layer gap region. The device may be transitioned more quickly back to the more flexible configuration by applying pressurized gas (e.g., air, Nitrogen, etc.) to the second gap region containing the rigidizing layer while passively venting the opposite side of the bladder (e.g., the first gap between the bladder and the inner wall) as shown in FIG. 24I.

Relief Valves

As mentioned above, any of these apparatuses may include a relief valve, or may be configured to operate with a relief valve. The relief valve may be integrated into the rigidizing device, or it may be separable or separate from the rigidizing device. In some examples the relief valve is configured as an accessory component that may be used to provide a relief path if pressure in the body lumen (e.g., colon) exceeds a threshold pressure, such as the pressure used for insufflation.

Figure 12A:
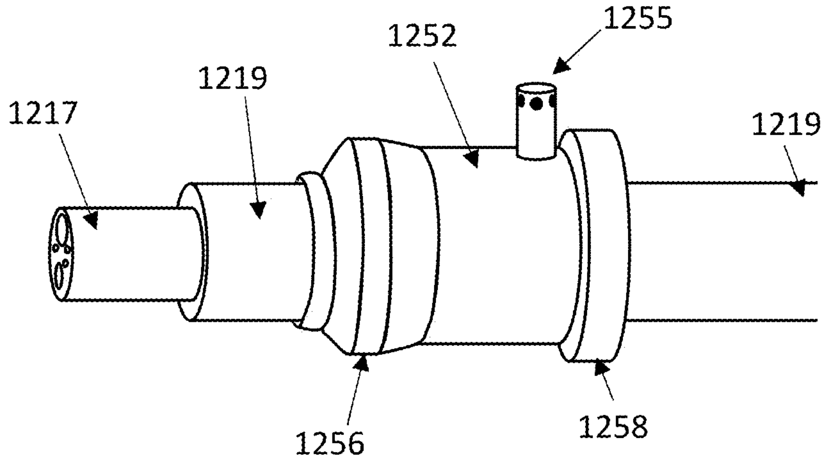
FIG. 12A illustrates one example of a relief valve component that may be used with a rigidizing device; in this example the relief valve is configured as part of a sleeve through which the rigidizing device passes.
Figure 12B:
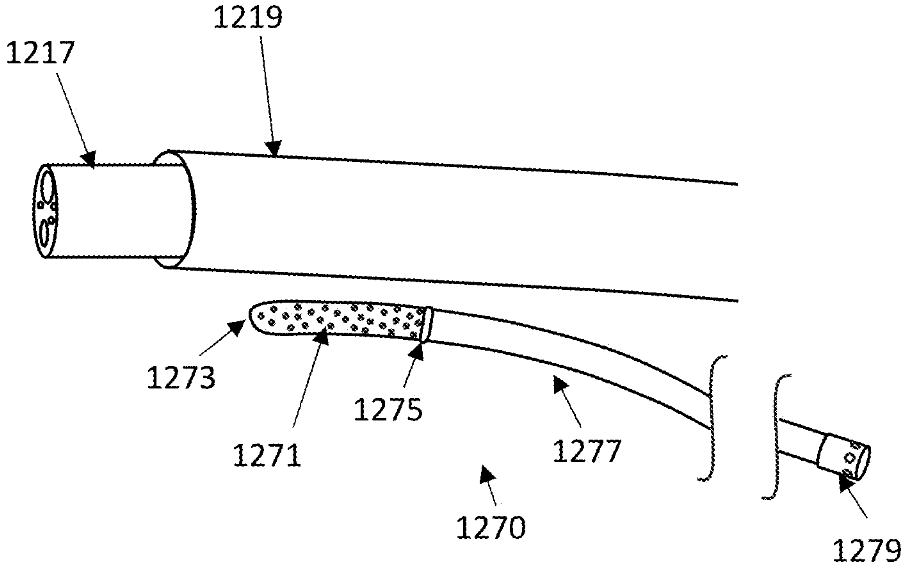
FIG. 12B illustrates an example of a relief valve component that may be used with a rigidizing device; in this example the relief valve is a separate assembly that may be used with (and coupled to) the rigidizing device.

FIGS. 12A and 12B illustrate examples of relief valve devices that may be used. For example, in FIG. 12A the relief valve is configured as a sleeve or sheath that fits over the proximal end region of one or more (e.g., a pair of nested) rigidizing devices. In FIG. 12A the relief valve includes a cannula body 1252 having a retaining rim or ridge 1256 and a sealing flange 1258. The sealing flange may be larger (e.g., may have a larger diameter) and may seal against the anus. The cannula body also includes a valve 1255 and passes over a rigidizable device configured as an overtube 1219 that at least partially surrounds a rigidizing device configured an inner endoscope 1217. In this example the cannula body may be configured to span the patient's anus when used, so that the proximal end (to the left, in FIG. 12A) resides within the rectum, while the sealing flange seals the device within the anus. The distal end region includes a gap or space between the outer surface of the overtube 1219 and the inner surface of the cannula body, allowing gas to be expelled through this region and out of the relief valve 1255 as shown.

FIG. 12B shows another example of a relief valve device configured as a relief valve cannula that may be used with any of the rigidization devices described herein. In FIG. 12B, a nested pair of rigidizing devices 1217, 1219 are shown alongside a relief valve accessor device configured as a relief valve cannula 1270. The cannula includes a channel into which gas may pass from the distal end (shown having a plurality of openings 1271 near the atraumatic distal tip 1273), and into the channel lumen of the relief valve cannula 1277 before exiting through one-way relief valve 1279. The openings 1271 at the distal end may be sufficiently sized so as to pass gas from out of the body region around the rigidizing device without blocking or passing solid material. In some examples the relief valve accessory may have a semi-rigid body that can be intubated into the anus, but may remain sufficiently flexible to follow the path into the sigmoid. In some examples, the relief valve accessory may stay in the anus while the endoscope/overtube traverses the colon.

Any of the rigidizing devices described herein may be adapted for use with a relief valve as shown in FIG. 12A or 12B. In some examples the rigidizing member may be formed as a concentric tube within the elongate body of the rigidizing device (not shown).

Cross-Contamination Mitigation

Figure 13:
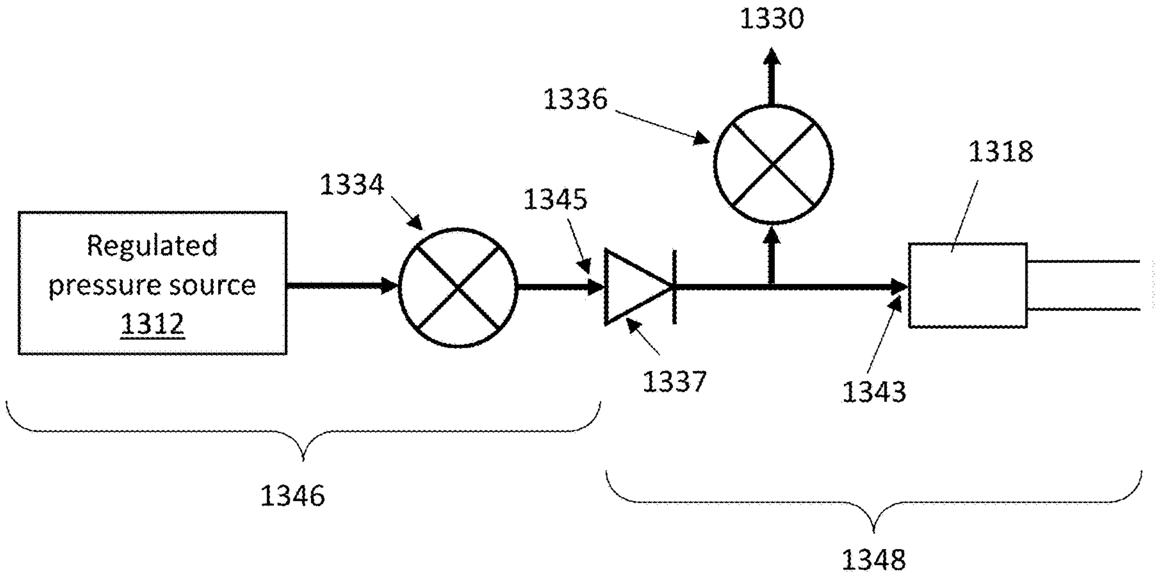
FIG. 13 schematically illustrates an example of an apparatus configured to prevent cross-contamination between a re-usable rigidizing pressure control system/sub-system and an interface sub-system coupled to or integrated with a rigidizing device.

Any of the apparatuses described herein may be configured to prevent, reduce or eliminate cross-contamination between the (reusable) rigidizing pressure control systems or sub-systems and the rigidizing device, which may be single-use or limited use (with cleaning or the use of a protective sheath). For example, FIG. 13 illustrates, schematically, an apparatus including a reusable rigidizing pressure control system/sub-system 1346 and a rigidizing device (e.g., endoscope and/or overtube) 1348. The rigidizing pressure control system/sub-system includes a regulated pressure source 1312, a controller (not shown), a supply valve 1334 and a pressure line, which connects to a pressure inlet 1345 of the rigidizing device. In this example the rigidizing device includes an interface sub-system with a check valve 1337 in fluid communication with the pressure inlet and a rigidizing pressure inlet 1343 gating access into the bladder/compression layer(s) of the rigidizing device 1318. A vent 1330 (including a disposable valve 1336, such as, but not limited to a pinch valve) may also be included. It is particularly helpful that the vent is coupled with or integrate into the proximal end (e.g., proximal handle) of the rigidizing device(s) as shown, so that pressurized fluid (e.g., air)

venting out of the rigidizing device(s) may be released away from the reusable rigidizing pressure control system/sub-system 1346 by more than 12 inches (2 feet, 3 feet, 4 feet, 5 feet, etc.) to prevent cross-contamination. For example, if a hole develops on the rigidizing device (e.g., endoscope or overtube), the rigidizing pressure control system or sub-system system could become contaminated, and this contamination could be introduced to the next patient with whom the rigidizing pressure control system/sub-system is used.

Figure 14:
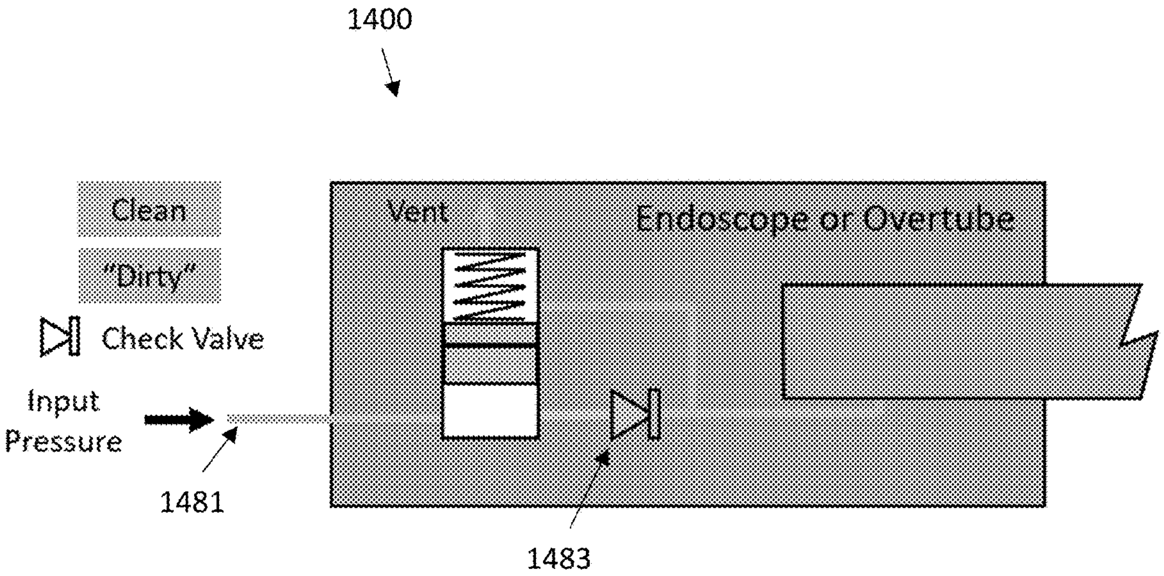
FIG. 14 schematically illustrates one example of an interface sub-assembly for a rigidizing device that may limit or prevent cross-contamination.
Figure 15A:
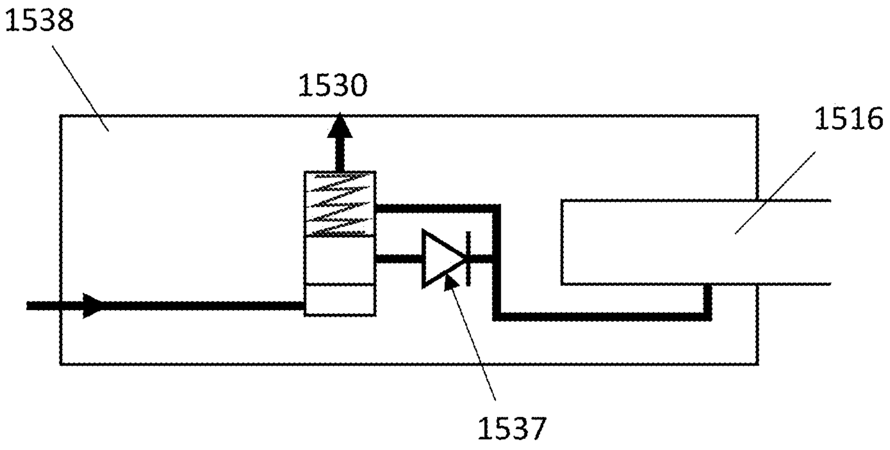
FIGS. 15A-15B schematically illustrate operation of one example of an interface sub-assembly for a rigidizing device that may limit or prevent cross-contamination.
Figure 15B:
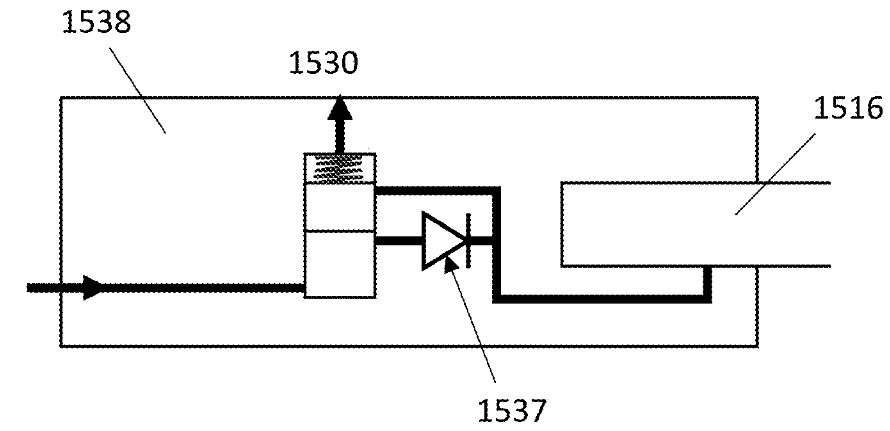

Thus, any of these apparatuses may be configured so that the pressurized air from the robotic rigidizing device(s) vents into the room via a port in the rigidizing device and does not vent near (and contaminate) the capital rigidizing pressure control system/sub-system. In the schematic shown, a check valve 1337 may prevent contaminated fluid (e.g., gas) from contacting (and contaminating) the rigidizing pressure control system/sub-system. In some examples, as shown in FIGS. 14 and 15A-15B below, the controller may close/open the vent port via a pressure driven valve while staying uncontaminated. This can be performed with both 2 way and 3 way valves.

For example, FIG. 14 shows an example of an interface sub-system. The interface subsystem 1400 may include an inlet 1481 connecting to the pressure source (e.g., to the pressure line of the rigidizing pressure control system/sub-system), which connects to the two-way (or in some examples, 3-way) valve that include a chamber in which a displaceable plug is biased, e.g., by a spring, down into the lower chamber region leaving the vent path open so that pressurized fluid (e.g., air) from the rigidizing device may pass through the valve and out of the vent; the contaminated ("dirty") fluid is prevented from passing into the lower chamber and out to the rigidizing pressure control system/sub-system by the one-way valve 1483. However, when pressurized fluid from the regulated pressure source ("clean" fluid) is delivered to rigidize the device, the fluid passes through the valve and through the one-way valve 1483 into the rigidizing device, as shown. The pressure of the fluid may drive the plug element within the valve up, expanding the lower chamber and cutting off the vent pathway. This is illustrated in FIGS. 15A-15B.

In FIG. 15A the interface sub-system is shown integrated into a proximal end region of the rigidizing device 1516. In some cases the interface sub-system may be coupled to (but separable from) the rigidizing device. For example, the handle body 1538 of the interface sub-system may couple to the rigidizing device 1516 so that the vent 1530 is on the handle body. In FIG. 15A the 2-way valve is oriented so that the connection to the rigidizing pressure control system/sub-system is closed by the bias (e.g., spring) of the valve, and the valve path is open. The valve includes a one-way valve 1537. In FIG. 15B, pressure from the rigidizing pressure control system/sub-system displaces the valve (acting against the bias) to close the vent path, but open the rigidizing pressure path, allowing the positive pressure to rigidize the device. Thus, in some examples when input pressure is applied from the rigidizing pressure control system/sub-system, the head loss in the vent pathway is large enough for the valve to build up pressure and close the vent. In the case of a three-way valve design, when input pressure is applied from the rigidizing pressure control system/sub-system, the valve may first close the vent pathway, and then open the pathway to the device.

In addition to preventing cross-contamination, in some examples venting into the room from the handle region, rather than from the rigidizing pressure control system/sub-system may speed up the rigidizing/de-rigidizing.

Figure 16A:
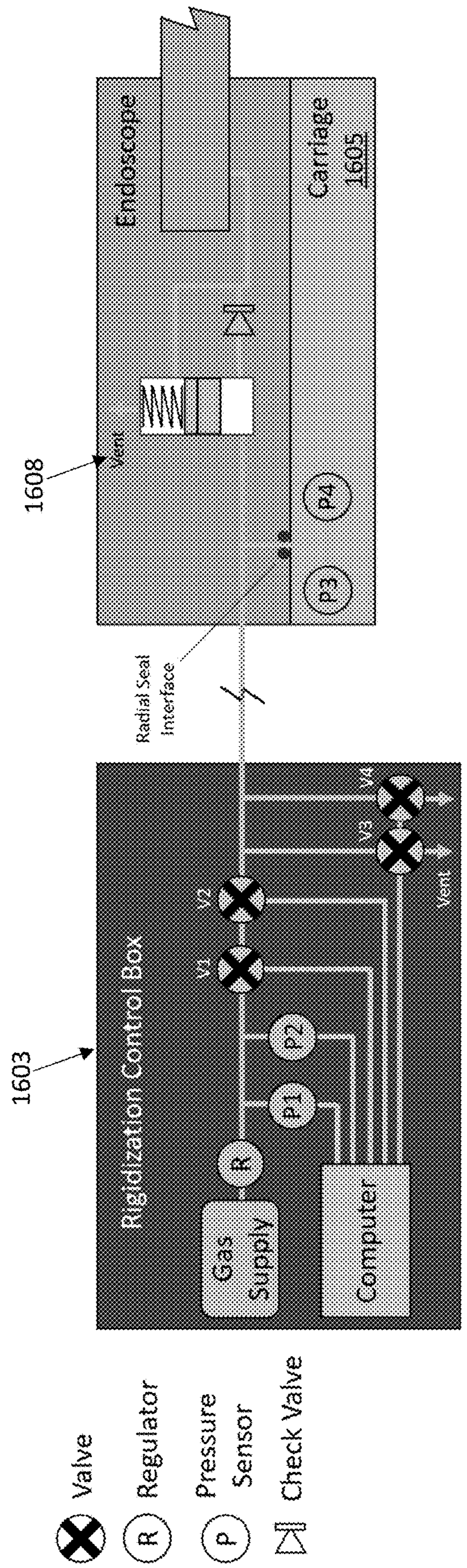
FIG. 16A schematically illustrates an apparatus including both an interface sub-assembly for a rigidizing device and a reusable pressure controller (e.g., rigidizing pressure control system or sub-system). In this example the pressure line pressure sensors are in the carriage.
Figure 16B:
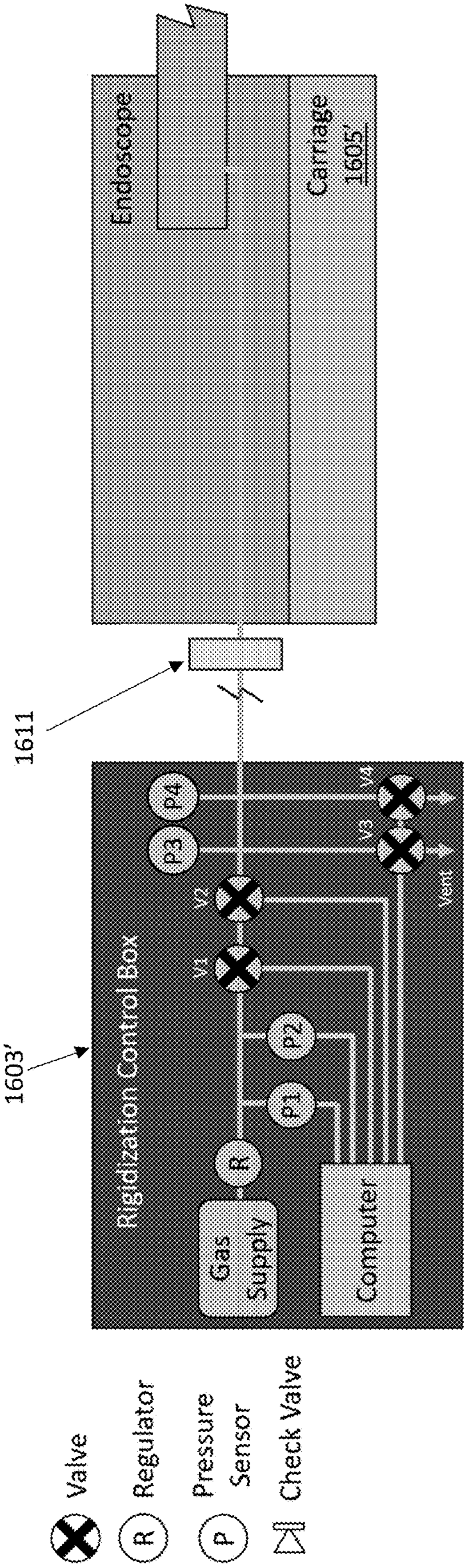
FIG. 16B schematically illustrates another example of an apparatus including both an interface sub-assembly for a rigidizing device and a reusable pressure controller (e.g., rigidizing pressure control system or sub-system). In this example the pressure line pressure sensors are in the rigidization control box.

FIGS. 16A and 16B schematically illustrates an example of a system including both a rigidizing pressure control system/sub-system 1603, 1603' and the rigidizing device (endoscope) with or coupled to an interface sub-system 1605, 1605'. In FIG. 16A the handle ('carriage') of the rigidizing device, configured as an endoscope in this example, includes a the 3-way valve, one-way valve and vent, as part of the carriage region. A pressure line connects the inlet to the rigidizing pressure control system/sub-system. The pressure line is clean" and only the vent side of the valve 1608 is exposed to potentially contaminated fluid (e.g., air) from the scope. The rigidizing pressure control system/sub-system includes many of the components described above, including redundant sensors and valves. Including the valve in the handle as shown here or in FIGS. 15A-15B may significantly reduce the derigidization time, e.g., by up to 300 ms or more, depending on the starting pressure(s).

In FIG. 16A the pressure line pressure sensors (P3 and P4) are within the handle (cartridge) region 1605, coupled through a sealing interface. In FIG. 16B the pressure line sensors are instead within the rigidization control box 1603'. In FIG. 16A the handle (cartridge) portion includes a vent 1608, this vent is optional; any of the apparatuses described herein may or may not include this vent. For example, the variation shown in FIG. 16B does not include a vent but instead includes a filter 1611 between the rigidization control box 1603' and the one or more rigidizing members (in FIGS. 16A and 16B a single rigidizing member, e.g. endoscope, is shown). The filter and fluid line connecting the rigidizing member to the rigidization control box may be single use, and/or disposable.

Thus, any of these apparatuses may include one or more filters between the rigidizing pressure control system/sub-system and the rigidizing device to filter the vented fluid (e.g., air). Any appropriate filter may be used, such as, but not limited to, a 0.2 micron filter, 0.1 micron filter, etc. Thus, a filter on the pressure line may prevent contamination of the rigidization control box 1603, 1603', as mentioned. In some cases, although the use of a filter may reduce the speed of the rigidization/de-rigidization, due to increased head loss, the apparatuses described herein, including the control circuitry controlling operation of the rigidization, may account for the effects on the filter on the pressure profile.

Tube Routing Assembly

Any of the apparatuses and methods described herein may include a fluid line routing assembly, referred to herein as a tubing router or tube router assembly. FIGS. 17A-17D illustrate one example of a tubing router (tubing router device) and FIGS. 18A-18B illustrate an example of a handle region of a rigidizing device including and using a tubing routing assembly. This assembly may assist in transferring fluid (in this examples, pressurizing fluid to rigidize/de-rigidize, but generically any fluid including gasses and liquids) to the rigidizing device(s) between a relatively stationary source of fluid and the rolling/rotating rigidizing member. For example, a fluid router may be used to transfer pressurized fluid between the rigidizing pressure control system/sub-system and the rolling/rotating rigidizing member. In the absence of a tubing router assembly as described herein, the connection between the rigidizing pressure control system/sub-system and the rolling/rollable rigidizing member (and particularly the pressure input port in fluid communication with the bladder/compression layers(s)) may instead need to be a rotary seal or the like, which may have a higher friction moment and may require a larger diameter. Alternatively, a clock-spring design may be used, but may require a large volume of space for relatively large ranges of motion, and the tubing may be exposed to snagging leading to resistance and inconsistent torque when rolling the rigidizing device.

In contrast, the tube routing assemblies described herein may minimize the friction in the rotary joint and may therefore minimize the rigidizing/de-rigidizing time. These assemblies may also have a relatively small footprint, which may be helpful when integrating them into a handle of the rigidizing device, as shown in FIGS. 18A-18B.

Figure 17A:
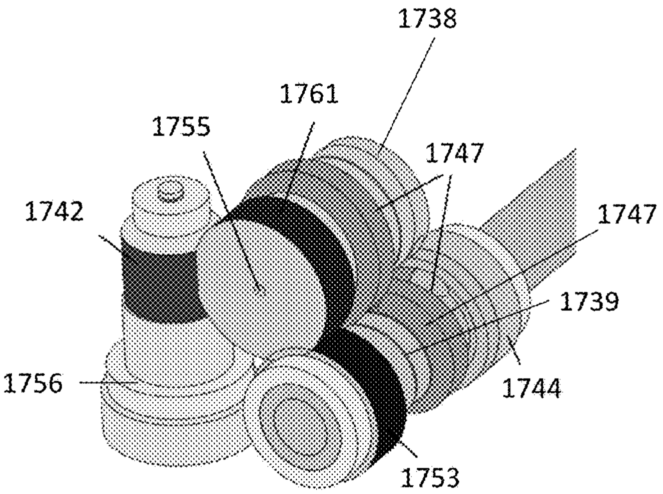
FIGS. 17A-17D show an example of a tube routing assembly (e.g., tube router) as described herein.
Figure 17B:
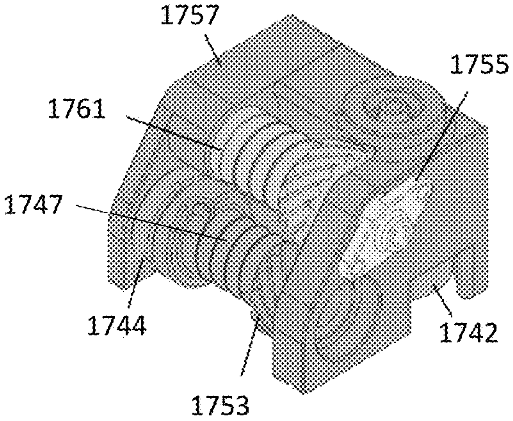
Figure 17C:
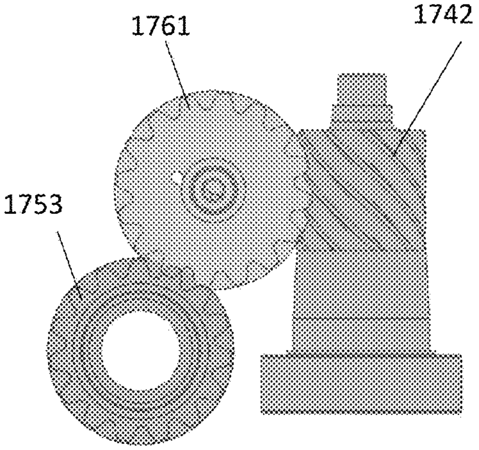
Figure 17D:
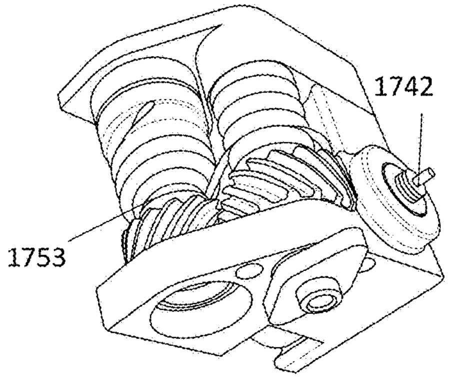
Figure 18A:
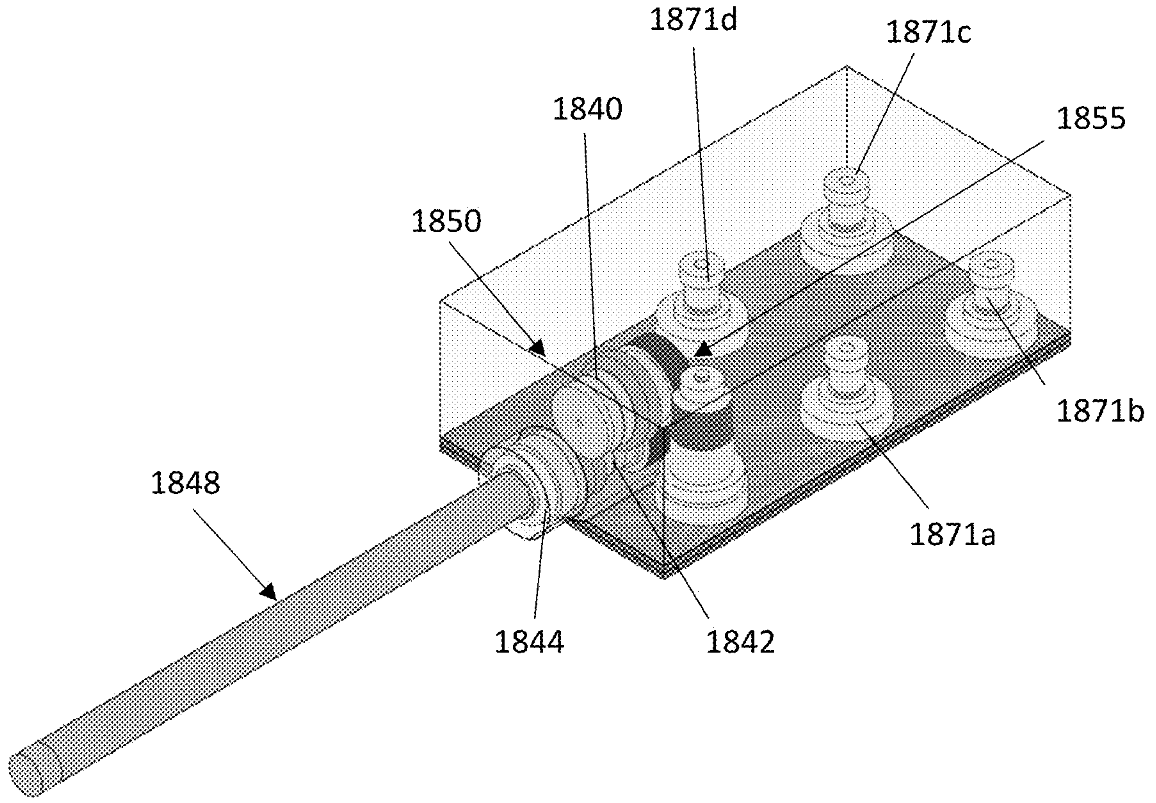
FIGS. 18A-18B show schematic illustrations of a tube routing assembly integrated into a handle portion of a rigidizing device.
Figure 18B:
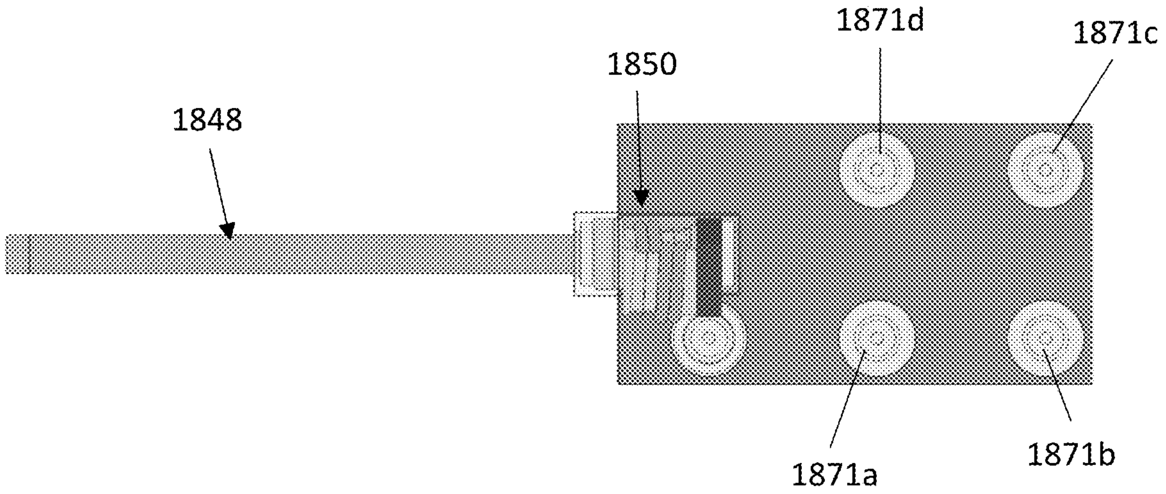

For example, FIG. 17A illustrates a tube routing assembly including a first spool 1738 rigidly connected to (or integral with) an idler drivetrain mechanism (shown in this example as a gear) 1761, a second spool 1739 rigidly connected to (or integral with) an output drivetrain mechanism (e.g., output gear) 1753. The assembly also includes an input drivetrain mechanism 1742 (e.g., input gear) driving rotation of the first spool, and multiple bearings 1756 between the spools. The device also includes a tubing line 1747 configured to wind around and between the first spool and the second spool as the input drivetrain mechanism is driven in a clockwise or a counterclockwise rotation, and a fluid input 1755 (configured as a rotary seal) that is also coupled to the first spool and in fluid communication with a lumen of the tubing line. Further, the assembly also includes a fluid output coupled to the second spool and in fluid communication with the lumen of the tubing line. FIG. 17B shows another top perspective view. FIG. 17C shows a side view, and FIG. 17D show a right side perspective view. Although the examples shown in FIGS. 17A-17D and 18A-18B show the drivetrain mechanism as gears, any appropriate drivetrain mechanism may be used, including (but not limited to friction wheel, cable, belt, etc.).

In the example shown in FIGS. 17A-17D the tubing line 1747 is shown as a single tubing line. However, this configuration is not limited to a single tubing line (e.g., single pathway) but may include multiple tubing lines, which may be arranged in tandem or concentrically. For example, a plurality of tubing lines may be arranged next to each other on the spools and/or nested within each other. This configuration may allow for simultaneous routing of multiple lines, e.g., from the handle to the rigidizing device(s) using the same tube routing assembly. Examples of other lines may include air lines (for insufflation, for balloon inflation, etc.), suction/aspiration lines, fluid delivery lines (e.g., saline lines, etc.), etc. Alternatively or additionally, multiple fluid routers may be used. In general a fluid router as described herein may be useful for transferring fluid between a first device (such as an endoscope, etc.) and a second device having a stationary or alterative frame of movement.

As mentioned, any of these apparatuses may be included in the handle portion of a steerable rigidizing device 1848. For example, the tubing router assembly 1850 may be within a housing of the handle region (proximal end region) of the apparatus. In FIGS. 18A and 18B, the proximal end of the rigidizing device 1848 is engaged with an output adapter seal 1844 so that the rigidizing device rotates (rolls) with the second spool 1842, which in turn rotates with the first spool 1840 as the assembly. The bladder/compression layer(s) are therefore coupled, via a rigidizing pressure inlet (e.g., rigidizing input port 1855), to receive pressurized fluid (e.g., air) from the first spool, through the tubing, and back out of the output seal/adapter of the second spool. In FIGS. 18A and 18B the housing also includes multiple tendon drivers 1871*a, b, c, d* and any of these tendon driver or the tubing router assembly may include a limiter or limiters to prevent over-rotation (and possible) damage.

In general, any of the apparatuses (and methods of using them) described herein may be used with, or as part of, a catheter, an endoscope (including, but not limited to colonoscopes, bronchoscope, colposcope, cystoscope, esophagoscope, gastroscope, laparoscope, thoracoscope, enteroscope, etc.), overtube, etc. These apparatuses and methods may be used with a robotic system, including a robotically controlled endoscope. Robotic systems may advance, withdrawn/retracted, moved back and forth, and/or steered robotically. In some examples, the robotic system may control the operation (e.g., advancing, retracting, and/or actuating) of one or more tools to be used within an external working channel, including any of the tools or tool pairs described herein. Any of the apparatuses described herein may be used with a robotic system, including a robotic endoscope system.

Robotic Apparatuses

Figure 19:
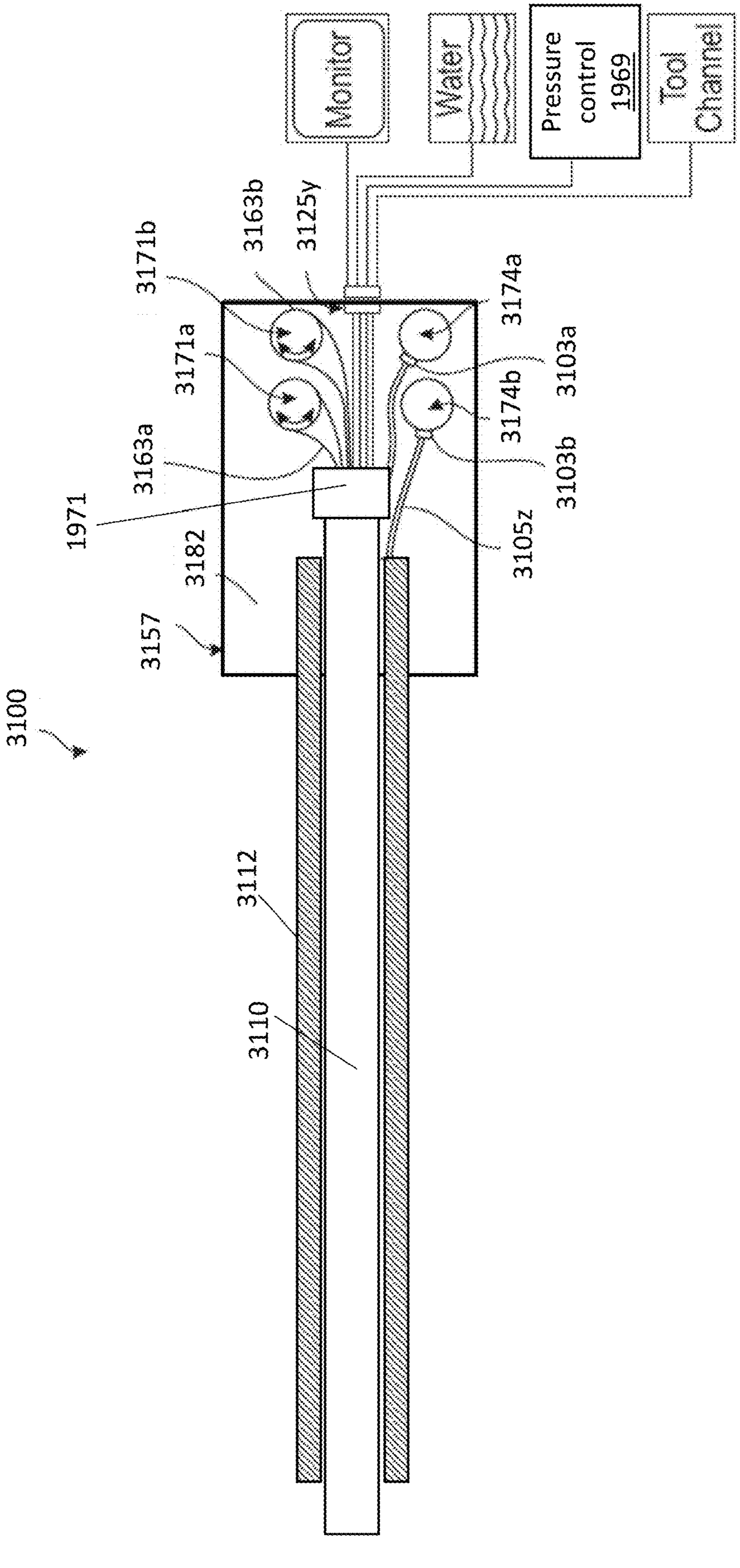
FIG. 19 illustrates an example of a robotic system including a tube routing assembly and a rigidizing pressure control system/subsystem as described herein.

As mentioned above, the rigidizing apparatuses described herein may be configured as part of a robotic system or for use with robotic apparatuses. In some examples the rigidizing device including any of these features may be configured as an outer tubular member that is robotically controlled, e.g., configured as a robotically controlled overtube and/or endoscope assembly. FIG. 19 shows an exemplary apparatus 3100, including a rigidizing device configured as an overtube 3112; the system may optionally include an inner endoscope 3110. The overtube and inner endoscope can be separately or collectively be robotically controlled or manipulated (e.g., steering, movement, rotation, etc. including in some examples, rigidizing). The overtube and inner endoscope may be configured as illustrated in any of the examples described above, and may have the same general construction, or may be of different constructions. As shown in FIG. 19, the outer overtube 3112 and the inner endoscope 3110 may be terminated together into a common structure, such as a handle or cassette 3157 which may include a housing 1382. The outer overtube 3100 can be movable with respect to the endoscope 3110 by rotation of one or more driver mounted to the cassette 3157. The system may include actuators 3171*a*, 3171*b* that may connect to cables 3163*a*, 3163*b* respectively, to steer (e.g., bend or deflect) the tip of the endoscope 3110 (and/or outer overtube 3112). Other steering mechanisms (e.g., pneumatics, hydraulics, shape memory alloys, EAP (electro-active polymers), or motors) are also possible. The cassette 3157 can further include bellows 3103*a*, 3103*b* that may connect to the pressure gap of the endoscope 3110 and the overtube 3112, respectively to drive fluid through pressure lines 3105*z*, in variations for either the endoscope and/or the overtube that are configured to rigidize when pressure is applied. As shown in this example, the cassette 3157 can include eccentric cams 3174*a*, 3174*b* to control bellows 3103*a*, 3103*b*. Alternatively, one or more linear actuators can be configured to actuate the bellows. As another alternative, the devices can be rigidized and de-rigidized through one or more pumps or pressure sources (e.g., via pressure line 3105*z*). The system may include one or more inlets/ports 3125*y*.

In the example shown in FIG. 19 both a tube routing assembly 1971 and a pressure rigidizing pressure control system/sub-system 1969 may be included, or integrated for use with, these systems. The tubing routing assembly may function as described above; as the flexible elongate rigidizing device rolls, the tubing spools between the first spool and the second spool without significantly increasing friction, allowing limited clockwise/counterclockwise movement.

Pressure Control

The apparatuses and methods described herein may improve the speed and safety of the operation of dynamically rigidizing devices that may transition between rigid and flexible configurations by applying a positive pressure (or in some examples, negative pressure) to rigidize a rigidizing layer of the rigidizing device. The rate at which a rigidizing device that is made rigid by the application of pressure may be enhanced by the application of a pulse of pressure having a relatively high (as compared to the target pressure for rigidizing the device) pressure with a rapid on and off time, e.g., an overpressure pulse. As described above in reference to FIG. 7, the higher the pressure of the pulse to be applied (e.g., the regulator pressure), the faster the rigidizing device will reach the target pressure. This may also allow for shorter duration pressure pulses to be applied.

In general, the target pressure for the rigidizing device may be more quickly achieved by overpressurizing the applied pulse of pressure. The target pressure may be set (e.g., preset) and/or may be adjusted or adjustable by the user, either continuously or from a selectable list of pressures. For example the system (e.g., the rigidizing pressure control system/sub-system) may include a user input for receiving or selecting the target pressure for one or more rigidizing devices. The amplitude of the pulse of pressure may generally be set to be greater than the target pressure. For example, the pressure of the pulse of pressure may be 105% or greater, 110% or greater, 115% or greater, 120% or greater, 125% or greater, 130% or greater, 135% or greater, 140% or greater, 145% or greater, 150% or greater, 200% or greater, etc. than the target pressure.

Similarly, the duration of the pulse of pressure may be selected and/or adjusted (e.g., automatically by the system) so that the final pressure within the rigidizing device is approximately the target pressure. As the overpressure pulse is applied to the rigidizing device, the bolus of pressurized fluid is distributed though the compression region (defined by the compression layer/bladder layer) to achieve the final pressure within the rigidizing device; this final pressure may approximate the target pressure and is less than the pulse pressure upon equilibration of the pressure within the rigidizing device. The application of the pulse may be completed before the pressure in rigidizing device is equilibrated. In the examples described herein the rigidizing medium, e.g., the fluid being pressurized, is a compressible fluid, such as air or another gas (e.g., carbon dioxide, nitrogen, etc.).

Any of these apparatuses may include one or more sensors for detecting pressure and/or flow within the rigidizing pressure control system/sub-system and/or within the rigidizing device(s). In some examples the sensed data may be used as feedback to control and/or monitor the operation of the applied pressure. For example, the rigidizing pressure control system/sub-system may monitor the applied pressure and/or the ongoing pressure within the system and/or within the rigidizing device. Pressure may be used to detect and/or respond to potential leaks, as will be described in greater detail below, or it may be used to modulate the applied pressure. In some examples the rigidizing pressure control system/sub-system may confirm that the target pressure has been achieved after applying the pulse of rigidizing pressure and/or that the device has been de-rigidized (if applying pressure in the opposite polarity to de-rigidize the device); the control logic may be configured to apply one or more additional pulses, which may be shorter duration, in order to titrate the final pressure within the rigidizing device. In general, these apparatuses may also coordinate the application of pulses of pressure to rigidize/de-rigidize multiple rigidizing devices, including nested devices.

In general, the application of a pulse of overpressurized rigidizing medium (e.g. fluid) may shorten the time to rigidize significantly. Table 1, below, shows examples of measured time for a rigidizing device (e.g., in this example, a rigidizing overtube) that is fully rigidized with a target pressure (e.g., positive pressure) of 4 atmospheres. A variety of overpressurized pulses having a pulse pressure of between 5-8 atmospheres were applied to rigidize the device. As shown in Table 1, the time to fully rigidize (e.g., the time to achieve the 4 atm target pressure) decreased significantly as the pressure of the applied pulse of pressure increased from 5-8 atm. The applied pressure is referred to as the regulator pressure.

TABLE 1

| Commanded Valve Opening Timings | |
|---|---|
| Regulator Pressure atm | Rigidization time ms |
| 5 | 514 |
| 6 | 335 |
| 7 | 280 |
| 8 | 240 |

The data in Table 1 was measured by sensing pressure at the vent outlet of the rigidizing pressure control system/sub-system and within the rigidizing device. If the pressure of the applied pressure pulse is applied at approximately the target pressure (e.g., 4.06 atm, the time to fully rigidize the rigidizing device is greater than 1 second. The duration of the pulse must be set to be greater than this time in order to allow the rigidizing device to equilibrate to the target pressure. Rigidization may refer to the time to reach the target pressure (e.g., 4 atm for an overtube in this example). Therefore, in the above case, an over pressurization pressure burst (from the baseline case of 4.06) was able to speed the rigidization time by over four-fold (e.g., 4×).

The speed at which the rigidizing devices rigidize may be particularly important when using multiple rigidizing devices, and in particular when using nested rigidizing devices, such as the robotic system as illustrated in FIGS. 1B, 4 and 5A-5B. In these cases, the system may be alternately rigidizing and de-rigidizing the nested rigidizing devices often and quickly in order to maneuver the robotic apparatus in real time. Thus, the ability to rapidly (within less than 1 second, less than 0.7 seconds, less than 0.6 seconds, less than 0.5 seconds, less than 0.4 seconds, less than 0.3 second, less than 0.2 seconds, etc.) transition between flexible and fully rigid states may allow lag-free, fast and efficient operation of the robotic tool.

The methods and apparatuses described may also apply pressure to de-rigidize any of these rigidizing devices. For example, in apparatuses that use positive pressure to rigidize, negative pressure may be used to more quickly de-rigidize the apparatus, e.g., reducing the de-rigidization time. In some examples, de-rigidization may be passive, e.g., by opening or venting the rigidizing device (e.g., the compression region) to atmosphere. Passive de-rigidizing time may be, e.g., around 0.9 to 0.7 seconds (e.g., 0.8 seconds). Any of these apparatuses may be considered de-rigidized when the pressure (e.g., when the difference in pressure between the compression region and the room pressure) drops below 0.05 atm. With active de-rigidization a pressure (e.g., negative pressure/vacuum when positive pressure used to rigidize, positive pressure when negative pressure is used to rigidize) may be applied to more quickly de-rigidize the rigidizing device. In general, active de-rigidization, such as the application of a vacuum may result in an increase in the rate of de-rigidization by greater than 20-50% or more across all scenarios tested, for example, this increase in de-rigidization speed was seen even when the apparatus was vented at the handle rather than just at the rigidizing pressure control system/sub-system.

Active de-rigidization may include the application of an evacuation pulse. This evacuation pulse may be applied to the same inlet as the overpressure rigidizing pulse, or to a different inlet. For example, in rigidizing devices that use positive pressure to rigidize, active de-rigidization may include the application of a brief pulse of negative pressure to more rapidly de-rigidize the device. The same rigidizing pressure control system/sub-system may coordinate both the rigidizing pulse and the evacuation pulse. For example, an evacuation pulse (de-rigidizing pulse) of vacuum may be applied to the rigidizing device in the rigid state. The magnitude of the evacuation pulse may be, e.g., between −0.1 atmosphere and −1 atmospheres (e.g., between −0.2 atmospheres and −1 atmospheres, between −0.3 atmospheres and −0.9 atmospheres, etc.). The negative pressure applied during the pulse may be constant or it may vary; for example the peak negative pressure applied may be between −0.1 atmospheres and −2.0 atmospheres, etc. In some examples, the rigidizing pressure control system/sub-system may include or couple to a source of negative pressure for de-rigidizing the device(s), such as a plenum holding a vacuum. A large plenum may be fluidly connected to the rigidizing pressure inlet, and the evacuation pulse could effectively stay at the minimum vacuum pressure (e.g., −0.82 atm) in order to maximize the pressure differential pulling the rigidization medium (e.g., air) out of the device. In some examples a vacuum pump may be used to apply pressure.

The evacuation pulse may have a duration that is set (e.g., preset) or adjustable. In some cases the evacuation pulse may have a duration that is between 0.2 seconds and 0.8 seconds (e.g., between 0.2 seconds and 0.7 seconds, between 0.2 seconds and 0.6 seconds, between 0.2 seconds and 0.5 seconds, etc.). The evacuation pulse duration may be adjusted based on feedback from one or more sensors (e.g., pressure sensors), including one or more pressure sensors in communication with the compression region of the device.

Figure 20:
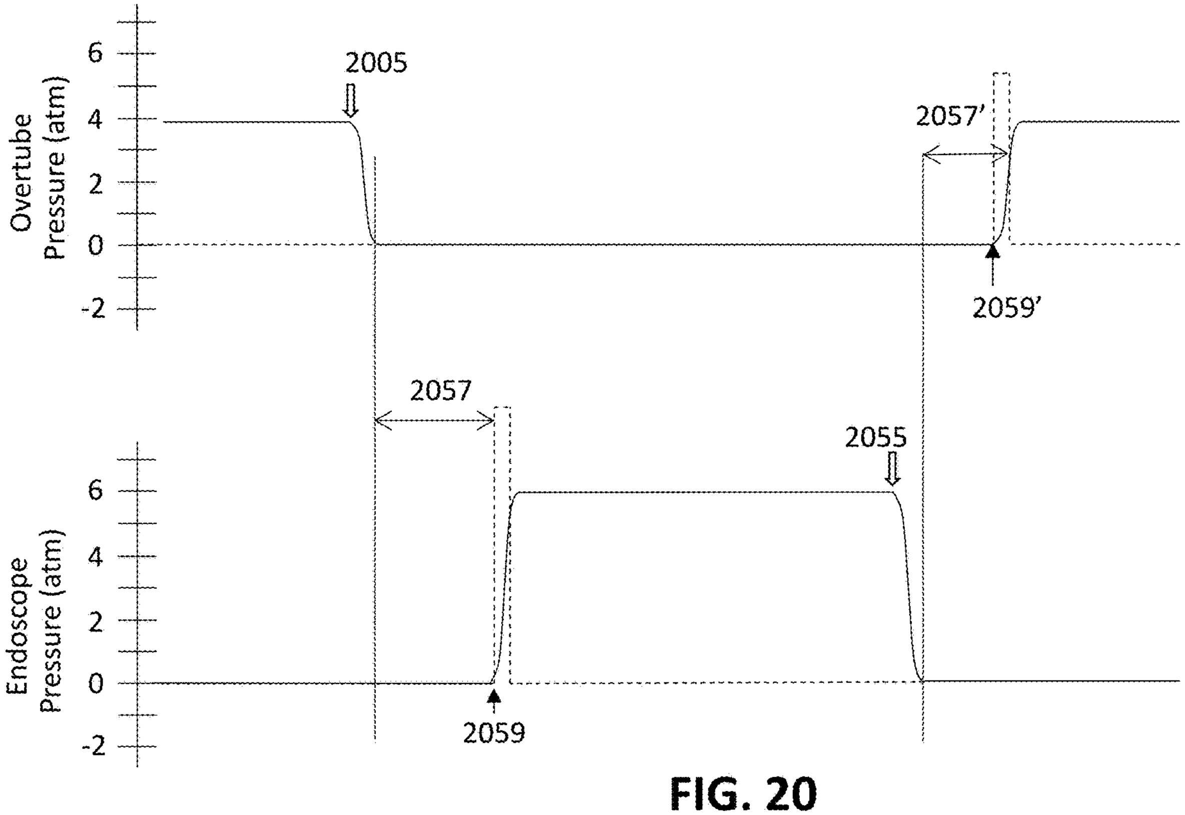
FIG. 20 shows an example of a state diagram for operation of a robotic apparatus including a nested pair of dynamically rigidizing devices in which the first rigidizing device (e.g., endoscope) and the second rigidizing device (e.g., overtube) are alternately rigidized by a pulse pressure with a delay between de-rigidizing of one and rigidizing of the other resulting in an intermediate dwell period in which both rigidizing devices are in a flexible state.
Figure 21:
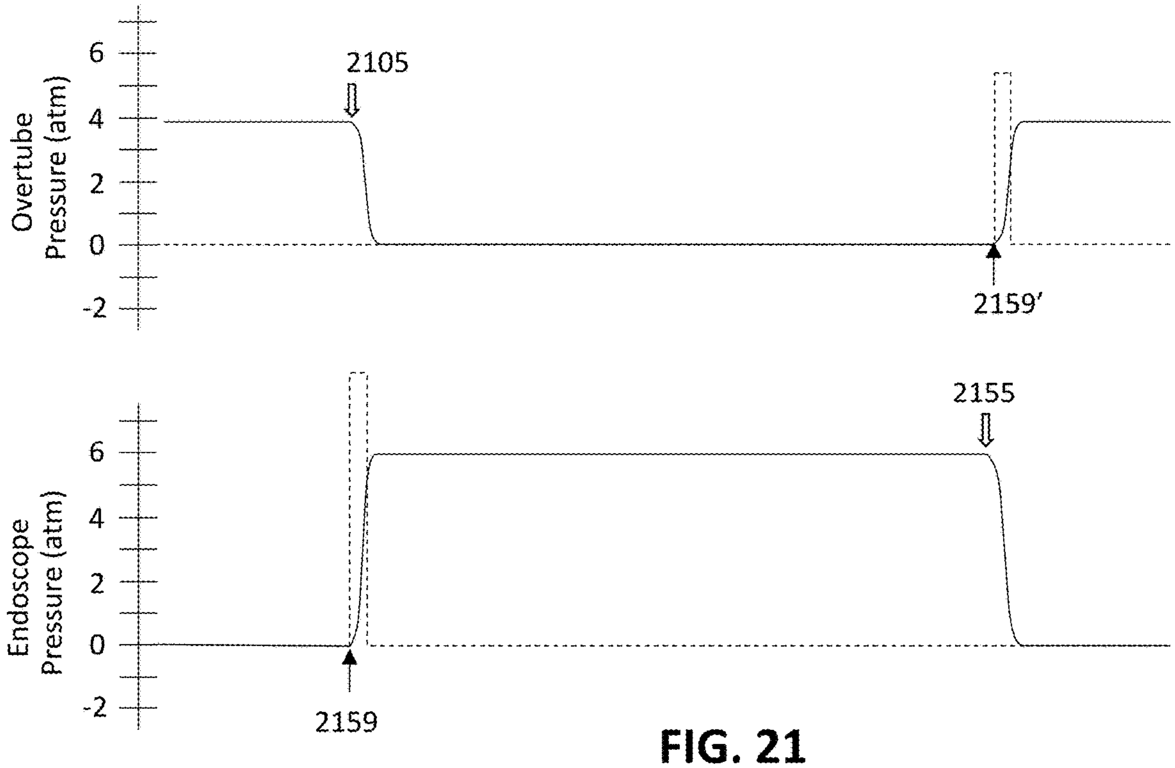
FIG. 21 shows an example of a state diagram for operation of a robotic apparatus including a nested pair of dynamically rigidizing devices in which the first rigidizing device (e.g., endoscope) and the second rigidizing device (e.g., overtube) are alternately rigidized by a pulse pressure so that de-rigidizing of one and rigidizing of the other are driven simultaneously.

Thus, the apparatuses and methods described herein may apply pulses of pressure either or both to rigidize and to de-rigidize the rigidizing device. In particular, these apparatus and methods may be configured to coordinate the application of one or more pulses of pressure to coordinate operation of a system having multiple rigidizing devices. For example, the apparatus may include a rigidizing pressure control systems or sub-system that is configured to coordinate, e.g., automatically or semi-automatically, the application of pulse of pressure to alternatively rigidize and de-rigidize a nested pair of rigidizing devices. FIGS. 20-23 illustrate examples of state diagrams (showing the approximate pressure over time) for a pair of nested rigidizing devices. In this example a rigidizing endoscope is nested within a rigidizing overtube (see, e.g., FIGS. 1B, 4 and 5A-5B). In some examples, the apparatus (e.g., the rigidizing pressure control systems or sub-system) may be configured to provide a brief intermediate dwell period between de-rigidization of a first rigidizing device and rigidizing of the second rigidizing device, so that both of the rigidizing devices are in a flexible state during the intermediate dwell period, as shown. In FIG. 20 the top trace shows the pressure vs. time relationship for the outer (overtube), while the lower trace shows the pressure vs. time relationship for the inner (endoscope). Initially, the overtube is shown in the rigid configuration, with a rigidizing pressure, e.g., within the compression region/bladder, of approximately 4 atmospheres. The user (manually) or the system (automatically) may indicate a transition from the rigid overtube to a rigid endoscope, e.g., in order to advance or maneuver the overtube relative to the endoscope, and thus, the rigidizing pressure within the overtube may be release or removed to release the pressure 2005. The overtube pressure may then fall to ambient pressure. Note that the pressure shown on the y-axis is pressure relative to ambient pressure. Thereafter, following an intermediate dwell period 2057, a pulse of pressure (e.g., positive pressure that is over pressured, e.g., 8 atm) may be applied 2059 to rapidly rigidize the endoscope. The endoscope in these examples is rigidized to a higher level than the outer endoscope (e.g., 6 atm vs. 4 atm for the overtube). The apparatus may calculate and/or apply the brief duration (e.g., 0.3 sec) of the rigidizing positive pressure pulse 2059 and the device may prevent leak to maintain the pressure at the target pressure, as shown in FIG. 20. Thereafter, the rigidizing pressure control systems or sub-system may release the pressure 2055 in the compression region/bladder of the endoscope, e.g., by opening a vent and/or by applying an evacuation pulse of negative pressure. A second intermediate dwell period 2057' may then occur before rigidizing the outer overtube by applying a pulse of positive pressure 2059'. The controller of the rigidizing pressure control systems or sub-system may determine and/or adjust the duration of the intermediate dwell periods. In some cases, the intermediate dwell period may be reduced so that the overtube and endoscope are alternately transitioned between the rigid configurations and the flexible configurations simultaneously or nearly simultaneously (e.g., concurrently), as shown in FIG. 21.

In FIG. 21, the overtube is initially rigidized (e.g., to a rigidization pressure of about 4 atmospheres). The pressure maintaining the rigid configuration of the overtube may be released 2105 at approximately the same time that a pulse of pressurized fluid is applied to rigidize the endoscope 2159. The apparatus may then similarly transition (e.g., automatically or upon input from the user) the endoscope from the rigid configuration to the flexible configuration and transition the overtube from the flexible to the rigid configuration by simultaneously applying the pressure pulse to the overtube 2159' while releasing (actively or passively) the pressure from the endoscope 2155.

Figure 22:
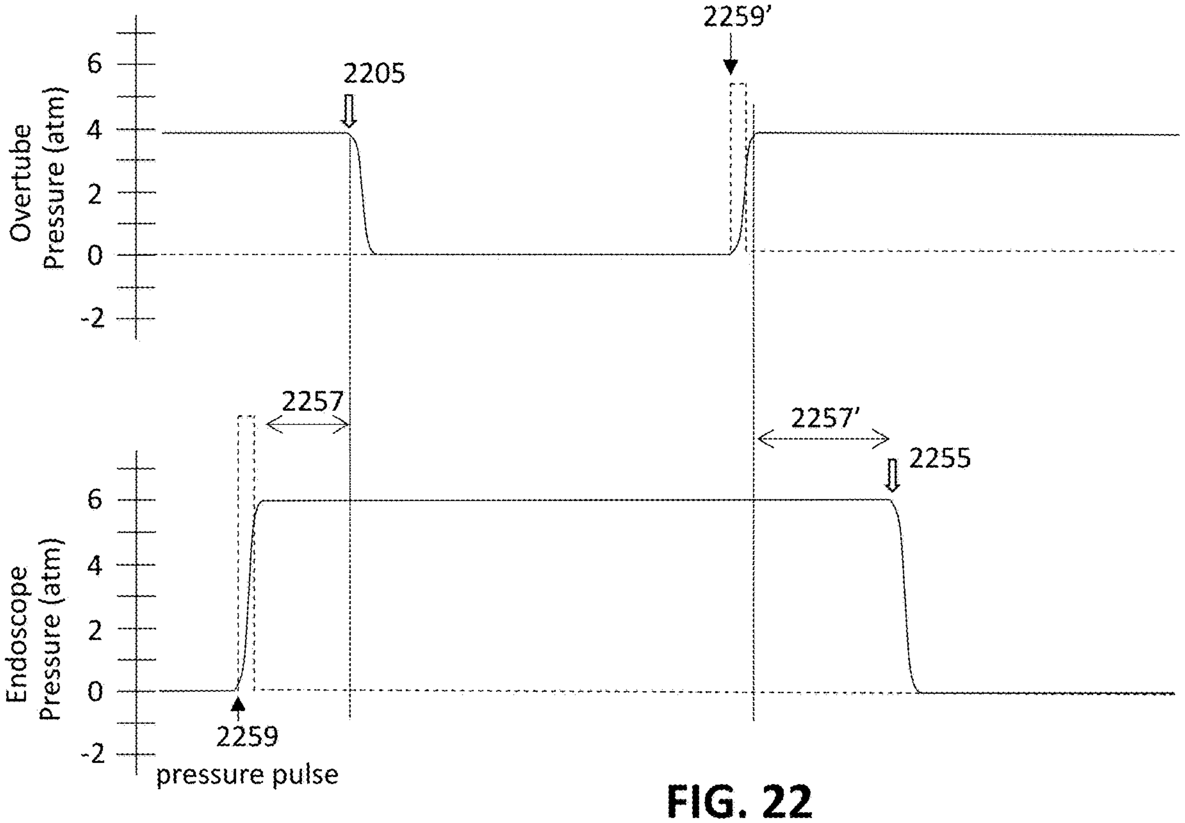
FIG. 22 shows an example of a state diagram for operation of a robotic apparatus including a nested pair of dynamically rigidizing devices in which the first rigidizing device (e.g., endoscope) and the second rigidizing device (e.g., overtube) are alternately rigidized by a pulse pressure with a delay so that rigidizing of one overlaps with de-rigidizing of the other, resulting in an intermediate dwell period in which both rigidizing devices are in a rigidized state.
Figure 23:
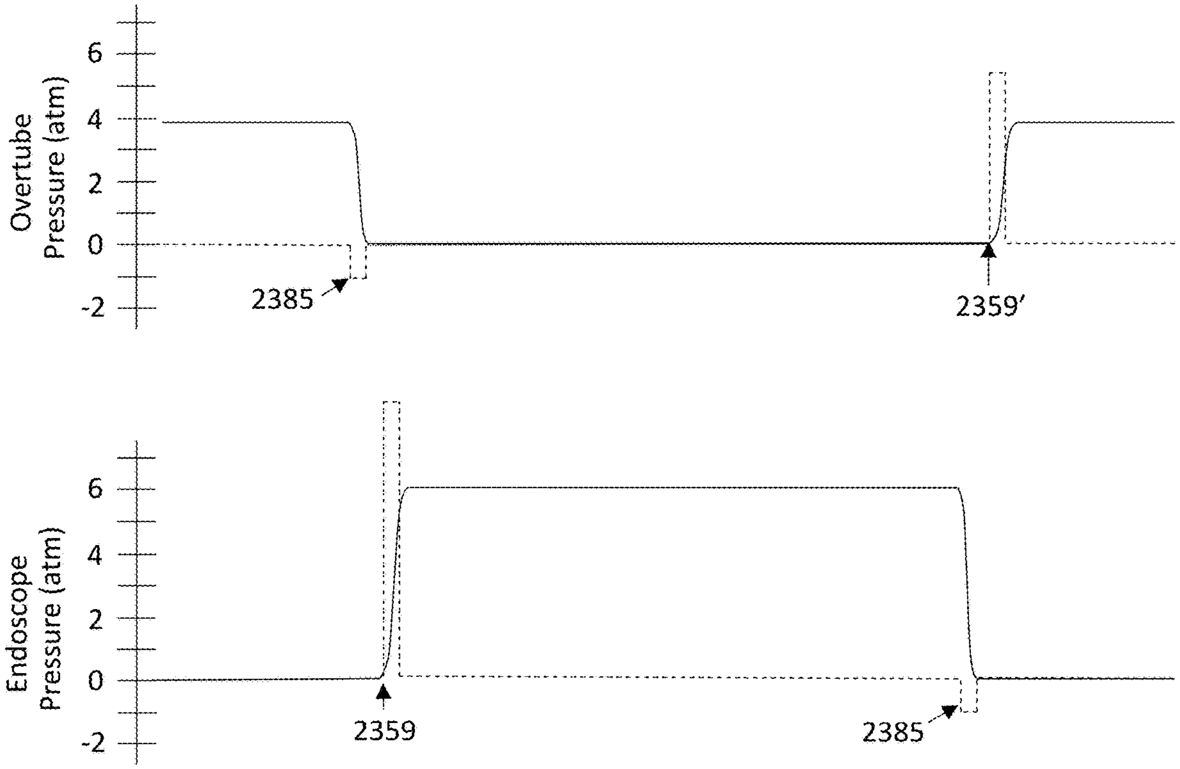
FIG. 23 shows an example of a state diagram for operation of a robotic apparatus that is operated similarly to FIG. 21, in which de-rigidizing performed or assisted by the use of a pulse of negative pressure (e.g., a negative evacuation pressure pulse).

In some cases it may be preferred to include an intermediate dwell period in which both the outer device (e.g., overtube) and the inner device (e.g., endoscope) are both rigid when alternating between rigid/flexibles states of the overtube and endoscope. Thus, the rigidizing pressure control systems or sub-system may control the application of pressure pulses to rigidize and the release of pressure (active or passive) to achieve a desired intermediate dwell time, as shown in FIG. 22. In this example, the overtube is initially rigidized (at 4 atmospheres); prior to de-rigidizing the overtube, the rigidizing pressure control systems or sub-system may apply a pulse 2259 of positive pressure (over-pressurized, e.g., to 8 atm, which is 130% of the target pressure of 6 atm) to rapidly rigidize the endoscope to pressurizing the endoscope's compression region/bladder to approximately 6 atm. Following an intermediate dwell period 2257, the rigidizing pressure control systems or sub-system may then release the pressure from the overtube 2205 so that the overtube is de-rigidized. After a desired amount of time, the rigidizing pressure control systems or sub-system may then again rigidize the overtube 2259' by applying an overpressurized pulse of pressure (e.g., pressurized to approximately 5.3 atm, which is 130% of the target pressure of 4 atm), and after a second intermediate dwell time 2257' may de-rigidize the endoscope 2255 by actively or passively venting the pressurized fluid from the endoscope compression region/bladder. Allowing at least a momentary rigid dwell period (e.g., 0.5 seconds or less, 0.4 seconds or less, 0.3 seconds or less, 0.2 seconds or less, 0.1 second or less, etc.) may help stabilize the operation and relative movement of the outer and inner rigidizing members when maneuvering a nested rigidizing system. In general the pulses described herein are transient, and may be referred to as transient pulses. Typically, these transient pulses may be square pulses, e.g., turning on a rapidly as possible, e.g., by opening a valve or valves, then turning off, however, any 'shape' pulse may be used (e.g. rectangular/square pulses, ramped pulses, etc.).

As mentioned above, in any of these apparatuses and methods active evacuation of a rigidized rigidizing device may be used. For example, the rigidizing pressure control systems or sub-system may apply a pulse of negative pressure to de-rigidize a rigid device more quickly. This is illustrated in the state diagram shown in FIG. 23. In this example the overtube is initially in a rigid state, pressurized to approximately 4 atmospheres. The overtube may be de-rigidized by the application of a pulse of negative pressure (e.g., an evacuation pulse) 2385. The rigidizing pressure control systems or sub-system may concurrently, or with a predetermined rigid dwell period or flexible dwell period, rigidize the endoscope by applying a pulse of overpressurized positive pressure 2359. Similarly, the rigidized endoscope may thereafter be actively de-rigidized by the application of a negative evacuation pressure 2385, before, while or after the overtube is rigidized by the application of an overpressurized positive pressure pulse 2359'. In FIGS. 20-23, the dashed lines schematically illustrate the pulses of pressure applied. The x-axis in these figures is a time axis, which may not be shown to scale.

In general, the rigidizing pressure control systems or sub-system may coordinate the application of rigidizing pressure pulses and the active or passive evacuation of pressure for one or more (including nested) rigidizing devices with a high degree of accuracy. An intermediate dwell period may be a rigidized dwell period, in which both rigidizing devices are simultaneously rigid. The intermediate dwell period may be a flexible dwell period, in which both rigidizing devices are simultaneously flexible. The rigidizing pressure control systems or sub-system may set or adjust the duration of any dwell periods.

As mentioned above, the profiles shown in FIGS. 20-23 may vary depending on the properties of the fluid (air) pressurized circuit. For example, in some cases, including a filter in one or more of the lines may result in a change in the rate of pressure change and in some cases may result in overshoot. In general, the methods and apparatuses described herein may account for these effects and adjust the applied pressure to accommodate.

Leak Prevention and Limitation

The apparatuses described herein may detect and respond to the loss of rigidizing medium and/or may be configured to protect the patient from a loss of rigidizing medium. In general, these apparatuses may include one or more pressure and/or flow sensors, and in particular may include multiple and/or redundant pressure/flow sensors. As described in reference to FIGS. 2A-2B and 3A-3B, any of the rigidizing devices described herein may include one or more escape or leak pathways that may extend continuously along the length of the rigidizing device to provide an outlet at a proximal end of the device, e.g., out of an escape port. The escape port may be, e.g., an opening in the handle or other proximal region that vents to atmosphere. In some cases the escape pathway and/or escape port may be monitored by one or more sensors, which may detect and/or quantify any leakage through the escape pathway. For example, an amount of leaked gas (e.g., leak volume) may be continuously tracked and may be used to trigger an alert to the user when it exceeds one or more predetermined levels. For example, if the total leakage volume is greater than or equal to a leak volume threshold, e.g., 50 $cm^3$ (e.g., 60 $cm^3$, 70 $cm^3$, 75 $cm^3$, 80 $cm^3$, 90 $cm^3$, 100 $cm^3$, 125 $cm^3$, 150 $cm^3$, 200 $cm^3$, etc.). Once the alert is emitted, the user may determine that venting of the surrounding lumen (e.g., using an internal channel of the device, by applying suction, etc.) may be performed or the alert may be ignored for a longer period of time. The threshold volume threshold may be predetermined or set, or it may be adjusted by the user or derived (e.g., from the patient size). The apparatus (e.g., the controller) may be configured may be monitor and emit one or more alerts.

In general, any of the apparatuses described herein may include sensors on or withing the rigidizing device, including one or more pressure sensors in fluid communication with the compression region (e.g., bladder), in fluid communication with a region around or adjacent to the compression region, including the escape pathway, and/or in fluid communication with a region outside of the rigidizing device. Sensors may be included at or near the distal end region, one or more regions along the length of the rigidizing device, and/or at a proximal end region of the device. For example, the apparatuses described herein may include a working channel through the device; the working channel may be in fluid communication with the external environment at the distal end region of the device. Thus any of these apparatuses may include one or more sensors (e.g., pressure sensors) in fluid communication with a distal end region of the device that may be controlled (e.g., by the rigidizing pressure control systems or sub-system) to sense pressure outside of the device. The apparatus (e.g., rigidizing device) may be configured to apply a jut of fluid (e.g., saline, air, etc.) through the working channel for a period before sensing the pressure. For example, the apparatus may include a connection (valved connection) to couple a source of fluid to the working channel and the rigidizing pressure control systems or sub-system may control the application of fluid through the working channel in order to verify that the channel is open and/or to clear the channel so that an accurate pressure measurement may be taken. In some examples the apparatus may apply a jet of fluid (e.g., air) periodically, such as every 30 seconds, to verify that the fluid can flow into colon through the working channel. Pressure readings after fluid is applied may therefore accurately reflect the pressure at the distal end region. The flow of fluid (e.g., air, liquid, etc.) may drive out a blocking material and clear the pathway to the outside region. Pressure measurements may be taken periodically (e.g., every 1-5 seconds, every 4-10 seconds, every 10-20 seconds, every 1-30 seconds, etc.) and thus fluid may be driven through the channel periodically, prior to sensing the pressure. For example, if pressure is sensed periodically, fluid may be flushed through the channel periodically to clear the channel and a pressure may be sensed immediately or shortly thereafter (e.g., after waiting 1 second or some other delay time) and/or while applying the fluid. An uncleared blockage may be detected by the system as a high pressure, which may trigger a fault or alert.

In general, any of these apparatuses may include one or more pressure sensors on the outside of the device, including at the device tip. The pressure sensor may be on or in communication with the outside of the device, including in communication with a working channel, as just described, or a washing channel configured to apply fluid to wash or clear the window of an imaging (e.g., camera) sub-system.

Any of these sensors may communicate with the rigidizing pressure control systems or sub-system, which may use the data provided to identify and respond to a leak of rigidizing medium from the rigidizing device. The sensor and/or the control system may include processing, including filtering (e.g., high frequency filtering) for the sensor data.

These methods and apparatuses may therefore determine and monitor the pressure outside of the device, including in some examples the intracolonic pressure. Thus, the system may be configured to determine if the pressure within the outside environment exceeds a threshold, and may further determine if the high pressure is due to a leak from the rigidizing device or from another source, including an insufflation source.

The rigidizing pressure control systems or sub-system may analyze the data (or may transmit to a separate processor for analysis) and may use this data to determine if the device is leaking or holding pressure, and may determine the extent to which a leak is occurring. This information may be transmitted and/or stored, including alerting a user. The determined leak information may also or alternatively be used in one or more control processes to respond to a sensed leak. For example, the system may determine if it should transmit or emit an alert (audible, visual, etc.) based on the magnitude of the leak and in some cases the pressure of the surrounding region (e.g., patient body region). In some examples, if the sensed leak, which may be detected as a loss of pressure within the compression region of the device when the device is in the rigid state, exceeds a first leak threshold (e.g., comparing the change in pressure over time, or rate of change, with the threshold), but is less than a second (higher) leak threshold, and optionally the rigidizing pressure control systems or sub-system confirms that the pressure outside of the device (e.g., intracolonic pressure) does not exceed a threshold, indicating that the leak is not likely to change the external pressure substantially, then the apparatus may optionally emit an alert, may store the event for later review and may apply one or more supplemental pressure pulses (of relatively lower magnitude and brief duration) to maintain the rigidizing pressure within the device.

In some cases if the rigidizing pressure control systems or sub-system determines that the sensed leak exceeds the first leak threshold and is greater than the second (higher) leak threshold, then the system may emit the alert and optionally may shut down the rigidization components of the apparatus, and may vent all of the rigidizing devices. In cases where the sensed pressure outside of the device (e.g., intracolonic pressure) exceed a threshold, the system may shut down the rigidization components of the apparatus, venting the rigidizing devices.

In any of these apparatuses, the pressure sensed (within the device and/or outside of the device) may be monitored, stored and/or may be displayed to the user.

All publications and patent applications mentioned in this specification are herein incorporated by reference in their entirety to the same extent as if each individual publication or patent application was specifically and individually indicated to be incorporated by reference. Furthermore, it should be appreciated that all combinations of the foregoing concepts and additional concepts discussed in greater detail below (provided such concepts are not mutually inconsistent) are contemplated as being part of the inventive subject matter disclosed herein and may be used to achieve the benefits described herein.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like. For example, any of the methods described herein may be performed, at least in part, by an apparatus including one or more processors having a memory storing a non-transitory computer-readable storage medium storing a set of instructions for the processes(s) of the method.

While various embodiments have been described and/or illustrated herein in the context of fully functional computing systems, one or more of these example embodiments may be distributed as a program product in a variety of forms, regardless of the particular type of computer-readable media used to actually carry out the distribution. The embodiments disclosed herein may also be implemented using software modules that perform certain tasks. These software modules may include script, batch, or other executable files that may be stored on a computer-readable storage medium or in a computing system. In some embodiments, these software modules may configure a computing system to perform one or more of the example embodiments disclosed herein.

As described herein, the computing devices and systems described and/or illustrated herein broadly represent any type or form of computing device or system capable of executing computer-readable instructions, such as those contained within the modules described herein. In their most basic configuration, these computing device(s) may each comprise at least one memory device and at least one physical processor.

The term "memory" or "memory device," as used herein, generally represents any type or form of volatile or non-volatile storage device or medium capable of storing data and/or computer-readable instructions. In one example, a memory device may store, load, and/or maintain one or more of the modules described herein. Examples of memory devices comprise, without limitation, Random Access Memory (RAM), Read Only Memory (ROM), flash memory, Hard Disk Drives (HDDs), Solid-State Drives (SSDs), optical disk drives, caches, variations or combinations of one or more of the same, or any other suitable storage memory.

In addition, the term "processor" or "physical processor," as used herein, generally refers to any type or form of hardware-implemented processing unit capable of interpreting and/or executing computer-readable instructions. In one example, a physical processor may access and/or modify one or more modules stored in the above-described memory device. Examples of physical processors comprise, without limitation, microprocessors, microcontrollers, Central Processing Units (CPUs), Field-Programmable Gate Arrays (FPGAs) that implement softcore processors, Application-Specific Integrated Circuits (ASICs), portions of one or more of the same, variations or combinations of one or more of the same, or any other suitable physical processor.

Although illustrated as separate elements, the method steps described and/or illustrated herein may represent portions of a single application. In addition, in some embodiments one or more of these steps may represent or correspond to one or more software applications or programs that, when executed by a computing device, may cause the computing device to perform one or more tasks, such as the method step.

In addition, one or more of the devices described herein may transform data, physical devices, and/or representations of physical devices from one form to another. Additionally or alternatively, one or more of the modules recited herein may transform a processor, volatile memory, non-volatile memory, and/or any other portion of a physical computing device from one form of computing device to another form of computing device by executing on the computing device, storing data on the computing device, and/or otherwise interacting with the computing device.

The term "computer-readable medium," as used herein, generally refers to any form of device, carrier, or medium capable of storing or carrying computer-readable instructions. Examples of computer-readable media comprise, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed.

The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein.

The processor as described herein can be configured to perform one or more steps of any method disclosed herein. Alternatively or in combination, the processor can be configured to combine one or more steps of one or more methods as disclosed herein.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under", or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

In general, any of the apparatuses and methods described herein should be understood to be inclusive, but all or a sub-set of the components and/or steps may alternatively be exclusive and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A system for rigidizing an elongate rigidizing device at a target pressure, the system comprising:
- a pressure line configured to couple to a pressure inlet of the elongate rigidizing device;
- a pressure sensor configured to detect pressure;
- a vent valve in fluid communication with the pressure line;
- a supply valve in fluid communication with the pressure line;
- a controller configured to apply a high-pressure pulse of pressurized fluid from a source of pressurized fluid through the pressure line to rigidize the elongate rigidizing device, wherein the high-pressure pulse has a pressure that is higher than the target pressure to rigidize the elongate rigidizing device, further wherein the controller is configured to determine a leak rate and to automatically provide one or more additional pulses of pressurized fluid if the leak rate is greater than a first threshold but less than a second threshold, and trigger an alert if the leak rate is greater than the second threshold.

2. The system of claim 1, wherein the controller is configured to apply the high pressure pulse of the pressurized fluid for less than 1 second.

3. The system of claim 1, wherein the controller is configured to apply the high pressure pulse of the pressurized fluid at between 2 atmospheres and 10 atmospheres.

4. The system of claim 1, wherein the controller comprises a control circuitry configured to determine the leak rate and to provide the one or more additional pulses of the pressurized fluid.

5. The system of claim 4, wherein the one or more additional pulses of the pressurized fluid are less than 200 milliseconds.

6. The system of claim 4, wherein the control circuitry is configured to open the vent valve to de-rigidize the elongate rigidizing device.

7. The system of claim 1, further comprising the source of the pressurized fluid, wherein the source of the pressurized fluid comprises a pressurized reservoir.

8. The system of claim 1, wherein the pressurized fluid is a gas.

9. The system of claim 1, wherein the pressurized fluid is a compressible fluid.

10. The system of claim 1, wherein the supply valve is configured to be opened by the controller.

11. The system of claim 1, further comprising a second pressure line configured to couple to a second elongate rigidizing device, a second pressure sensor in fluid communication with a distal end region of the second pressure line, a second vent valve proximal to the second pressure sensor, and a second supply valve proximal to the second vent valve and in fluid communication with the second pressure line, wherein the controller comprises a pressure manifold and is configured to selectively apply the one or more additional pulses of the pressurized fluid through the pressure line or the second pressure line.

12. The system of claim 1, wherein the controller is configured to apply a de-rigidizing pulse of pressure to de-rigidize the elongate rigidizing device.

13. The system of claim 1, further comprising the elongate rigidizing device.

14. A system for rigidizing an elongate rigidizing device at a target pressure, the system comprising:
- a pressure line configured to couple to a pressure inlet of the elongate rigidizing device;
- a pressure sensor configured to detect pressure within the pressure line;
- a vent valve in fluid communication with the pressure line;
- a supply valve in fluid communication with the pressure line;
- a controller coupled to the supply valve and configured to open the supply valve to apply a high-pressure pulse of pressurized fluid through the pressure line to rigidize the elongate rigidizing device, wherein the high-pressure pulse has a pressure that is higher than the target pressure, further wherein the controller is configured to detect a drop in the pressure within the pressure line that is below a threshold and to determine a leak rate, and to apply one or more additional pulses of pressurized fluid through the pressure line if the leak rate is greater than a slow leak threshold but less than a rapid leak threshold, and trigger an alert if the leak rate is greater than the rapid leak threshold.

15. A system for rigidizing an elongate rigidizing device at a target pressure, the system comprising:

a pressure line configured to couple to a pressure inlet of the elongate rigidizing device, wherein the elongate rigidizing device is configured to be rigidized from a flexible configuration to a rigid configuration;

a pressure sensor configured to detect pressure;

a vent valve in fluid communication with the pressure line;

a supply valve in fluid communication with the pressure line;

a controller in communication with the pressure sensor and configured to open the supply valve to apply a pulse of pressurized fluid through the pressure line to rigidize the elongate rigidizing device, wherein the pulse of the pressurized fluid is pressured to between about 2 and 10 atmospheres, further wherein the controller is configured to determine a leak rate and to automatically provide one or more additional pulses of the pressurized fluid if the leak rate is greater than a first threshold but less than a second threshold, and trigger an alert if the leak rate is greater than the second threshold.

* * * * *